US010375951B2

(12) United States Patent
Tsukamoto et al.

(10) Patent No.: US 10,375,951 B2
(45) Date of Patent: Aug. 13, 2019

(54) FERTILIZER AND AGROCHEMICAL FORMULATION

(71) Applicants: MITSUI CHEMICALS AGRO, INC., Chuo-ku, Tokyo (JP); HYPONEX JAPAN CORP., LTD., Osaka-shi, Osaka (JP)

(72) Inventors: Yoshihisa Tsukamoto, Kusatsu (JP); Daisuke Inoue, Ratchaburi (TH); Koichi Kiyotani, Kobe (JP); Yutaka Shiota, Tatsuno (JP)

(73) Assignees: MITSUI CHEMICALS AGRO, INC., Chuo-Ku, Tokyo (JP); HYPONEX JAPAN CORP., LTD., Osaka-Shi, Osaka (JP)

( * ) Notice: Subject to any disclaimer, the term of this patent is extended or adjusted under 35 U.S.C. 154(b) by 0 days.

(21) Appl. No.: 15/568,144

(22) PCT Filed: Apr. 20, 2016

(86) PCT No.: PCT/JP2016/002120
§ 371 (c)(1),
(2) Date: Oct. 20, 2017

(87) PCT Pub. No.: WO2016/170784
PCT Pub. Date: Oct. 27, 2016

(65) Prior Publication Data
US 2018/0139954 A1 May 24, 2018

(30) Foreign Application Priority Data
Apr. 20, 2015 (JP) ................. 2015-086227

(51) Int. Cl.
*A01N 25/02* (2006.01)
*A01N 43/40* (2006.01)
*A01N 47/40* (2006.01)
*A01N 47/42* (2006.01)
*A01N 51/00* (2006.01)
*C05G 3/02* (2006.01)
*C05G 3/00* (2006.01)
*C05B 17/00* (2006.01)
*C05D 9/02* (2006.01)

(52) U.S. Cl.
CPC ............ *A01N 25/02* (2013.01); *A01N 43/40* (2013.01); *A01N 51/00* (2013.01); *C05B 17/00* (2013.01); *C05D 9/02* (2013.01); *C05G 3/0064* (2013.01); *C05G 3/0076* (2013.01); *C05G 3/02* (2013.01); *A01N 47/40* (2013.01)

(58) Field of Classification Search
None
See application file for complete search history.

(56) References Cited

U.S. PATENT DOCUMENTS

2006/0166898 A1 7/2006 Chen
2014/0066405 A1 3/2014 Nishimura et al.

FOREIGN PATENT DOCUMENTS

| CN | 101 743 989 A | 6/2010 |
| EP | 2 708 123 A1 | 3/2014 |
| GB | 999 126 A | 7/1965 |
| JP | H-09-67204 A | 3/1997 |
| JP | 2008-120709 A | 5/2008 |
| JP | 2008-528513 A | 7/2008 |
| JP | 102 515 971 A | 6/2012 |

OTHER PUBLICATIONS

International Search Report (PCT/ISA/210) dated Jun. 28, 2016, by the Japanese Patent Office as the International Searching Authority for International Application No. PCT/JP2016/002120.
Written Opinion (PCT/ISA/237) dated Jun. 28, 2016, by the Japanese Patent Office as the International Searching Authority for International Application No. PCT/JP2016/002120.
Notification of Transmittal of Translation of the International Preliminary Report on Patentability (PCT Rule 71.1) (Form PCT/IPEA/416) and International Preliminary Report on Patentability (PCT Article 36 and Rule 70) (Form PCT/IPEA/409) dated Jul. 14, 2017, in the corresponding International Application No. PCT/JP2016/002120. (35 pages).
Palumbo, J.C., "Compatibility of Fertilizer and Neonicotinoid Soil Applications for Whitefly Control in Spring Cantaloupes", Retrieved from the Internet: URL:http://extension.arizona.edu/sites/extension.arizona.edu/files/pubs/az1323_1e.pdf, Aug. 1, 2003, XP55281001.

*Primary Examiner* — Alton N Pryor
(74) *Attorney, Agent, or Firm* — Buchanan, Ingersoll & Rooney PC

(57) ABSTRACT

A transparent, homogeneous liquid or liquiform fertilizer and agrochemical formulation is provided. The formulation includes an agrochemical and a fertilizer together with glycol ether.

36 Claims, No Drawings

FERTILIZER AND AGROCHEMICAL FORMULATION

TECHNICAL FIELD

The present invention relates to a fertilizer and agrochemical formulation, a fertilizer and agrochemical aqueous composition, methods for using the same, and a raw material for producing the fertilizer and agrochemical formulation.

BACKGROUND ART

The known mixture in the prior art combining the three components consisting of an agrochemical component, fertilizer component and glycol ether is only referred to Unexamined Patent Application Publication (Translation of PCT Application) No. 2008-528513 (Patent Literature 1) and Japanese Unexamined Patent Publication No. H9-67204 (Patent Literature 2).

Unexamined Patent Application Publication No. 2008-528513 (Patent Literature 1) describes a fertilizer composition comprising an agrochemically allowable mixture of a flowable thixotropic composition and liquid fertilizer composition, containing (a) an agrochemically active compound, (b) a metal lignosulfate, (c) a water-soluble salt of strong acid, and (d) water, wherein the compound is in the form of solid particles and/or liquid fine spheres having an average diameter sufficiently small for effectively dispersing in the composition, and the metal lignosulfate and water-soluble salt are mixed in an amount sufficient for allowing the particles and/or fine spheres to disperse in water. Japanese Unexamined Patent Publication No. H9-67204 (Patent Literature 2) relates to an aerosol preparation for controlling caterpillars containing an active ingredient, a propellant, a diluent and a spreading agent, and discloses an aerosol preparation comprising at least one of compound, as spreading agents, selected from the group consisting of various types of surfactants and glycol ethers.

CITATION LIST

Patent Literature

[PTL 1] Unexamined Patent Application Publication (Translation of PCT Application) No. 2008-528513
[PTL 2] Japanese Unexamined Patent Publication No. H9-67204

SUMMARY OF INVENTION

Technical Problem

However, the original technical issue of Patent Literature 1 is the compatibility of a fertilizer and agrochemical in a tank mixing, and assumes the use of a tank mix at the application site. The fertilizer composition of Patent Literature 1 is a suspension composition, and not only is there no description relating to a transparent, homogeneous liquid composition, but such a composition is also not assumed. In addition, Patent Literature 2 describes an aerosol preparation containing only one pyrethroid insecticide, that is Resmethrin, in each of the formulation examples, and although two of surfactants and two of diluents are added to these formulations, there is no disclosure whatsoever of a formulation containing glycol ether.

Because mixing of agrochemical components and fertilizer components causes problems such as insolubility of these components or the decomposition, precipitation or separation of each component, the satisfactory mixtures that have solved these problems are not known to exist. Thus, there has been a desire for a transparent, homogeneous water-containing fertilizer and agrochemical liquid formulation that demonstrates superior long-term stability in particular as well as reducing the risk of ignition and the like. However, technology for producing such a fertilizer and agrochemical formulation has heretofore not been known.

An object of the present invention is to provide a transparent, homogeneous liquiform fertilizer and agrochemical formulation that suppresses precipitation of the agrochemical component or fertilizer component along with decomposition and separation of each component, demonstrates superior long-term stability, and reduces the risk of ignition and the like, to provide an aqueous composition containing the fertilizer and agrochemical formulation, and to provide a raw material for producing the fertilizer and agrochemical formulation.

Solution to Problem

As a result of conducting extensive studies to solve the aforementioned problems, the inventors of the present invention found that, addition of glycol ether into a water-containing fertilizer and agrochemical composition, in order to dissolve an agrochemical component and fertilizer component, gives a transparent, homogeneous liquid or liquiform water-containing fertilizer and agrochemical mixed liquid formulation (fertilizer and agrochemical formulation), that is free of decomposition, precipitation or separation of the agrochemical component and fertilizer component, demonstrates superior long-term stability, and reduces the risk of ignition and the like, and found that a fertilizer and an agrochemical aqueous composition obtained by diluting the fertilizer and agrochemical formulation with water, to have similar effects as the formulation, thereby leading to completion of the present invention.

Namely, the present invention includes the aspects indicated below.

(1) A transparent, homogeneous liquid or liquiform fertilizer and agrochemical formulation includes an agrochemical and a fertilizer together with glycol ether.
(2) The formulation described in (1), which includes water.
(3) The formulation described in (1) or (2), wherein the agrochemical includes: an insecticide selected from the group consisting of carbamate acetylcholinesterase (AChE) inhibitors, organophosphorous acetylcholinesterase (AChE) inhibitors, cyclodiene organochlorine GABA-gated chlorine ion channel blockers, phenylpyrazole (fiprole) GABA-gated chlorine ion channel blockers, pyrethroid and pyrethrin sodium channel modulators, DDT and methoxychlor sodium channel modulators, neonicotinoid nicotinic acetylcholine receptor (nAChR) competitive modulators, nicotin nicotinic acetylcholine receptor (nAChR) competitive modulators, sulfoximine nicotinic acetylcholine receptor (nAChR) competitive modulators, butenolide nicotinic acetylcholine receptor (nAChR) competitive modulators, spinosyn nicotinic acetylcholine receptor (nAChR) allosteric modulators, avermectin and milbemycin glutamate-gated chloride channel (GluCl) allosteric modulators, juvenile hormone mimics, miscellaneous non-specific (multi site) inhibitors, pyridine azomethine derivative chordotonal organ TRPV channel modulators, mite growth inhibitors, microbial disruptors of insect midgut membranes, inhibitors of mitochondrial ATP synthase, uncouplers of oxidative phosphorylation via disruption of the proton gradient, nereistoxin analogue nicotinic acetylcholine receptor (nAChR) channel blockers, benzoylurea inhibitors of chitin biosynthesis (type 0), inhibitors of chitin biosynthesis (type 1), molting disruptors (dipteran), diacylhydrazine ecdysone receptor agonists, octopamine receptor agonists, mitochondrial complex III electron transport inhibitors, mitochondrial complex I electron transport inhibitors, voltage-dependent sodium channel blockers, tetronic acid and tetramic acid derivative inhibitors of acetyl CoA carboxylase, mitochondrial complex IV electron transport inhibitors, mitochondrial complex II electron transport inhibitors, diamide ryanodine receptor modulators, flonicamid chordotonal organ modulators (undefined target site), natural enemy insect, mite and nematode-based biopesticides, microbial pesticides, spiracle-blocking agrochemicals, pheromone agents, azadirachtin, benzomate (benzoximate), bifenazate, phenisobromolyate (bromopropylate), quinoxaline (quinomethionate), sodium aluminum fluoride, kelthane (such as dicofol), pyridalyl, pyrifluquinazon, sulfur, ferric phosphate agents, metaaldehyde and 1,3-dichloropropene;

a fungicide selected from the group consisting of acylanaline PA fungicides (phenylamides), oxazolidinone PA fungicides (phenylamides), butyrolactone-based PA fungicides (phenyl amides), hydroxyl(2-amino)pyrimidines, isoxazole heteroaromatics, isothiazolone heteroaromatics, carboxylic acids, benzoimidazole MBC fungicides (methyl benzimidazole carbamate), thiophanate MBC fungicides (methyl benzimidazole carbamate), N-phenylcarbamates, toluamide benzamides, ethylamino-thiazole-carboxamide thiazole carboxamides, phenylureas, pyridinylmethyl-benzamide benzamides, aminocyanoacrylate cyanoacrylates, pyrimidineamines, pyrazole-5-carboxamides pyrazole MET 1, phenyl-benzamide-based SDHI (succinate dehydrogenase inhibitors), phenyl-oxo-ethyl thiophene amide SDHI (succinate dehydrogenase inhibitors), pyridinyl-ethyl-benzamide-based SDHI (succinate dehydrogenase inhibitors), furan-carboxamide SDHI (succinate dehydrogenase inhibitors), oxathiin-carboxamide SDHI (succinate dehydrogenase inhibitors), thiazole-carboxamide SDHI (succinate dehydrogenase inhibitors), pyrazole-4-carboxamide SDHI (succinate dehydrogenase inhibitors), N-methoxy-(phenyl-ethyl)-pyrazole-carboxamide SDHI (succinate dehydrogenase inhibitors), pyridine-carboxamide SDHI (succinate dehydrogenase inhibitors), methoxy-acrylate QoI-fungicides (Quinone outside inhibitors), methoxy-acetamide QoI-fungicides (Quinone outside inhibitors), methoxy-carbamate QoI-fungicides (Quinone outside inhibitors), oxyimino-acetate QoI-fungicides (Quinone outside inhibitors), oxyimino-acetamide QoI-fungicides (Quinone outside inhibitors), oxazolidine-dione QoI-fungicides (Quinone outside inhibitors), dihydro-dioxadine QoI-fungicides (Quinone outside inhibitors), imidazolinone-based QoI-fungicides (Quinone outside inhibitors), benzyl-carbamate-based QoI-fungicides (Quinone outside inhibitors), cyano-imidazole-based QiI-fungicides (Quinone inside inhibitors), sulfamoyl-triazole QiI-fungicides (Quinone inside inhibitors), dinitrophenyl crotonates, 2,6-dinitroanilines, tri-phenyl tin compound organic tin compounds, thiophene carboxamides, triazolo-pyrimidylamine QoSI fungicides (Quinone outside inhibitors, stigmatellin binding type), anilino-pyrimidine AP-fungicides (aniline-pyrimidines), enopyranuronic acid antibiotics, hexopyranosyl antibiotics, glucopyranosyl antibiotics, tetracycline antibiotics, allyloxyquinoline aza-naphthalenes, quinazolinone aza-naphthalenes, phenylpyrrole PP-fungicides (phenylpyrroles), dicarboximides, phosphoro-thiolates, dithiolanes, aromatic hydrocarbon AH-fungicides (aromatic hydrocarbons, including chlorophenyls and nitroanilines), 1,2,4-thiadiazole heteroaromatics, carbamates, microbial (*Bacillus* species): *Bacillus* species and fungicidal lipopeptide lipopeptide produced, terpene hydrocarbon and terpene alcohol plant extracts, piperazine DMI-fungicides (demethylation inhibitors, SBI: class I), pyridine DMI-fungicides (demethylation inhibitors, SBI: class I), pyrimidine DMI-fungicides (demethylation inhibitors, SBI: class I), imidazole DMI-fungicides ((demethylation inhibitors, SBI: class I), triazole DMI-fungicides (demethylation inhibitors, SBI: class I), triazolinethione DMI-fungicides (demethylation inhibitors, SBI: class I), morpholine amines (morpholines, SBI: class II), piperidine amines (morpholines, SBI: class II), spiroketal-amine amines (morpholines, SBI: class II), hydroxyanilides (SBI: class III), aminopyrazolinones (SBI: class III), thiocarbamates (SBI: class IV), allylamines (SBI: class IV), glucopyranosyl antibiotics, peptidyl pyrimidine nucleotide polyoxines, cinnamic acid amide CAA-fungicides (carboxylic acid amides), valineamide carbamate CAA-fungicides (carboxylic acid amides), mandelic acid amide CAA-fungicides (carboxylic acid amides), isobenzo-furanone MBI-R (melanin biosynthesis inhibitors-reductases), pyrrolo-quinolinone MBI-R (melanin biosynthesis inhibitors-reductases), triazolobenzo-thiazole MBI-R (melanin biosynthesis inhibitors-reductases), cyclopropane-carboxamide MBI-D (melanin biosynthesis inhibitors-dehydrogenases), carboxamide MBI-D (melanin biosynthesis inhibitors-dehydrogenases), propionamide MBI-D (melanin biosynthesis inhibitors-dehydrogenases), trifluoroethyl-carbamate MBI-P (melanin biosynthesis inhibitors-polyketide synthase), benzo-thiadiazoles BTH, benzisothiazoles, thiadiazole-carboxamides, natural polysaccharides, plant extracts, cyanoacetamide-oximes, ethyl phosphonate phosphonates, phosphonates, phthalamic acids, benzotriazines, benzene-sulfonamides, pyridazinones, thiocarbamates, phenyl-acetamides, benzophenone allyl-phenyl-ketones, benzoylpyridine allyl-phenyl-ketones, guanidines, cyano-methylene-thiazolidine thiazolidines, pyrimidinone-hydrazones, piperidinyl-thiazole-isoxazolines, 4-quinoline acetates, tetrazolyloximes, glucopyranosyl antibiotics, inorganic compounds, dithio-carbamates and analogues thereof, phthalimides, chloronitriles (phthalonitriles), sulfamides, bis-guanidines, triazines, quinones (anthraquinones), quinoxalines, maleimides, polypeptides, physical inhibitors, bicarbonate agents, silver agents, organic copper agents and soil disinfectants; or, a herbicide selected from the group consisting of allyloxy propionate inhibitors of acetyl CoA carboxylase (ACCase), cyclohexanedione inhibitors of acetyl CoA carboxylase (ACCase), phenylpyrazoline inhibitors of acetyl CoA carboxylase (ACCase), sulfonylurea inhibitors of acetolactic acid synthase (ALS) (acetohydroxy acid synthase (AHAS) inhibitors), imidazolinone inhibitors of acetolactic acid synthase (ALS) (acetohydroxy acid synthase (AHAS) inhibitors), triazolopyrimidine inhibitors of acetolactic acid synthase (ALS) (acetohydroxy acid synthase (AHAS) inhibitors), pyrimidinyl(thio)benzoate inhibitors of acetolactic acid synthase (ALS) (acetohydroxy acid synthase (AHAS) inhibitors), sulfonylaminocarbonyl-triazolinone inhibitors of acetolactic acid synthase (ALS) (acetohydroxy acid synthase (AHAS) inhibitors), triazine inhibitors of photosynthesis at photochemical system II, triazinone inhibitors of photosynthesis at photochemical system II, triazolinone inhibitors of photosynthesis at photochemical system II, uracil inhibitors of photosynthesis at photochemical system II, pyridazinone inhibitors of photosynthesis at photochemical system II, phenyl-carbamate inhibitors of photosynthesis at photochemical system II, urea inhibitors of photosynthesis at photochemical system II, amide inhibitors of photosynthesis at photochemical system II, nitrile inhibitors of photosynthesis at photochemical system II, benzothiadiazinone inhibitors of photosynthesis at photochemical system II, phenyl-pyridazine inhibitors of photosynthesis at photochemical system II, bipyridylium photochemical system I electron diverting agents, diphenylether inhibitors of protoporphyrinogen oxidase (PPO), phenylpyrazole inhibitors of protoporphyrinogen oxidase (PPO), N-phenylphthalimide inhibitors of protoporphyrinogen oxidase (PPO), thiadiazole inhibitors of protoporphyrinogen oxidase (PPO), oxadiazole inhibitors of protoporphyrinogen oxidase (PPO), triazolinone inhibitors of protoporphyrinogen oxidase (PPO), oxazolidinedione inhibitors of protoporphyrinogen oxidase (PPO), pyrimidindione inhibitors of protoporphyrinogen oxidase (PPO), inhibitors of protoporphyrinogen oxidase (PPO), pyridazinone inhibitors of carotenoid biosynthesis at the phytoene desaturase step (PDS), pyridinecarboxamide inhibitors of carotenoid biosynthesis at the phytoene desaturase step (PDS), inhibitors of carotenoid biosynthesis at the phytoene desaturase step (PDS), triketone inhibitors of 4-hydroxyphenyl-pyruvate-dioxygenase (4-HPPD), isoxazole inhibitors of 4-hydroxyphenyl-pyruvate-dioxygenase (4-HPPD), pyrazole inhibitors of 4-hydroxyphenyl-pyruvate-dioxygenase (4-HPPD), inhibitors of 4-hydroxyphenyl-pyruvate-dioxygenase (4-HPPD), triazole inhibitors of carotenoid biosynthesis (unknown target site), isoxazolidinone inhibitors of carotenoid biosynthesis (unknown target site), urea inhibitors of carotenoid biosynthesis (unknown target site), diphenylether inhibitors of carotenoid biosynthesis (unknown target site), glycine inhibitors of EPSP synthase, phosphinic acid inhibitors of glutamine synthetase, carbamate inhibitors of DHP (dihydropteroate) synthase, dinitroaniline microtubule assembly inhibitors, phosphoramidate microtubule assembly inhibitors, pyridine microtubule assembly inhibitors, benzamide microtubule assembly inhibitors, benzoic acid microtubule assembly inhibitors, carbamate inhibitors of mitosis/microtubule organisation, chloroacetamide inhibitors of VLCFAs (inhibitors of cell division), acetamide inhibitors of VLCFAs (inhibitors of cell division), oxyacetamide inhibitors of VLCFAs (inhibitors of cell division), tetrazolinone inhibitors of VLCFAs (inhibitors of cell division), inhibitors of VLCFAs (inhibitors of cell division), nitrile inhibitors of cell wall (cellulose) synthesis, benzamide inhibitors of cell wall (cellulose) synthesis, triazolocarboxamide inhibitors of cell wall (cellulose) synthesis, quinoline carboxylic acid inhibitors of cell wall (cellulose) synthesis, dinitrophenol uncoupling (membrane disruption) agents, thiocarbamate inhibitors of lipid synthesis (non-ACCase inhibitors), phosphorodithioate inhibitors of lipid synthesis (non-ACCase inhibitors), benzofuran inhibitors of lipid synthesis (non-ACCase inhibitors), chloro-carbonic-acid inhibitors of lipid synthesis (non-ACCase inhibitors), phenoxy-carboxylic-acid indole acetic acid-like agents (synthetic auxins), benzoic acid indole acetic acid-like agents (synthetic auxins), pyridine carboxylic acid indole acetic acid-like agents (synthetic auxins), quinoline carboxylic acid indole acetic acid-like agents (synthetic auxins), indole acetic acid-like agents (synthetic auxins), phthalamate inhibitors of auxin transport, semicarbazone inhibitors of auxin transport, pyrazoliums, arylaminopropionic acids, organoarsenicals, microorganisms, bromobutide, (chlor)-flurenol, cinmethylin, cumyluron, dazomet, dymron, methyl dymron, etobenzanid, fosamine, indanofan, carbam/carbam sodium salt, oxaziclomefone, oleic acid, pelargonic acid, pyributicarb, chlorates and cyanates.

(4) The formulation described in any of (1) to (3), wherein the agrochemical includes:

an insecticide selected from the group consisting of carbamate acetylcholinesterase (AChE) inhibitors, organophosphorous acetylcholinesterase (AChE) inhibitors, phenylpyrazole (fiprole) GABA-gated chlorine ion channel blockers, pyrethroid and pyrethrin sodium channel modulators, neonicotinoid nicotinic acetylcholine receptor (nAChR) competitive modulators, sulfoximine nicotinic acetylcholine receptor (nAChR) competitive modulators, spinosyn nicotinic acetylcholine receptor (nAChR) allosteric modulators, avermectin and milbemycin glutamate-gated chloride channel (GluCl) allosteric modulators, chordotonal organ TRPV channel modulators, uncouplers of oxidative phosphorylation via disruption of the proton gradient, mitochondrial complex III electron transport inhibitors, mitochondrial complex I electron transport inhibitors, voltage-dependent sodium channel blockers, tetronic acid and tetramic acid derivative inhibitors of acetyl CoA carboxylase, diamide ryanodine receptor modulators, flonicamid chordotonal organ modulators (undefined target site), quinoxaline (quinomethionate), pyridalyl and metaaldehyde; or, a fungicide selected from the group consisting of acylanaline PA fungicides (phenylamides), oxazolidinone PA fungicides (phenylamides), butyrolactone PA fungicides (phenyl amides), isoxazole heteroaromatics, benzimidazole MBC fungicides (methyl benzimidazole carbamate), N-phenyl carbamates, phenyl-benzamide SDHI (succinate dehydrogenase inhibitors), phenyl-oxo-ethyl thiophene amide SDHI (succinate dehydrogenase inhibitors), pyridinyl-ethyl-benzamide SDHI (succinate dehydrogenase inhibitors), furan-carboxamide SDHI (succinate dehydrogenase inhibitors), oxathiin-carboxamide SDHI (succinate dehydrogenase inhibitors), thiazole-carboxamide SDHI (succinate dehydrogenase inhibitors), pyrazole-4-carboxamide SDHI (succinate dehydrogenase inhibitors), N-methoxy-(phenyl-ethyl)-pyrazole-carboxamide SDHI (succinate dehydrogenase inhibitors), pyridine-carboxamide SDHI (succinate dehydrogenase inhibitors), methoxy-acrylate QoI-fungicides (Quinone outside inhibitors), methoxy-acetamide QoI-fungicides (Quinone outside inhibitors), methoxy-carbamate QoI-fungicides (Quinone outside inhibitors), oximino-acetate QoI-fungicides (Quinone outside inhibitors), oximino-acetamide QoI-fungicides (Quinone outside inhibitors), oxazolidine-dione QoI-fungicides (Quinone outside inhibitors), dihydro-dioxazine QoI-fungicides (Quinone outside inhibitors), imidazolinone QoI-fungicides (Quinone outside inhibitors), benzyl-carbamate QoI-fungicides (Quinone outside inhibitors), cyano-imidazole QiI-fungicides (Quinone inside inhibitors), sulfamoyl-triazole QiI-fungicides (Quinone inside inhibitors), 2,6-dinitroanilines, anilino-pyrimidine AP-fungicides (aniline-pyrimidines), phenylpyrrole PP-fungicides (phenylpyrroles), di carboximides, piperazine DMI-fungicides (demethylation inhibitors, SBI: class I), pyridine DMI-fungicides (demethylation inhibitors, SBI: class I), pyrimidine DMI-fungicides (demethylation inhibitors, SBI: class I), imidazole DMI-fungicides (demethylation inhibitors, SBI: class I), triazole DMI-fungicides (demethylation inhibitors, SBI: class I), triazolinethione DMI-fungicides (demethylation inhibitors, SBI: class I), isobenzo-furanone MBI-R (melanin biosynthesis inhibitors-reductase), pyrrolo-quinolinone MBI-R (melanin biosynthesis inhibitors-reductase), triazolobenzo-thiazole MBI-R (melanin biosynthesis inhibitors-reductase), cyclopropane-carboxamide MBI-D (melanin biosynthesis inhibitors-dehydratase), carboxamide MBI-D (melanin biosynthesis inhibitors-dehydratase), propionamide MBI-D (melanin biosynthesis inhibitors-dehydratase), benzo-thiadiazoles BTH, benzisothiazoles, thiadiazole-carboxamides, cyanoacetamide-oximes, benzene-sulfonamides, pyridazinones, guanidines and quinoxalines.

(5) The formulation described in any of (1) to (4), wherein the agrochemical includes:

an insecticide selected from the group consisting of carbamate acetylcholinesterase (AChE) inhibitors, organophosphorous acetylcholinesterase (AChE) inhibitors, phenylpyrazole (fiprole) GABA-gated chlorine ion channel blockers, pyrethroid and pyrethrin sodium channel modulators, sodium channel modulators, neonicotinoid nicotinic acetylcholine receptor (nAChR) competitive modulators, sulfoximine nicotinic acetylcholine receptor (nAChR) competitive modulators, avermectin and milbemycin glutamate-gated chloride channel (GluCl) allosteric modulators, chordotonal organ TRPV channel modulators, uncouplers of oxidative phosphorylation via disruption of the proton gradient, diamide ryanodine receptor modulators, and flonicamid chordotonal organ modulators (undefined target site); or, a fungicide selected from the group consisting of isoxazole heteroaromatics, benzimidazole MBC fungicides (methyl benzimidazole carbamate), phenyl-benzamide SDHI (succinate dehydrogenase inhibitors), phenyl-oxoethyl thiophene amide SDHI (succinate dehydrogenase inhibitors), pyridinyl-ethyl-benzamide SDHI (succinate dehydrogenase inhibitors), furan-carboxamide SDHI (succinate dehydrogenase inhibitors), oxathiin-carboxamide SDHI (succinate dehydrogenase inhibitors), thiazole-carboxamide SDHI (succinate dehydrogenase inhibitors), pyrazole-4-carboxamide SDHI (succinate dehydrogenase inhibitors), N-methoxy-(phenyl-ethyl)-pyrazole-carboxamide SDHI (succinate dehydrogenase inhibitors), pyridine-carboxamide SDHI (succinate dehydrogenase inhibitors), methoxy-acrylate QoI-fungicides (Quinone outside inhibitors), methoxy-acetamide QoI-fungicides (Quinone outside inhibitors), methoxy-carbamate QoI-fungicides (Quinone outside inhibitors), oximino-acetate QoI-fungicides (Quinone outside inhibitors), oximino-acetamide QoI-fungicides (Quinone outside inhibitors), oxazolidine-dione QoI-fungicides (Quinone outside inhibitors), dihydro-dioxazine QoI-fungicides (Quinone outside inhibitors), imidazolinone QoI-fungicides (Quinone outside inhibitors), benzyl-carbamate QoI-fungicides (Quinone outside inhibitors), piperazine DMI-fungicides (demethylation inhibitors, SBI: class I), pyridine DMI-fungicides (demethylation inhibitors, SBI: class I), pyrimidine DMI-fungicides (demethylation inhibitors, SBI: class I), imidazole DMI-fungicides (demethylation inhibitors, SBI: class I), triazole DMI-fungicides (demethylation inhibitors, SBI: class I), triazolinethione DMI-fungicides (demethylation inhibitors, SBI: class I).

(6) The formulation described in any of (1) to (5), wherein the agrochemical has aqueous solubility at 25° C. of 100 ppm or more.

(7) The formulation described in any of (1) to (6), wherein the agrochemical includes:

an insecticide selected from the group consisting of aldicarb, bendiocarb, butocarboxim, butoxycarboxim, NAC (carbaryl), carbofuran, ethiofencarb, BPMC (fenobucarb), formetanate, MIPC (isoprocarb), methomyl, MTMC (metolcarb), oxamyl, pirimicarb, PHC (propoxur), thiofanox, triazamate, XMC, MPMC (xylylcarb), acephate, azamethiphos, cadusafos, CVP (chlorfenvinphos), demeton-S-methyl, DDVP (dichlorvos), dicrotophos, dimethoate, dimethylvinphos, ethoprophos, fenamiphos, fosthiazate, heptenophos, marathon (malathion), mecarbam, methamidophos, DMTP (methidathion), mevinphos, monocrotophos, omethoate, oxydemeton-methyl, phosphamidon, propetamphos, thiometon, DEP (trichlorfon), vamidothion, flumethrin, acetamiprid, clothianidin, dinotefuran, imidacloprid, nitenpyram, thiacloprid, thiamethoxam, nicotine sulfate (nicotine), sulfoxaflor, flupyradifurone, pyriproxyfen, methyl bromide (methylbromide), chloropicrin, sulfuryl fluoride, borax, tartar emetic, pymetrozine, flonicamid, BPPS (propargite), DNOC, cartap, thiocyclam, thiosultap-sodium, cyromazine, hydrogen phosphide, hydrogen cyanide, azadirachtin, sodium aluminum fluoride, 1,3-dichloropropene, dicyclanil, ethylene dibromide, sabadilla and sulcofuron-sodium; or, a fungicide selected from the group consisting of furalaxyl, metalaxyl, metalaxyl M, oxadixyl, ofurace, dimethirimol, hydroxyisoxazole (hymexazol), octhilinone, fenfuram, carboxin, oxycarboxin, furametpyr, metominostrobin, cyazofamid, pyrimethanil, kasugamycin, streptomycin, IBP (iprobenfos), echlomezol (etridiazole), propamocarb, prothiocarb, pyrifenox, imazalil, pefurazoate, triflumizole, flutriafol, myclobutanil, propiconazole, tetraconazole, fenpropidin, spiroxamine, validamycin, polyoxin, iprovalicarb, pyroquilon, cymoxanil, fosetyl, phosphorous acid and phosphites, flusulfamide, methasulfocarb, guanidine (dodine), ferimzone, potassium bicarbonate, ferbam, guazatine, iminoctadine acetate/iminoctadine albesilate (iminoctadine), copper sulfate, formaldehyde, 8-hydroxyquinoline sulfate, iodomethane, mercuric chloride, metam, methyl bromide, methyl isothiocyanate, mildiomycin, nabam, phenylmercuric acetate, 2-phenylphenol and polyoxin.

(8) The formulation described in any of (1) to (7), wherein the agrochemical includes at least one selected from the group consisting of acetamiprid, imidacloprid, clothianidin, dinotefuran, thiacloprid, thiamethoxam, nitenpyram and flonicamid.

(9) The formulation described in any of (1) to (8), wherein the agrochemical includes at least one of neonicotinoid selected from the group consisting of acetamiprid, imidacloprid, clothianidin, dinotefuran, thiacloprid, thiamethoxam and nitenpyram.

(10) The formulation described in any of (1) to (9), wherein the agrochemical includes at least one of neonicotinoid selected from the group consisting of acetamiprid, imidacloprid, clothianidin, dinotefuran and thiamethoxam.

(11) The formulation described in any of (1) to (10), wherein the agrochemical includes dinotefuran.

(12) The formulation described in any of (1) to (11), wherein the content ratio of the agrochemical is 0.01% by weight to 10% by weight.

(13) The formulation described in any of (1) to (12), wherein the fertilizer is a soluble fertilizer.

(14) The formulation described in (13), wherein the soluble fertilizer includes any of one or more of fertilizer components selected from the group consisting of nitrogen (N), phosphorous (P), potassium (K), silicon (Si), magnesium (Mg), manganese (Mn), boron (B), calcium (Ca) and sulfur (S) as plant essential elements.

(15) The formulation described in (13) or (14), wherein the soluble fertilizer includes at least two of fertilizer components selected from the group consisting of nitrogen (N), phosphorous (P) and potassium (K) as plant essential elements.

(16) The formulation described in any of (13) to (15), wherein the soluble fertilizer includes the fertilizer components of nitrogen (N), phosphorous (P) and potassium (K) as plant essential elements.

(17) The formulation described in any of (13) to (16), wherein the soluble fertilizer further includes any of one or more of fertilizer components selected from the group consisting of iron (Fe), copper (Cu), zinc (Zn), molybdenum (Mo), cobalt (Co) and chlorine (Cl) as plant essential elements.

(18) The formulation described in any of (13) to (17), wherein the soluble fertilizer includes nitrogen (N), phosphorous (P) and potassium (K) at a ratio of the guaranteed component amounts thereof of 1:2:1 as plant essential elements.

(19) The formulation described in any of (13) to (17), wherein the soluble fertilizer includes nitrogen (N), phosphorous (P) and potassium (K) at a ratio of the guaranteed component amounts thereof of 1.2:2:1 as plant essential elements.

(20) The formulation described in any of (13) to (19), wherein the content ratio of the soluble fertilizer is 0.1% by weight to 95% by weight.

(21) The formulation described in any of (1) to (20), wherein the glycol ether includes at least one selected from the group consisting of ethylene glycol monomethyl ether, ethylene glycol monoethyl ether, ethylene glycol monopropyl ether, ethylene glycol monoisopropyl ether, ethylene glycol monobutyl ether, ethylene glycol monoisobutyl ether, ethylene glycol mono-t-butyl ether, ethylene glycol mono-2-methylpentyl ether, ethylene glycol monohexyl ether, ethylene glycol mono-2-ethylhexyl ether, ethylene glycol monovinyl ether, ethylene glycol monoallyl ether, ethylene glycol monobenzyl ether, ethylene glycol monophenyl ether, ethylene glycol dimethyl ether, ethylene glycol diethyl ether, diethylene glycol monomethyl ether, diethylene glycol monoethyl ether, diethylene glycol monopropyl ether, diethylene glycol monoisopropyl ether, diethylene glycol monobutyl ether, diethylene glycol monoisobutyl ether, diethylene glycol monohexyl ether, diethylene glycol mono-2-ethylhexyl ether, diethylene glycol monoallyl ether, diethylene glycol monobenzyl ether, diethylene glycol monophenyl ether, diethylene glycol mono(methylphenyl) ether, diethylene glycol dimethyl ether, diethylene glycol methyl ethyl ether, diethylene glycol diethyl ether, diethylene glycol dibutyl ether, diethylene glycol divinyl ether, diethylene glycol ethyl vinyl ether, triethylene glycol monomethyl ether, triethylene glycol monoethyl ether, triethylene glycol monobutyl ether, triethylene glycol monovinyl ether, triethylene glycol dimethyl ether, tetraethylene glycol monophenyl ether, tetraethylene glycol diethyl ether, polyethylene glycol monomethyl ether, propylene glycol monomethyl ether, propylene glycol monoethyl ether, propylene glycol monopropyl ether, propylene glycol monoisopropyl ether, propylene glycol monobutyl ether, propylene glycol phenyl ether, propylene glycol mono(methylphenyl) ether, propylene glycol dimethyl ether, propylene glycol diethyl ether, propylene glycol dipropyl ether, propylene glycol diisopropyl ether, propylene glycol dibutyl ether, propylene glycol diisobutyl ether, propylene glycol diallyl ether, propylene glycol diphenyl ether, dipropylene glycol monomethyl ether, dipropylene glycol monoethyl ether, dipropylene glycol monopropyl ether, dipropylene glycol monobutyl ether, dipropylene glycol dimethyl ether, dipropylene glycol diethyl ether, dipropylene glycol dibutyl ether, dipropylene glycol diisobutyl ether, dipropylene glycol allyl ether, tripropylene glycol monomethyl ether, tripropylene glycol monoethyl ether, tripropylene glycol monobutyl ether, butylene glycol monomethyl ether, butylene glycol dimethyl ether and 3-methoxy-3-methyl-1-butanol.

(22) The formulation described in any of (1) to (21), wherein the glycol ether includes at least one selected from the group consisting of ethylene glycol monomethyl ether, ethylene glycol monoethyl ether, ethylene glycol monopropyl ether, ethylene glycol monoisopropyl ether, ethylene glycol monobutyl ether, ethylene glycol monoisobutyl ether, ethylene glycol monoallyl ether, diethylene glycol monomethyl ether, diethylene glycol monoethyl ether, diethylene glycol monopropyl ether, diethylene glycol monoisopropyl ether, diethylene glycol monobutyl ether, diethylene glycol monoisobutyl ether, diethylene glycol monobenzyl ether, diethylene glycol dimethyl ether, diethylene glycol methyl ethyl ether, diethylene glycol diethyl ether, triethylene glycol monomethyl ether, triethylene glycol monobutyl ether, triethylene glycol dimethyl ether, polyethylene glycol monomethyl ether, propylene glycol monomethyl ether, propylene glycol monopropyl ether, propylene glycol monobutyl ether, dipropylene glycol monomethyl ether, dipropylene glycol monopropyl ether, tripropylene glycol monomethyl ether, butylene glycol monomethyl ether and 3-methoxy-3-methyl-1-butanol.

(23) The formulation described in any of (1) to (22), wherein the glycol ether includes at least one selected from the group consisting of ethylene glycol monoisopropyl ether, ethylene glycol monobutyl ether, ethylene glycol monoisobutyl ether, ethylene glycol monoallyl ether, diethylene glycol monomethyl ether, diethylene glycol monoisopropyl ether, diethylene glycol monobutyl ether, diethylene glycol monoisobutyl ether, diethylene glycol monobenzyl ether, diethylene glycol dimethyl ether, diethylene glycol diethyl ether, diethylene glycol methyl ethyl ether, triethylene glycol monomethyl ether, triethylene glycol monobutyl ether, triethylene glycol dimethyl ether, polyethylene glycol monomethyl ether, propylene glycol monomethyl ether, propylene glycol monopropyl ether, dipropylene glycol monomethyl ether, tripropylene glycol monomethyl ether and 3-methoxy-3-methyl-1-butanol.

(24) The formulation described in any of (1) to (23), wherein the glycol ether includes at least one selected from the group consisting of ethylene glycol monobutyl ether, ethylene glycol monoisobutyl ether, ethylene glycol monoallyl ether, diethylene glycol monobutyl ether, diethylene glycol monoisobutyl ether, diethylene glycol monobenzyl ether, propylene glycol monopropyl ether and 3-methoxy-3-methyl-1-butanol.

(25) The formulation described in any of (1) to (24), wherein the glycol ether includes 3-methoxy-3-methyl-1-butanol.

(26) The formulation described in any of (1) to (25), wherein the content ratio of glycol ether is 0.1% by weight to 15% by weight.

(27) The formulation described in any of (1) to (26), wherein the content ratio of agrochemical is 0.01% by weight to 10% by weight, the content ratio of glycol ether is 0.1% by weight to 15% by weight, and the content ratio of soluble fertilizer is 0.1% by weight to 95% by weight.

(28) The formulation described in (27), wherein the content ratio of agrochemical is 0.03% by weight to 5% by weight, the content ratio of glycol ether is 3% by weight to 10% by weight, and the content ratio of soluble fertilizer is 50% by weight to 85% by weight.

(29) An aqueous composition for producing the formulation described in any of (1) to (28), wherein the aqueous composition includes a glycol ether, an agrochemical and water.

(30) The aqueous composition described in (29), wherein the glycol ether includes at least one selected from the group consisting of ethylene glycol monobutyl ether, ethylene glycol monoisobutyl ether, ethylene glycol monoallyl ether, diethylene glycol monobutyl ether, diethylene glycol monoisobutyl ether, diethylene glycol monobenzyl ether, propylene glycol monopropyl ether and 3-methoxy-3-methyl-1-butanol.

(31) The aqueous composition described in (29) or (30), wherein the glycol ether includes 3-methoxy-3-methyl-1-butanol.

(32) The aqueous composition described in any of (29) to (31), wherein the agrochemical includes at least one of neonicotinoid selected from the group consisting of acetamiprid, imidacloprid, clothianidin, dinotefuran, thiacloprid, thiamethoxam and nitenpyram.

(33) The aqueous composition described in any of (29) to (32), wherein the agrochemical includes dinotefuran.

(34) A transparent, homogeneous liquiform fertilizer and agrochemical aqueous composition, obtained by adding water to the formulation described in any of (1) to (28).

(35) A use of the formulation described in any of (1) to (28) or the composition described in (29) for agriculture, horticulture or home garden-use.

Advantageous Effects of Invention

According to the present invention, a transparent, homogeneous liquiform fertilizer and agrochemical formulation, which suppresses precipitation of the agrochemical component or fertilizer component, decomposition and separation of each component, demonstrates superior long-term stability, and reduces the risk of ignition and the like, an aqueous composition containing the fertilizer and agrochemical formulation, and a raw material that can produce the fertilizer and agrochemical formulation, can be provided.

DESCRIPTION OF EMBODIMENTS

The following provides an explanation of the various terms used in the present description.

The range of numerical values indicated using a term "to" in the present description refers to a range that includes those numerical values described before and after the term "to" as the minimum value and maximum value, respectively, thereof. Moreover, in a case in which each ingredient of a composition includes plural materials, the content of each ingredient of the composition denotes the total amount of the plural materials included in the composition unless specifically indicated otherwise.

A. Agrochemical

A term "agrochemical" refers to a fungicide, insecticide, and other chemicals that include materials using that chemical as a raw material or material used for the purpose of control, which are used to control fungi, nematodes, mites, insects, rodents and other animals and plants or viruses (to be referred to as "pests") that damage agricultural crops that include trees and forestry products, to be collectively referred to as "agricultural crops", and plant growth regulator, germination inhibitor or other chemical used to enhance or inhibit the physiological functions of agricultural crops. There are no particular limitations on the chemical used for agriculture, any chemical can be used, and may be any of an insecticide, fungicide or herbicide. Specific examples of agrochemicals include: insecticides selected from the group consisting of carbamate acetylcholinesterase (AChE) inhibitors such as alanycarb, aldicarb, bendiocarb, benfuracarb, butocarboxim, butoxycarboxim, NAC (carbaryl), carbofuran, carbosulfan, ethiofencarb, BMPC (fenobucarb), formetanate, furathiocarb, MIPC (isoprocarb), methiocarb, methomyl, MTMC (metolcarb), oxamyl, pirimicarb, PHC (propoxur), thiodicarb, thiofanox, triazamate, trimethacarb, XMC or MPMC (xylylcarb), organophosphorous acetylcholinesterase (AChE) inhibitors such as acephate, azamethiphos, azinphos-ethyl, azinphos-methyl, cadusafos, chlorethoxyfos, CVP (chlorfenvinphos), chlormephos, chlorpyrifos, chlorpyrifos-methyl, coumaphos, CYAP (cyanophos), demeton-S-methyl, diazinon, DDVP (dichlorvos), dicrotophos, dimethoate, dimethylvinphos, ethyl thiomethone (disulfoton), EPN, ethion, ethoprophos, famphur, fenamiphos, MEP (fenitrothion), MPP (fenthion), fosthiazate, heptenophos, imicyafos, isofenphos, isopropyl-O-(methoxyaminothio-phosphoryl) salicylate, isoxathion, marathon (malathion), mecarbam, methamidophos, DMTP (methidathion), mevinphos, monocrotophos, BRP (naled), omethoate, oxydemethone-methyl, parathion, parathion-methyl, PAP (phenthoate), phorate, phosalone, PMP (phosmet), phosphamidon, phoxim, pirimphos-methyl, profenofos, propetamphos, prothiofos, pyraclofos, pyridaphenthion, quinalphos, sulfotep, tebupirimfos, temephos, terbufos, CVMP (tetrachlorvinphos), thiometone, triazophos, DEP (trichlorfon) or vamidothion, cyclodiene organochlorine GABA-gated chlorine ion channel blockers such as chlordane or benzoepin (endosulfan), phenylpyrazole (fiprole) GABA-gated chlorine ion channel blockers such as ethiprole and fipronil, pyrethroid and pyrethrin sodium channel modulators such as acrinathrin, allethrin (allethrin, d-cis-trans-, d-trans-isomers), bifenthrin, bioallethrin (bioallethrin, S-cyclopentenyl isomer), bioresmethrin, cycloprothrin, cyfluthrin (cyfluthrin, beta-isomer), cyhalothrin (cyhalothrin, lamda-, gamma-isomers), cypermethrin (cypermethrin, alpha-, beta-, theta-, xi-isomers), cyphenothrin [(1R)-trans isomer], deltamethrin, empenthrin [(EZ)-(1R)-isomer], esfenvalerate, etofenprox, fenpropathrin, fenvalerate, flucythrinate, flumethrin, fluvalinate (tau-fluvalinate), halfenprox, imiprothrin, kadethrin, permethrin, phenothrin [(1R)-trans isomer], prallethrin, pyrethrin, resmethrin, silafluofen, tefluthrin, phthalthrin (tetramethrin), tetramethrin [(1R)-isomer] or tralomethrin or transfluthrin, DDT and methoxychlor sodium channel modulators such as DDT or methoxychlor, neonicotinoid-based nicotinic acetylcholine receptor (nAChR) competitive modulators such as acetamiprid, clothianidin, dinotefuran, imidacloprid, nitenpyram, thiacloprid or thiamethoxam, nicotin nicotinic acetylcholine receptor (nAChR) competitive modulators such as nicotine sulfate (nicotine), sulfoximine nicotinic acetylcholine receptor (nAChR) competitive modulators such as sulfoxaflor, butenolide nicotinic acetylcholine receptor (nAChR) competitive modulators such as such as spinetoram or spinosad, avermectin and milbemycin glutamate-gated chloride channel (GluCl) allosteric modulators such as abamectin, emamectin benzoate, lepimectin or milbemectin, juvenile hormone mimics such as hydroprene, kinoprene, methoprene, fenoxycarb or pyriproxyfen, miscellaneous non-specific (multisite) inhibitors such as methyl bromide (methylbromide), alkyl halides other than methyl bromide, chloropicrin, cryolite (sodium aluminum fluoride), sulfuryl fluoride, borax, boric acid, disodium octaborate, sodium borate, sodium metaborate, tartar emetic, dazomet or metam, pyridine azomethine derivative chordotonal organ TRPV channel modulators such as pymetrozine or pyrifluquinazon, mite growth inhibitors such as clofentezine, hexythiazox, diflovidazin or etoxazole, microbial disruptors of insect midgut membranes such as *Bacillus thuringiensis* subspecies *israelensis, B.t.* subsp. *aizawai, B.t.* subsp. *kurstaki, B.t.* subsp. *tenebrionis*, B. t. proteins contained in crops (Cry1Ab, Cry1Ac, Cry1Fa, Cry1A.105, Cry2Ab, Vip3A, mCry3A, Cry3Ab, Cry3Bb and Cry34Ab1/Cry35Ab1) or *Bacillus sphaericus*, inhibitors of mitochondrial ATP synthase such as diafenthiuron, azocyclotin, tricyclohexyltin hydroxide (cyhexatin), fenbutatin oxide, BPPS (propargite) or tetradifon, uncouplers of oxidative phosphorylation via disruption of the proton gradient such as chlorfenapyr, DNOC or sulfluramid, nereistoxin analogue nicotinic acetylcholine receptor (nAChR) channel blockers such as bensultap, cartap, thiocyclam or thiosultap-sodium, benzoylurea inhibitors of chitin biosynthesis (type 0) such as bistrifluron, chlorfluazuron, diflubenzuron, flucycloxuron, flufenoxuron, hexaflumuron, lufenuron, novaluron, noviflumuron, teflubenzuron or triflumuron, inhibitors of chitin biosynthesis (type 1) such as buprofezin, molting disruptors (dipteran) such as cyromazine, diacylhydrazine ecdysone receptor agonists such as chromafenozide, halofenozide, methoxyfenozide or tebufenozide, octopamine receptor agonists such as amitraz, mitochondrial complex III electron transport inhibitors such as hydramethylnon, acequinocyl, fluacrypyrim or bifenazate, mitochondrial complex I electron transport inhibitors such as fenazaquin, fenpyroximate, pyrimidifen, pyridaben, tebufenpyrad, tolfenpyrad or derris (rotenone), voltage-dependent sodium channel blockers such as indoxacarb or metaflumizone, tetronic acid and tetramic acid derivative inhibitors of acetyl CoA carboxylase such as spirodiclofen, spiromesifen or spirotetramat, mitochondrial complex IV electron transport inhibitors such as aluminium phosphide, calcium phosphide, phosphine, zinc phosphide, calcium cyanide, potassium cyanide or sodium cyanide, mitochondrial complex II electron transport inhibitors such as cyenopyrafen, cyflumetofen or pyflubumide, diamide ryanodine receptor modulators such as chlorantraniliprole, cyantraniliprole or flubendiamide, flonicamid chordotonal organ modulators (undefined target site) such as flonicamid, natural enemy insect, mite and nematode-based biopesticides such as *Steinernema carpocapsae, Phytoseiulus persimilis, Amblyseius cucumeris, Aphidoletes aphidimyza, Orius sauteri, Orius strigicollis, Encarsia formosa, Diglyphus isaea, Aphidius colemani, Dacnusa sibirica Telenga* or *Neochrysocharis formosa*, microbial pesticides such as *Pasteuria penetrans, Bacillus thuringiensis* (BT), *Monacrosporium phymatopagum, Paecilomyces tenuipes, Beauveria brongniartii* or *Beauveria bassiana*, spiracle-blocking agrochemicals such as starch, reduced starch saccharification products, machine oil or sodium oleate, pheromone agents such as Konagakon Plus, Confuser G, Confuser N, Confuser V, Sukashiba-con, Nitolure (fall webworm), Hamaki-con N, Ferodin SL, Yotoukon H or Yotoukon S, azadirachtin, benzomate (benzoximate), phenisobromolate (bromopropylate), chinomethionat, quinoxaline (quinomethionate), sodium aluminum fluoride, kelthane (dicofol), pyridalyl, pyrifluquinazon, sulfur, ferric phosphate agents, metaaldehyde and 1,3-dichloropropene;

fungicides selected from the group consisting of acylanaline PA fungicides (phenylamides) such as benalaxyl, benalaxyl M, furalaxyl, metalaxyl or metalaxyl M, oxazolidinone PA fungicides (phenylamides) such as oxadixyl, butyrolactone PA fungicides (phenylamides) such as ofurace, hydroxyl(2-amino)pyrimidines such as bupirimate, dimethirimol or ethirimol, isoxazole heteroaromatics such as hydroxyisoxazole (hymexazol), isothiazolone heteroaromatics such as octhilinone, carboxylic acids such as oxolinic acid, benzimidazole MBC fungicides (methyl benzimidazole carbamate) such as benomyl, carbendazole (carbendazim), fuberidazole or thiabendazole, thiophanate MBC fungicides (methyl benzimidazole carbamate) such as thiophanate or thiophanate-methyl, N-phenyl carbamates such as diethofencarb, toluamide benzamides such as zoxamide, ethylamino-thiazole-carboxamide thiazole carboxamides such as ethaboxam, phenylureas such as pencycuron, pyridinylmethyl-benzamide benzamides such as fluopicolide, aminocyanoacrylate cyanoacrylates such as phenamacril, pyrimidineamines such as diflumetorim, pyrazole-5-carboxamide pyrazole MET 1 such as tolfenpyrad, phenyl-benzamide SDHI (succinate dehydrogenase inhibitors) such as benodanil, flutolanil or mepronil, phenyl-oxo-ethyl thiophene amide SDHI (succinate dehydrogenase inhibitors) such as isofetamid, pyridinyl-ethyl-benzamide SDHI (succinate dehydrogenase inhibitors) such as fluopyram, furan-carboxamide SDHI (succinate dehydrogenase inhibitors) such as fenfuram, oxathiin-carboxamide SDHI (succinate dehydrogenase inhibitors) such as carboxin or oxycarboxin, thiazole-carboxamide SDHI (succinate dehydrogenase inhibitors) such as thifluzamide, pyrazole-4-carboxamide SDHI (succinate dehydrogenase inhibitors) such as benzovindiflupyr, bixafen, fluxapyroxad, furametpyr, isopyrazam, penflufen, penthiopyrad or sedaxane, N-methoxy-(phenyl-ethyl)-pyrazole-carboxamide SDHI (succinate dehydrogenase inhibitors) such as pydiflumetofen, pyridine-carboxamide SDHI (succinate dehydrogenase inhibitors) such as boscalid, methoxy-acrylate QoI-fungicides (Quinone outside inhibitors) such as azoxystrobin, coumoxystrobin, enoxastrobin, flufenoxystrobin, picoxystrobin or pyraoxystrobin, methoxy-acetamide QoI-fungicides (Quinone outside inhibitors) such as mandestrobin, methoxy-carbamate QoI-fungicides (Quinone outside inhibitors) such as pyraclostrobin, pyrametostrobin or triclopyricarb, oximino-acetate QoI-fungicides (Quinone outside inhibitors) such as kresoxim-methyl or trifloxystrobin, oximino-acetamide QoI-fungicides (Quinone outside inhibitors) such as dimoxystrobin, fenaminstrobin, metominostrobin or orysastrobin, oxazolidine-dione QoI-fungicides (Quinone outside inhibitors) such as famoxadone, dihydro-dioxazine QoI-fungicides (Quinone outside inhibitors) such as fluoxastrobin, imidazolinone QoI-fungicides (Quinone outside inhibitors) such as fenamidone, benzyl-carbamate QoI-fungicides (Quinone outside inhibitors) such as pyribencarb, cyano-imidazole QiI-fungicides (Quinone inside inhibitors) such as cyazofamid, sulfamoyl-triazole QiI-fungicides (Quinone inside inhibitors) such as amisulbrom, dinitrophenyl crotonates such as binapacryl, meptyldinocap or DPC (dinocap), 2,6-dinitroanilines such as fluazinam, tri-phenyl tin compound organic tin compounds such as fentin acetate, fentin chloride or fentin hydroxide, thiophene carboxamides such as silthiofam, triazolo-pyrimidylamine QoSI fungicides (Quinone outside inhibitors, stigmatellin binding type) such as ametoctradin, anilino-pyrimidine AP-fungicides (aniline-pyrimidines) such as cyprodinil, mepanipyrim or pyrimethanil, enopyranuronic acid antibiotics such as blasticidin-S, hexopyranosyl antibiotics such as kasugamycin, glucopyranosyl antibiotics such as streptomycin, tetracycline antibiotics such as oxytetracycline, allyloxyquinoline aza-naphthalenes such as quinoxyfen, quinazolinone aza-naphthalenes such as proquinazid, phenylpyrrole PP fungicides (phenylpyrroles) such as fenpiclonil or fludioxonil, dicarboximides such as chlozolinate, dimethachlone, iprodione, procymidone or vinclozolin, phosphoro-thiolates such as EDDP (edifenphos), IBP (iprobenfos) or pyrazophos, dithiolanes such as isoprothiolane, aromatic hydrocarbon AH-fungicides (aromatic hydrocarbons, including chlorophenyls and nitroanilines) such as biphenyl, chloroneb, CNA (dicloran), PCNB (quintozene), tecnazene or tolclofos-methyl, 1,2,4-thiadiazole heteroaromatics such as eclomezol (etridiazole), carbamates such as iodocarb, propamocarb or prothiocarb, microbial (Bacillus species): Bacillus species and the fungicidal lipopeptide produced such as Bacillus subtilis strain QST713, Bacillus subtilis strain FZB24, Bacillus subtilis strain MBI600 or Bacillus subtilis strain D747, terpene hydrocarbon and terpene alcohol plant extracts such as Melaleuca alternifolia (tea tree) extract, piperazine DMI fungicides (demethylation inhibitors, SBI: class I) such as triforine, pyridine DMI fungicides (demethylation inhibitors, SBI: class I) such as pyrifenox or pyrisoxazole, pyrimidine DMI fungicides (demethylation inhibitors, SBI: class I) such as fenarimol or nuarimol, imidazole DMI fungicides (demethylation inhibitors, SBI: class I) such as imazalil, oxpoconazole, pefurazoate, prochloraz or triflumizole, triazole DMI fungicides (demethylation inhibitors, SBI: class I) such as azaconazole, bitertanol, bromuconazole, cyproconazole, difenoconazole, diniconazole, epoxiconazole, etaconazole, fenbuconazole, fluquinconazole, flusilazole, flutriafol, hexaconazole, imibenconazole, ipconazole, metconazole, myclobutanil, penconazole, propiconazole, simeconazole, tebuconazole, tetraconazole, triadimefon, triadimenol or triticonazole, triazolinethione DMI fungicides (demethylation inhibitors, SBI: class I) such as prothioconazole, morpholine amines (morpholines, SBI: class II) such as aldimorph, dodemorph, fenpropimorph or tridemorph, piperidine amines (morpholines, SBI: class II) such as fenpropidin or piperalin, spiroketal-amine amines (morpholines, SBI: class II) such as spiroxamine, hydroxyanilides (SBI: class III) such as fenhexamid, amino-pyrazolinones (SBI: class III) such as fenpyrazamine, thiocarbamates (SBI: class IV) such as pyributicarb, allylamines (SBI: class IV) such as naftifine or terbinafine, peptidyl pyrimidine nucleotide polyoxines such as polyoxin, cinnamic acid amide CAA fungicides (carboxylic acid amides) such as dimethomorph, flumorph or pyrimorph, valinamide carbamate CAA fungicides (carboxylic acid amides) such as benthiavalicarb, iprovalicarb or valifenalate, mandelic acid amide CAA fungicides (carboxylic acid amides) such as mandipropamid, isobenzo-furanone MBI-R (melanin biosynthesis inhibitors-reductase) such as fthalide, pyrroloquinolinone MBI-R (melanin biosynthesis inhibitors-reductase) such as pyroquilon, triazolobenzo-thiazole MBI-R (melanin biosynthesis inhibitors-reductase) such as tricyclazole, cyclopropane-carboxamide MBI-D (melanin biosynthesis inhibitors-dehydratase) such as carpropamid, carboxamide MBI-D (melanin biosynthesis inhibitors-dehydratase) such as diclocymet, propionamide MBI-D (melanin biosynthesis inhibitors-dehydratase) such as fenoxanil, trifluoroethyl-carbamate MBI-P (melanin biosynthesis inhibitors-polyketide synthase) such as tolprocarb, benzo-thiadiazoles BTH such as acibenzolar-S-methyl, benzisothiazoles such as probenazole, thiadiazole carboxamides such as tiadinil or isotianil, natural polysaccharides such as laminarin, plant extracts such as Reynoutria sachalinensis extract, cyanoacetamide-oximes such as cymoxanil, ethyl phosphonate phosphonates such as fosetyl-Al, phosphonates such as phosphorous acid and salts, phthalamic acids such as teclofthalam, benzotriazines such as triazoxide, benzene-sulfonamides such as flusulfamide, pyridazinones such as diclomezine, thiocarbamates such as methasulfocarb, phenyl-acetamides such as cyflufenamid, benzophenone allyl-phenyl-ketones such as metrafenone, benzoylpyridine allyl-phenyl-ketones such as pyriofenone, guanidines such as guanidine (dodine), cyano-methylene-thiazolidine thiazolidines such as flutianil, pyrimidinone-hydrazones such as ferimzone, piperidinyl-thiazole-isoxazolines such as oxathiapiprolin, 4-quinoline-acetates such as tebufloquin, tetrazolyloximes such as picarbutrazox, glucopyranosyl antiobiotics such as validamycin, inorganic compounds such as copper (various salts) or sulfur, dithio-carbamates and analogues thereof such as ferbam, manzeb, maneb, metiram, propineb, thiuram, zineb or ziram, phthalimides such as captan, difoltan (captafol) or folpet, chloronitriles (phthalonitriles) such as TPN (chlorothalonil), sulfamides such as sulfene (dichlofluanid) or tolyfluanid, bis-guanidines such as guazatine or iminoctadine acetate/iminoctadine albesilate (iminoctadine), triazines such as triazine (anilazine), quinones (anthraquinones) such as dithianon, quinoxalines such as quinoxaline (quinomethionate), maleimides such as fluoroimide, polypeptides such as extract from the cotyledons of lupine plantlets ("PLAD"), physical inhibitors such as machine oil or organic oil, bicarbonate agents such as potassium bicarbonate, silver agents, organic copper agents such as 8-hydroxyquinoline copper, dodecylbenzenesulfonic acid bis(ethylenediamine) copper(II) complex salt or copper nonylphenol sulfonate, and soil disinfectants such as dazomet, chloropicrin, methyl isothiocyanate, carbam-sodium or ammonium N-methyldithiocarbaminate; and, herbicides selected from the group consisting of allyloxy propionate inhibitors of acetyl CoA carboxylase (ACCase) such as clodinafop-propargyl, cyhalofop-butyl, diclofop-methyl, fenoxaprop-P-ethyl, fluazifop P, haloxyfop-R-methyl, propaquizafop or quizalofop-p-ethyl, cyclohexanedione inhibitors of acetyl CoA carboxylase (ACCase) such as alloxydim, butroxydim, clethodim, cycloxydim, profoxydim, sethoxydim, tepraloxydim or tralkoxydim, phenylpyrazoline inhibitors of acetyl CoA carboxylase (ACCase) such as pinoxaden, sulfonylurea inhibitors of acetolactic acid synthase (ALS) (acetohydroxy acid synthase (AHAS) inhibitors) such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron, foramsulfuron, halosulfuron-methyl, imazosulfuron, iodosulfuron, mesosulfuron, metsulfuron-methyl, nicosulfuron, oxasulfuron, primisulfuron, prosulfuron, pyrazosulfuron-ethyl, rimsulfuron, sulfometuron-methyl, sulfosulfuron, thifensulfuron-methyl, triasulfuron or tritosulfuron, imidazolinone inhibitors of acetolactic acid synthase (ALS) (acetohydroxy acid synthase (AHAS) inhibitors) such as imazapic, imazamethabenz methyl, imazamox, imazapyr, imazaquin or imazethapyr, triazolopyrimidine inhibitors of acetolactic acid synthase (ALS) (acetohydroxy acid synthase (AHAS) inhibitors) such as cloransulam-methyl, diclosulam, florasulam, flumetsulam, metosulam or penoxsulam, pyrimidinyl(thio)benzoate inhibitors of acetolactic acid synthase (ALS) (acetohydroxy acid synthase (AHAS) inhibitors) such as bispyribac-sodium, pyribenzoxim, pyriftalid, pyrithiobac-sodium or pyriminobac-methyl, sulfonylaminocarbonyl-triazolinone inhibitors of acetolactic acid synthase (ALS) (acetohydroxy acid synthase (AHAS) inhibitors) such as flucarbazone-sodium or propoxycarbazone-sodium, triazine inhibitors of photosynthesis at photochemical system II such as ametryn, atrazine, cyanazine, desmetryn, dimethametryn, prometon, prometryn, propazines (propazine), CAT (simazine), simetryn, terbumeton, terbuthylazine, terbutryn or trietazine, triazinone inhibitors of photosynthesis at photochemical system II such as hexazinone, metamitron or metribuzin, triazolinone inhibitors of photosynthesis at photochemical system II such as amicarbazone, uracil inhibitors of photosynthesis at photochemical system II such as bromacil, lenacil or terbacil, pyridazinone inhibitors of photosynthesis at photochemical system II such as PAC (chloridazon), phenyl-carbamate inhibitors of photosynthesis at photochemical system II such as desmedipham or phenmedipham, urea inhibitors of photosynthesis at photochemical system II such as chlorbromuron, chlorotoluron, chloroxuron, dimefuron, DCMU (diuron), ethidimuron, fenuron, fluometuron, isoproturon, isouron, linuron, methabenzthiazuron, metobromuron, metoxuron, monolinuron, neburon, siduron or tebuthiuron, amide inhibitors of photosynthesis at photochemical system II such as DCPA (propanil) or CMMP (pentanochlor), nitrile inhibitors of photosynthesis at photochemical system II such as bromofenoxim, bromoxynil or ioxynil, benzothiadiazinone inhibitors of photosynthesis at photochemical system II such as bentazon, phenyl-pyridazine inhibitors of photosynthesis at photochemical system II such as pyridate or pyridafol, bipyridylium photochemical system I electron diverting agents such as diquat or paraquat, diphenylether inhibitors of protoporphyrinogen oxidase (PPO) such as acifluorfen, bifenox, chlomethoxynil (chlomethoxyfen), fluoroglycofen-ethyl, fomesafen, halosafen, lactofen or oxyfluorfen, phenylpyrazole inhibitors of protoporphyrinogen oxidase (PPO) such as fluazolate or pyraflufen-ethyl, N-phenylphthalimide inhibitors of protoporphyrinogen oxidase (PPO) such as cinidon-ethyl, flumioxazin or flumiclorac-pentyl, thiadiazole inhibitors of protoporphyrinogen oxidase (PPO) such as fluthiacet-methyl or thidiazimin, oxadiazole inhibitors of protoporphyrinogen oxidase (PPO) such as oxadiazon or oxadiargyl, triazolinone inhibitors of protoporphyrinogen oxidase (PPO) such as azafenidin, carfentrazone-ethyl or sulfentrazone, oxazolidinedione inhibitors of protoporphyrinogen oxidase (PPO) such as pentoxazone, pyrimidindione inhibitors of protoporphyrinogen oxidase (PPO) such as benzfendizone or butafenacil, inhibitors of protoporphyrinogen oxidase (PPO) such as pyraclonil, profluazol or flufenpyr-ethyl, pyridazinone inhibitors of carotenoid biosynthesis at the phytoene desaturase step (PDS) such as norflurazon, pyridinecarboxamide inhibitors of carotenoid biosynthesis at the phytoene desaturase step (PDS) such as diflufenican or picolinafen, inhibitors of carotenoid biosynthesis at the phytoene desaturase step (PDS) such as beflubutamid, fluridone, flurochloridone or flurtamone, triketone inhibitors of 4-hydroxyphenyl-pyruvate-dioxygenase (4-HPPD) such as mesotrione or sulcotrione, isoxazole inhibitors of 4-hydroxyphenyl-pyruvate-dioxygenase (4-HPPD) such as isoxachlortole or isoxaflutole, pyrazole inhibitors of 4-hydroxyphenyl-pyruvate-dioxygenase (4-HPPD) such as benzofenap, pyrazolate (pyrazolynate) or pyrazoxyfen, inhibitors of 4-hydroxyphenyl-pyruvate-dioxygenase (4-HPPD) such as benzobicyclon, triazole inhibitors of carotenoid biosynthesis (unknown target site) such as ATA (amitrole), isoxazolidinone inhibitors of carotenoid biosynthesis (unknown target site) such as clomazone, urea inhibitors of carotenoid biosynthesis (unknown target site) such as fluometuron, diphenylether inhibitors of carotenoid biosynthesis (unknown target site) such as aclonifen, glycine inhibitors of EPSP synthase such as glyphosate or glyphosate-trimesium (sulfosate), phosphinic acid inhibitors of glutamine synthetase such as glufosinate or bialaphos (bilanafos), carbamate inhibitors of DHP (dihydropteroate) synthase such as asulam, dinitroaniline microtubule assembly inhibitors such as bethrodine (benfluralin), butralin, dinitramine, ethalfluralin, oryzalin, pendimethalin or trifluralin, phosphoramidate microtubule assembly inhibitors such as amiprophos-methyl or butamifos, pyridine microtubule assembly inhibitors such as dithiopyr or thiazopyr, benzamide microtubule assembly inhibitors such as propyzamide or tebutam, benzoic acid microtubule assembly inhibitors such as TCTP (chlorthal-dimethyl), carbamate inhibitors of mitosis/microtubule organisation such as IPC (chlorpropham), propham or carbetamide, chloroacetamide inhibitors of VLCFAs (inhibitors of cell division) such as acetochlor, alachlor, butachlor, dimethachlor, dimethenamid, metazachlor, metolachlor, pethoxamid, pretilachlor, propachlor, propisochlor or thenylchlor, acetamide inhibitors of VLCFAs (inhibitors of cell division) such as diphenamid, napropamide or naproanilide, oxyacetamide inhibitors of VLCFAs (inhibitors of cell division) such as flufenacet or mefenacet, tetrazolinone inhibitors of VLCFAs (inhibitors of cell division) such as fentrazamide, inhibitors of VLCFAs (inhibitors of cell division) such as anilofos, cafenstrole or piperophos, nitrile inhibitors of cell wall (cellulose) synthesis such as DBN (dichlobenil) or DCBN (chlorthiamid), benzamide inhibitors of cell wall (cellulose) synthesis such as isoxaben, triazolocarboxamide inhibitors of cell wall (cellulose) synthesis such as flupoxam, quinoline carboxylic acid inhibitors of cell wall (cellulose) synthesis such as quinclorac, dinitrophenol uncoupling (membrane disruption) agents such as DNOC, DNBP (dinoseb) or dinoterb, thiocarbamate inhibitors of lipid synthesis (non-ACCase inhibitors) such as butylate, hexylthiocarbam (cycloate), dimepiperate, EPTC, esprocarb, molinate, orbencarb, pebulate, prosulfocarb, benthiocarb (thiobencarb), tiocarbazil, triallate or vernolate, phosphorodithioate inhibitors of lipid synthesis (non-ACCase inhibitors) such as SAP (bensulide), benzofuran inhibitors of lipid synthesis (non-ACCase inhibitors) such as benfuresate or ethofumesate, chloro-carbonic-acid inhibitors of lipid synthesis (non-ACCase inhibitors) such as TCA, DPA (dalapon) or tetrapion (flupropanate), phenoxy-carboxylic-acid indole acetic acid-like agents (synthetic auxins) such as clomeprop, 2,4-PA (2,4-D), 2,4-DB, dichlorprop, MCPA, MCPB or MCPP (mecoprop), benzoic acid indole acetic acid-like agents (synthetic auxins) such as chloramben, MDBA (dicamba) or TCBA (2,3,6-TBA), pyridine carboxylic acid indole acetic acid-like agents (synthetic auxins) such as clopyralid, fluroxypyr, picloram or triclopyr, quinoline carboxylic acid indole acetic acid-like agents (synthetic auxins) such as quinclorac or quinmerac, indole acetic acid-like agents (synthetic auxins) such as benazolin-ethyl, phthalamate inhibitors of auxin transport such as NPA (naptalam), semicarbazone inhibitors of auxin transport such as diflufenzopyr-sodium, arylaminopropionic acids such as flamprop-M-methyl/isopropyl, pyrazoliums such as difenzoquat, organoarsenicals such as DMSA or MSMA, microorganisms such as *Xanthomonas campestris*, bromobutide, (chlor)-flurenol, cinmethylin, cumyluron, dazomet, dymron, methyl dymron, etobenzanid, fosamine, indanofan, carbam/carbam sodium salt, oxaziclomefone, oleic acid, pelargonic acid, pyributicarb, chlorates and cyanates.

Among these, the agrochemical is preferably an insecticide selected from the group consisting of carbamate acetylcholinesterase (AChE) inhibitors, organophosphorous acetylcholinesterase (AChE) inhibitors, phenylpyrazole (fiprole) GABA-gated chlorine ion channel blockers, pyrethroid and pyrethrin sodium channel modulators, sodium channel modulators, neonicotinoid nicotinic acetylcholine receptor (nAChR) competitive modulators, sulfoximine nicotinic acetylcholine receptor (nAChR) competitive modulators, spinosyn nicotinic acetylcholine receptor (nAChR) allosteric modulators, avermectin and milbemycin glutamate-gated chloride channel (GluCl) allosteric modulators, chordotonal organ TRPV channel modulators, uncouplers of oxidative phosphorylation via disruption of the proton gradient, mitochondrial complex III electron transport inhibitors, mitochondrial complex I electron transport inhibitors, voltage-dependent sodium channel blockers, tetronic acid and tetramic acid derivative inhibitors of acetyl CoA carboxylase, diamide ryanodine receptor modulators, flonicamid chordotonal organ modulators (undefined target site), quinoxaline (quinomethionate), pyridalyl and metaaldehyde; or, a fungicide selected from the group consisting of acylanaline PA fungicides (phenylamides), oxazolidinone PA fungicides (phenylamides), butyrolactone PA fungicides (phenyl amides), isoxazole heteroaromatics, benzimidazole MBC fungicides (methyl benzimidazole carbamate), N-phenyl carbamates, phenyl-benzamide SDHI (succinate dehydrogenase inhibitors), phenyl-oxo-ethyl thiophene amide SDHI (succinate dehydrogenase inhibitors), pyridinyl-ethyl-benzamide SDHI (succinate dehydrogenase inhibitors), furan-carboxamide SDHI (succinate dehydrogenase inhibitors), oxathiin-carboxamide SDHI (succinate dehydrogenase inhibitors), thiazole-carboxamide SDHI (succinate dehydrogenase inhibitors), pyrazole-4-carboxamide SDHI (succinate dehydrogenase inhibitors), N-methoxy-(phenyl-ethyl)-pyrazole-carboxamide SDHI (succinate dehydrogenase inhibitors), pyridine-carboxamide SDHI (succinate dehydrogenase inhibitors), methoxy-acrylate QoI-fungicides (Quinone outside inhibitors), methoxy-acetamide QoI-fungicides (Quinone outside inhibitors), methoxy-carbamate QoI-fungicides (Quinone outside inhibitors), oximino-acetate QoI-fungicides (Quinone outside inhibitors), oximino-acetamide QoI-fungicides (Quinone outside inhibitors), oxazolidine-dione QoI-fungicides (Quinone outside inhibitors), dihydro-dioxazine QoI-fungicides (Quinone outside inhibitors), imidazolinone QoI-fungicides (Quinone outside inhibitors), benzyl-carbamate QoI-fungicides (Quinone outside inhibitors), cyano-imidazole QiI-fungicides (Quinone inside inhibitors), sulfamoyl-triazole QiI-fungicides (Quinone inside inhibitors), 2,6-dinitroanilines, anilino-pyrimidine AP-fungicides (aniline-pyrimidines), phenylpyrrole PP-fungicides (phenylpyrroles), dicarboximides, piperazine DMI-fungicides (demethylation inhibitors, SBI: class I), pyridine DMI-fungicides (demethylation inhibitors, SBI: class I), pyrimidine DMI-fungicides (demethylation inhibitors, SBI: class I), imidazole DMI-fungicides ((demethylation inhibitors, SBI: class I), triazole DMI-fungicides (demethylation inhibitors, SBI: class I), triazolinethione DMI-fungicides (demethylation inhibitors, SBI: class I), isobenzo-furanone MBI-R (melanin biosynthesis inhibitors-reductase), pyrrolo-quinolinone MBI-R (melanin biosynthesis inhibitors-reductase), triazolobenzo-thiazole MBI-R (melanin biosynthesis inhibitors-reductase), cyclopropane-carboxamide MBI-D (melanin biosynthesis inhibitors-dehydratase), carboxamide MBI-D (melanin biosynthesis inhibitors-dehydratase), propionamide MBI-D (melanin biosynthesis inhibitors-dehydratase), benzo-thiadiazoles BTH, benzisothiazoles, thiadiazole-carboxamides, cyanoacetamide-oximes, benzene-sulfonamides, pyridazinones, guanidines and quinoxalines.

The agrochemical is particularly preferably an insecticide selected from the group consisting of carbamate acetylcholinesterase (AChE) inhibitors, organophosphorous acetylcholinesterase (AChE) inhibitors, phenylpyrazole (fiprole) GABA-gated chlorine ion channel blockers, pyrethroid and pyrethrin sodium channel modulators, sodium channel modulators, neonicotinoid nicotinic acetylcholine receptor (nAChR) competitive modulators, sulfoximine nicotinic acetylcholine receptor (nAChR) competitive modulators, avermectin and milbemycin glutamate-gated chloride channel (GluCl) allosteric modulators, chordotonal organ TRPV channel modulators, uncouplers of oxidative phosphorylation via disruption of the proton gradient, diamide ryanodine receptor modulators, and flonicamid chordotonal organ modulators (undefined target site); or, a fungicide selected from the group consisting of isoxazole heteroaromatics, benzimidazole MBC fungicides (methyl benzimidazole carbamate), phenyl-benzamide SDHI (succinate dehydrogenase inhibitors), phenyl-oxo-ethyl thiophene amide SDHI (succinate dehydrogenase inhibitors), pyridinyl-ethyl-benzamide SDHI (succinate dehydrogenase inhibitors), furan-carboxamide SDHI (succinate dehydrogenase inhibitors), oxathiin-carboxamide SDHI (succinate dehydrogenase inhibitors), thiazole-carboxamide SDHI (succinate dehydrogenase inhibitors), pyrazole-4-carboxamide SDHI (succinate dehydrogenase inhibitors), [N-methoxy-(phenyl-ethyl)-pyrazole-carboxamide SDHI (succinate dehydrogenase inhibitors)], pyridine-carboxamide SDHI (succinate dehydrogenase inhibitors), methoxy-acrylate QoI-fungicides (Quinone outside inhibitors), methoxy-acetamide QoI-fungicides (Quinone outside inhibitors), methoxy-carbamate QoI-fungicides (Quinone outside inhibitors), oximino-acetate QoI-fungicides (Quinone outside inhibitors), oximino-acetamide QoI-fungicides (Quinone outside inhibitors), oxazolidine-dione QoI-fungicides (Quinone outside inhibitors), dihydro-dioxazine QoI-fungicides (Quinone outside inhibitors), imidazolinone QoI-fungicides (Quinone outside inhibitors), benzyl-carbamate QoI-fungicides (Quinone outside inhibitors), piperazine DMI-fungicides (demethylation inhibitors, SBI: class I), pyridine DMI-fungicides (demethylation inhibitors, SBI: class I), pyrimidine DMI-fungicides (demethylation inhibitors, SBI: class I), imidazole DMI-fungicides ((demethylation inhibitors, SBI: class I), triazole DMI-fungicides (demethylation inhibitors, SBI: class I), triazolinethione DMI-fungicides (demethylation inhibitors, SBI: class I).

Specific examples of agrochemicals include: insecticides selected from the group consisting of aldicarb, bendiocarb, butocarboxim, butoxycarboxim, NAC (carbaryl), carbofuran, ethiofencarb, BPMC (fenobucarb), formetanate, MIPC (isoprocarb), methomyl, MTMC (metolcarb), oxamyl, pirimicarb, PHC (propoxur), thiofanox, triazamate, XMC, MPMC (xylylcarb), acephate, azamethiphos, cadusafos, CVP (chlorfenvinphos), demeton-S-methyl, DDVP (dichlorvos), dicrotophos, dimethoate, dimethylvinphos, ethoprophos, fenamiphos, fosthiazate, heptenophos, marathon (malathion), mecarbam, methamidophos, DMTP (methidathion), mevinphos, monocrotophos, omethoate, oxydemeton-methyl, phosphamidon, propetamphos, thiometon, DEP (trichlorfon), vamidothion, flumethrin, acetamiprid, clothianidin, dinotefuran, imidacloprid, nitenpyram, thiacloprid, thiamethoxam, nicotine sulfate (nicotine), sulfoxaflor, flupyradifurone, pyriproxyfen, methyl bromide (methylbromide), chloropicrin, sulfuryl fluoride, borax, tartar emetic, pymetrozine, flonicamid, BPPS (propargite), DNOC, cartap, thiocyclam, thiosultap-sodium, cyromazine, hydrogen phosphide, hydrogen cyanide, azadirachtin, sodium aluminum fluoride, 1,3-dichloropropene, dicyclanil, ethylene dibromide, sabadilla and sulcofuron-sodium; and, fungicides selected from the group consisting of furalaxyl, metalaxyl, metalaxyl M, oxadixyl, ofurace, dimethirimol, hydroxyisoxazole (hymexazol), octhilinone, fenfuram, carboxin, oxycarboxin, furametpyr, metominostrobin, cyazofamid, pyrimethanil, kasugamycin, streptomycin, IBP (iprobenfos), echlomezol (etridiazole), propamocarb, prothiocarb, pyrifenox, imazalil, pefurazoate, triflumizole, flutriafol, myclobutanil, propiconazole, tetraconazole, fenpropidin, spiroxamine, validamycin, polyoxin, iprovalicarb, pyroquilon, cymoxanil, fosetyl, phosphorous acid and phosphites, flusulfamide, methasulfocarb, guanidine (dodine), ferimzone, potassium bicarbonate, ferbam, guazatine, iminoctadine acetate/iminoctadine albesilate (iminoctadine), copper sulfate, formaldehyde, 8-hydroxyquinoline sulfate, iodomethane, mercuric chloride, metam, methyl bromide, methyl isothiocyanate, mildiomycin, nabam, phenylmercuric acetate, 2-phenylphenol and polyoxin, and the agrochemical preferably contains at least one selected therefrom.

Among these, the agrochemical preferably includes at least one selected from the group consisting of acetamiprid, imidacloprid, clothianidin, dinotefuran, thiacloprid, thiamethoxam, nitenpyram and flonicamid, more preferably includes at least one selected from the group consisting of acetamiprid, imidacloprid, clothianidin, dinotefuran, thiacloprid, thiamethoxam and nitenpyram, even more preferably includes at least one selected from the group consisting of acetamiprid, imidacloprid, clothianidin, dinotefuran and thiamethoxam, and particularly preferably includes dinotefuran.

Solubility of the agrochemical in water at 25° C. is preferably 100 ppm or more and more preferably 150 ppm or more.

B. Fertilizer

A term "fertilizer" refers to "that which is applied to soil for the purpose of bringing about a chemical change in the soil in order to provide nutrient to plants or contribute to cultivation of plants, or that which is applied to plants for the purpose of providing nutrients to plants" as defined in Fertilizers Regulations Act.

According to official standards defined on the basis of the Fertilizers Regulations Act, fertilizers are classified into nitrogenous fertilizers, phosphatic fertilizers, potassic fertilizers, organic fertilizers, compound fertilizers, calcareous fertilizers, siliceous fertilizers, magnesium fertilizers, manganese fertilizers, boracic fertilizers, trace element compound fertilizers, sludge fertilizers and fertilizers incorporating agricultural and other chemicals.

A term "soluble fertilizer" in the present description refers to, for example, a liquid or liquiform fertilizer in terms of official standards, such as a liquid nitrogen fertilizer, liquid phosphate fertilizer or liquiform compound fertilizer, or a liquid or liquiform fertilizer for which registration has been approved, such as a home garden-use mixed fertilizer or trace element compound fertilizer, the soluble fertilizer is not limited thereto, but rather refers to a fertilizer that can be diluted in water at an arbitrary ratio.

"Liquid or liquiform" indicates that a substance is a liquid or that a substance is in a liquid state. Although there is essentially no difference between the two, examples of liquid fertilizers include liquid potassium silicate fertilizers, liquid trace element compound fertilizers, liquid by-product nitrogen fertilizers and liquid phosphate fertilizers, while examples of liquiform fertilizers include liquiform nitrogen fertilizers and liquiform compound fertilizers.

The weight ratio of the guaranteed components of nitrogen (N), phosphorous (P) and potassium (K) according to the fertilizer and agrochemical formulation may be any weight ratio provided the formulation functions as a soluble fertilizer, and although there are no particular limitations thereon, specific examples thereof include a flat-type guaranteed component ratio in which the weight ratio of N:P:K is, for example, 1:1:1 (such as 5:5:5, 6:6:6, 7:7:7, 8:8:8 or 10:10:10), a crest-type guaranteed component ratio in which the weight ratio of P is high relative to N and K, such as that in which the weight ratio of N:P:K is, for example, 1:2:1 (such as 5:10:5), 1.2:2:1 (such as 6:10:5), 1:3:2 (such as 3:9:6) or 2:3:1 (such as 4:6:2), a trough-type guaranteed component ratio in which the weight ratio of P is low relative to N and K, such as that in which the weight ratio of N:P:K is, for example, 2:1:2 (such as 4:2:4), 2:1:3 (such as 4:2:6) or 3:1:2 (such as 6:2:4), a descending guaranteed component ratio in which the weight ratio of N is higher than the weight ratios of P and K, such as that in which the weight ratio of N:P:K is, for example, 2:1:1 (such as 6:3:3) or 3:2:1 (such as 9:6:3), and an ascending guaranteed component ratio in which the weight ratio of K is higher than the weight ratios of N and P, such as that in which the weight ratio of N:P:K is, for example, 1; 1; 2 (such as 3:3:6) or 1:2:3 (such as 3:6:9).

Moreover, any of the weight ratios of each of N, P and K may be 0 provided they are within the range of a formulation containing any one of fertilizer component selected from the group consisting of nitrogen (N), phosphorous (P), potassium (K), silicon (Si), magnesium (Mg), manganese (Mn), boron (B), calcium (Ca) and sulfur (S), or a formulation containing at least two of fertilizer components selected from the group consisting of nitrogen (N), phosphorous (P) and potassium (K).

A liquid or liquiform agrochemical and fertilizer formulation in which the weight ratio of N:P:K is 5:10:5 (1:2:1) or 6:10:5 (1.2:2:1) is particularly preferable.

Furthermore, the weight ratios of the guaranteed components are numerical values indicating the minimum required ratios of nitrogen (N), phosphorous (P) and potassium (K) contained in the prescribed fertilizer, and are not intended to limit those numerical values. Thus, fertilizers in which those weight ratios are ratios that are equal to or greater than those numerical values are eligible for use as fertilizers, and those fertilizers are included in the agrochemical and fertilizer formulation of the present invention.

A fertilizer used as a raw material may be a solid or liquid, and although it can be used in either form. When a fertilizer is a solid, a raw powder of the guaranteed components may be used as itself and a solid manure including a combination of a raw material may be used. It is advantageous that it be a liquid in order to efficiently produce a water-containing fertilizer and agrochemical liquid formulation.

C. Glycol Ether

A term "Glycol ether" refers to a compound in which one or both of the hydroxyl groups of a diol or condensate thereof are etherified, examples thereof include ethylene glycol monomethyl ether, ethylene glycol monoethyl ether, ethylene glycol monopropyl ether, ethylene glycol monoisopropyl ether, ethylene glycol monobutyl ether, ethylene glycol monoisobutyl ether, ethylene glycol mono-t-butyl ether, ethylene glycol mono-2-methylpentyl ether, ethylene glycol monohexyl ether, ethylene glycol mono-2-ethylhexyl ether, ethylene glycol monovinyl ether, ethylene glycol monoallyl ether, ethylene glycol monobenzyl ether, ethylene glycol monophenyl ether, ethylene glycol dimethyl ether, ethylene glycol diethyl ether, diethylene glycol monomethyl ether, diethylene glycol monoethyl ether, diethylene glycol monopropyl ether, diethylene glycol monoisopropyl ether, diethylene glycol monobutyl ether, diethylene glycol monoisobutyl ether, diethylene glycol monohexyl ether, diethylene glycol mono-2-ethylhexyl ether, diethylene glycol monoallyl ether, diethylene glycol monobenzyl ether, diethylene glycol monophenyl ether, diethylene glycol mono(methylphenyl) ether, diethylene glycol dimethyl ether, diethylene glycol methyl ethyl ether, diethylene glycol diethyl ether, diethylene glycol dibutyl ether, diethylene glycol divinyl ether, diethylene glycol ethyl vinyl ether, triethylene glycol monomethyl ether, triethylene glycol monoethyl ether, triethylene glycol monobutyl ether, triethylene glycol monovinyl ether, triethylene glycol dimethyl ether, tetraethylene glycol monophenyl ether, tetraethylene glycol diethyl ether, polyethylene glycol monomethyl ether, propylene glycol monomethyl ether, propylene glycol monoethyl ether, propylene glycol monopropyl ether, propylene glycol monoisopropyl ether, propylene glycol monobutyl ether, propylene glycol phenyl ether, propylene glycol mono(methylphenyl) ether, propylene glycol dimethyl ether, propylene glycol diethyl ether, propylene glycol dipropyl ether, propylene glycol diisopropyl ether, propylene glycol dibutyl ether, propylene glycol diisobutyl ether, propylene glycol diallyl ether, propylene glycol diphenyl ether, dipropylene glycol monomethyl ether, dipropylene glycol monoethyl ether, dipropylene glycol monopropyl ether, dipropylene glycol monobutyl ether, dipropylene glycol dimethyl ether, dipropylene glycol diethyl ether, dipropylene glycol dibutyl ether, dipropylene glycol diisobutyl ether, dipropylene glycol allyl ether, tripropylene glycol monomethyl ether, tripropylene glycol monoethyl ether, tripropylene glycol monobutyl ether, butylene glycol monomethyl ether, butylene glycol dimethyl ether and 3-methoxy-3-methyl-1-butanol, and the agrochemical and fertilizer formulation of the present invention preferably contains at least one of glycol ether selected from the group consisting thereof.

Among these, preferable examples of glycol ethers include ethylene glycol monomethyl ether, ethylene glycol monoethyl ether, ethylene glycol monopropyl ether, ethylene glycol monoisopropyl ether, ethylene glycol monobutyl ether, ethylene glycol monoisobutyl ether, ethylene glycol monoallyl ether, diethylene glycol monomethyl ether, diethylene glycol monoethyl ether, diethylene glycol monopropyl ether, diethylene glycol monoisopropyl ether, diethylene glycol monobutyl ether, diethylene glycol monoisobutyl ether, diethylene glycol monobenzyl ether, diethylene glycol dimethyl ether, diethylene glycol methyl ethyl ether, diethylene glycol diethyl ether, triethylene glycol monomethyl ether, triethylene glycol monobutyl ether, triethylene glycol dimethyl ether, polyethylene glycol monomethyl ether, propylene glycol monomethyl ether, propylene glycol monopropyl ether, propylene glycol monobutyl ether, dipropylene glycol monomethyl ether, dipropylene glycol monopropyl ether, tripropylene glycol monomethyl ether, butylene glycol monomethyl ether and 3-methoxy-3-methyl-1-butanol, and the agrochemical and fertilizer formulation of the present invention preferably contains at least one selected from the group consisting thereof.

Moreover, more preferable examples of glycol ethers include ethylene glycol monoisopropyl ether, ethylene glycol monobutyl ether, ethylene glycol monoisobutyl ether, ethylene glycol monoallyl ether, diethylene glycol monomethyl ether, diethylene glycol monoisopropyl ether, diethylene glycol monobutyl ether, diethylene glycol monoisobutyl ether, diethylene glycol monobenzyl ether, diethylene glycol dimethyl ether, diethylene glycol diethyl ether, diethylene glycol methyl ethyl ether, triethylene glycol monomethyl ether, triethylene glycol monobutyl ether, triethylene glycol dimethyl ether, polyethylene glycol monomethyl ether, propylene glycol monomethyl ether, propylene glycol monopropyl ether, dipropylene glycol monomethyl ether, tripropylene glycol monomethyl ether and 3-methoxy-3-methyl-1-butanol, and the agrochemical and fertilizer formulation of the present invention preferably contains at least one selected from the group consisting thereof.

Particularly preferable examples of glycol ethers include ethylene glycol monobutyl ether, ethylene glycol monoisobutyl ether, ethylene glycol monoallyl ether, diethylene glycol monobutyl ether, diethylene glycol monoisobutyl ether, diethylene glycol monobenzyl ether, propylene glycol monopropyl ether and 3-methoxy-3-methyl-1-butanol, and the agrochemical and fertilizer formulation of the present invention preferably contains at least one selected from the group consisting thereof. The agrochemical and fertilizer formulation of the present invention most preferably contains 3-methoxy-3-methyl-1-butanol for the glycol ether.

The term "homogeneous" refers to both quality and quantity being uniform regardless of the portion thereof.

The term "transparent" refers to allowing transmission of light without being turbid.

The term "liquiform" refers to adopting the form of a liquid, which is one of the three forms of matter, while a liquid refers to a substance capable of fluidly changing form to match a container in the same manner as a gas, but differs from a gas in that it maintains a nearly constant density without spreading throughout the container.

Thus, a "transparent, homogeneous liquiform fertilizer and agrochemical composition" refers to a liquid formulation that is qualitatively and quantitatively uniform in any portion of the fertilizer and agrochemical composition, light passes through the formulation when the formulation is irradiated with light, and the formulation per se is not turbid. The present agrochemical and fertilizer formulation is only required to be a solution that is not in a suspended state, and a translucent fertilizer and agrochemical composition is included therein. The particle diameter of particles contained in the transparent, homogeneous liquiform fertilizer and agrochemical composition according to the present invention is, for example, less than 100 nm, preferably less than 10 nm and more preferably less than 1 nm. Particle diameter can be measured using, for example, a particle size distribution analyzer.

Furthermore, although turbidity as determined by nephelometry can be used as an indicator of a suspended state, turbidity of a sample can be measured with a turbidity measuring instrument by comparing the agrochemical and fertilizer formulation with a standard series based on a reference solution. The turbidity of the present agrochemical and fertilizer formulation is preferably 2 units or less.

Next, an explanation is provided of a method for producing the fertilizer and agrochemical composition of the present invention.

The fertilizer and agrochemical composition can be produced by a known method such as dissolving an agrochemical (to also be referred to as the "agrochemical component"), a fertilizer (to also be referred to as the "fertilizer component") and a glycol ether in a solvent containing water, and if necessary, mixing in and dissolving a surfactant or other incorporated component and/or water.

There are no particular limitations on the water used, examples thereof include purified water, distilled water, ion exchange water, pure water, ultrapure water, sterile water and filtered water, and any water can be used.

There are no particular limitations on the order in which the agrochemical, fertilizer and glycol ether are dissolved in a solvent (such as water), and the order can be suitably selected corresponding to the properties of each component.

There are no particular limitations on the form of the agrochemical component and fertilizer component used as raw materials, and may be in the form of a solid or liquid. Namely, a solid agrochemical component and a solid fertilizer component may be separately dissolved in a solvent, or a solid agrochemical component and a solid fertilizer component may be mixed followed by dissolving the mixture in a solvent. There are no particular limitations on the order of dissolving them and the order can be suitably selected corresponding to the properties of each component. Any combination selected from, for example, the combination of a liquid agrochemical component, a solid fertilizer component and a glycol ether, the combination of a solid agrochemical component, a liquid fertilizer component and a glycol ether, the combination of a solid agrochemical component, a solid fertilizer component and a glycol ether, and the combination of a liquid agrochemical component, a liquid fertilizer component and a glycol ether can be used alone or after mixing in advance in order to dissolve in a solvent.

A desired fertilizer and agrochemical composition can be produced by dissolving each component of a mixture added to a solvent while suitably warming or heating and suitably stirring. When insoluble matter is present, filtration treatment may be performed as necessary using, for example, a microfiltration membrane, ultrafiltration membrane or reverse osmosis membrane. Filtration can be performed using any method. In consideration of the properties of the fertilizer and agrochemical composition of the present invention, it is normally advantageous to filter the mixture using a roughly 1 µm filter. There are no particular limitations on the temperature at which the fertilizer and agrochemical composition is prepared, and can be prepared at room temperature, while warming or while heating. The temperature of the mixed solvent during preparation is from 0° C. to the boiling point of the solvent, preferably 25° C. to 80° C., and particularly preferably 40° C. to 75° C.

In order to stably produce the fertilizer and agrochemical composition of the present invention, the fertilizer and agrochemical composition can be produced by adding a solid fertilizer component and/or a liquid fertilizer component to a aqueous composition that is prepared in advance and contains a glycol ether, an agrochemical and water. Therefore, an aqueous composition containing a glycol ether, an agrochemical and water, to also be referred to as a "premix", is a useful raw material for producing the fertilizer and agrochemical composition of the present invention.

Next, an explanation is provided of the aqueous composition containing a glycol ether, an agrochemical and water of the present invention. The aqueous composition containing a glycol ether, an agrochemical and water is characterized by including an agrochemical described in item "A. Agrochemical" and a glycol ether described in item "C. Glycol Ether" into water as solvent.

A preferable aqueous composition containing a glycol ether, an agrochemical and water includes at least one of glycol ether selected form the group consisting of ethylene glycol monobutyl ether, ethylene glycol monoisobutyl ether, ethylene glycol monoallyl ether, diethylene glycol monobutyl ether, diethylene glycol monoisobutyl ether, diethylene glycol monobenzyl ether, propylene glycol monopropyl ether and 3-methoxy-3-methyl-1-butanol, and further preferably includes 3-methoxy-3-methyl-1-butanol as the glycol ether, and includes at least one of neonicotinoid selected from the group consisting of acetamiprid, imidacloprid, clothianidin, dinotefuran, thiacloprid, thiamethoxam and nitenpyram, and further preferably includes dinotefuran as the agrochemical. The aqueous composition containing a glycol ether, an agrochemical and water can be also used as an agrochemical aqueous composition.

Examples of aqueous composition containing a glycol ether, an agrochemical and water include:

an aqueous solution of dinotefuran and ethylene glycol monoisopropyl ether, an aqueous solution of dinotefuran and ethylene glycol monobutyl ether, an aqueous solution of dinotefuran and ethylene glycol monoisobutyl ether, an aqueous solution of dinotefuran and ethylene glycol monoallyl ether, an aqueous solution of dinotefuran and ethylene glycol monomethyl ether, an aqueous solution of dinotefuran and diethylene glycol monoisopropyl ether, an aqueous solution of dinotefuran and diethylene glycol monobutyl ether, an aqueous solution of dinotefuran and diethylene glycol monoisobutyl ether, an aqueous solution of dinotefuran and diethylene glycol monobenzyl ether, an aqueous solution of dinotefuran and diethylene glycol dimethyl ether, an aqueous solution of dinotefuran and diethylene glycol diethyl ether, an aqueous solution of dinotefuran and diethylene glycol methyl ethyl ether, an aqueous solution of dinotefuran and triethylene glycol monomethyl ether, an aqueous solution of dinotefuran and triethylene glycol monobutyl ether, an aqueous solution of dinotefuran and triethylene glycol dimethyl ether, an aqueous solution of dinotefuran and polyethylene glycol monomethyl ether, an aqueous solution of dinotefuran and propylene glycol monomethyl ether, an aqueous solution of dinotefuran and propylene glycol monopropyl ether, an aqueous solution of dinotefuran and dipropylene glycol monomethyl ether, an aqueous solution of dinotefuran and tripropylene glycol monomethyl ether, an aqueous solution of dinotefuran and 3-methoxy-3-methyl-1-butanol;

an aqueous solution of imidacloprid and ethylene glycol monoisopropyl ether, an aqueous solution of imidacloprid and ethylene glycol monobutyl ether, an aqueous solution of imidacloprid and ethylene glycol monoisobutyl ether, an aqueous solution of imidacloprid and ethylene glycol monoallyl ether, an aqueous solution of imidacloprid and diethylene glycol monomethyl ether, an aqueous solution of imidacloprid and diethylene glycol monoisopropyl ether, an aqueous solution of imidacloprid and diethylene glycol monobutyl ether, an aqueous solution of imidacloprid and diethylene glycol monoisobutyl ether, an aqueous solution of imidacloprid and diethylene glycol monobenzyl ether, an aqueous solution of imidacloprid and diethylene glycol dimethyl ether, an aqueous solution of imidacloprid and diethylene glycol diethyl ether, an aqueous solution of imidacloprid and diethylene glycol methyl ethyl ether, an aqueous solution of imidacloprid and triethylene glycol monomethyl ether, an aqueous solution of imidacloprid and triethylene glycol monobutyl ether, an aqueous solution of imidacloprid and triethylene glycol dimethyl ether, an aqueous solution of imidacloprid and polyethylene glycol monomethyl ether, an aqueous solution of imidacloprid and propylene glycol monomethyl ether, an aqueous solution of imidacloprid and propylene glycol monopropyl ether, an aqueous solution of imidacloprid and dipropylene glycol monomethyl ether, an aqueous solution of imidacloprid and tripropylene glycol monomethyl ether, an aqueous solution of imidacloprid and 3-methoxy-3-methyl-1-butanol;

an aqueous solution of clothianidin and ethylene glycol monoisopropyl ether, an aqueous solution of clothianidin and ethylene glycol monobutyl ether, an aqueous solution of clothianidin and ethylene glycol monoisobutyl ether, an aqueous solution of clothianidin and ethylene glycol monoallyl ether, an aqueous solution of clothianidin and diethylene glycol monomethyl ether, an aqueous solution of clothianidin and diethylene glycol monoisopropyl ether, an aqueous solution of clothianidin and diethylene glycol monobutyl ether, an aqueous solution of clothianidin and diethylene glycol monoisobutyl ether, an aqueous solution of clothianidin and diethylene glycol monobenzyl ether, an aqueous solution of clothianidin and diethylene glycol dimethyl ether, an aqueous solution of clothianidin and diethylene glycol diethyl ether, an aqueous solution of clothianidin and diethylene glycol methyl ethyl ether, an aqueous solution of clothianidin and triethylene glycol monomethyl ether, an aqueous solution of clothianidin and triethylene glycol monobutyl ether, an aqueous solution of clothianidin and triethylene glycol dimethyl ether, an aqueous solution of clothianidin and propylene glycol monomethyl ether, an aqueous solution of clothianidin and propylene glycol monomethyl ether, an aqueous solution of clothianidin and propylene glycol monopropyl ether, an aqueous solution of clothianidin and dipropylene glycol monomethyl ether, an aqueous solution of clothianidin and tripropylene glycol monomethyl ether, an aqueous solution of clothianidin and 3-methoxy-3-methyl-1-butanol;

an aqueous solution of thiamethoxam and ethylene glycol monoisopropyl ether, an aqueous solution of thiamethoxam and ethylene glycol monobutyl ether, an aqueous solution of thiamethoxam and ethylene glycol monoisobutyl ether, an aqueous solution of thiamethoxam and ethylene glycol monoallyl ether, an aqueous solution of thiamethoxam and diethylene glycol monomethyl ether, an aqueous solution of thiamethoxam and diethylene glycol monoisopropyl ether, an aqueous solution of thiamethoxam and diethylene glycol monobutyl ether, an aqueous solution of thiamethoxam and diethylene glycol monoisobutyl ether, an aqueous solution of thiamethoxam and diethylene glycol monobenzyl ether, an aqueous solution of thiamethoxam and diethylene glycol dimethyl ether, an aqueous solution of thiamethoxam and diethylene glycol diethyl ether, an aqueous solution of thiamethoxam and diethylene glycol methyl ethyl ether, an aqueous solution of thiamethoxam and triethylene glycol monomethyl ether, an aqueous solution of thiamethoxam and triethylene glycol monobutyl ether, an aqueous solution of thiamethoxam and triethylene glycol dimethyl ether, an aqueous solution of thiamethoxam and polyethylene glycol monomethyl ether, an aqueous solution of thiamethoxam and propylene glycol monomethyl ether, an aqueous solution of thiamethoxam and propylene glycol monopropyl ether, an aqueous solution of thiamethoxam and dipropylene glycol monomethyl ether, an aqueous solution of thiamethoxam and tripropylene glycol monomethyl ether, an aqueous solution of thiamethoxam and 3-methoxy-3-methyl-1-butanol;

an aqueous solution of acetamiprid and ethylene glycol monoisopropyl ether, an aqueous solution of acetamiprid and ethylene glycol monobutyl ether, an aqueous solution of acetamiprid and ethylene glycol monoisobutyl ether, an aqueous solution of acetamiprid and ethylene glycol monoallyl ether, an aqueous solution of acetamiprid and diethylene glycol monomethyl ether, an aqueous solution of acetamiprid and diethylene glycol monoisopropyl ether, an aqueous solution of acetamiprid and diethylene glycol monobutyl ether, an aqueous solution of acetamiprid and diethylene glycol monoisobutyl ether, an aqueous solution of acetamiprid and diethylene glycol monobenzyl ether, an aqueous solution of acetamiprid and diethylene glycol dimethyl ether, an aqueous solution of acetamiprid and diethylene glycol diethyl ether, an aqueous solution of acetamiprid and diethylene glycol methyl ethyl ether, an aqueous solution of acetamiprid and triethylene glycol monomethyl ether, an aqueous solution of acetamiprid and triethylene glycol monobutyl ether, an aqueous solution of acetamiprid and triethylene glycol dimethyl ether, an aqueous solution of acetamiprid and polyethylene glycol monomethyl ether, an aqueous solution of acetamiprid and propylene glycol monomethyl ether, an aqueous solution of acetamiprid and propylene glycol monopropyl ether, an aqueous solution of acetamiprid and dipropylene glycol monomethyl ether, an aqueous solution of acetamiprid and tripropylene glycol monomethyl ether, an aqueous solution of acetamiprid and 3-methoxy-3-methyl-1-butanol;

an aqueous solution of thiacloprid and ethylene glycol monoisopropyl ether, an aqueous solution of thiacloprid and ethylene glycol monobutyl ether, an aqueous solution of thiacloprid and ethylene glycol monoisobutyl ether, an aqueous solution of thiacloprid and ethylene glycol monoallyl ether, an aqueous solution of thiacloprid and diethylene glycol monomethyl ether, an aqueous solution of thiacloprid and diethylene glycol monoisopropyl ether, an aqueous solution of thiacloprid and diethylene glycol monobutyl ether, an aqueous solution of thiacloprid and diethylene glycol monoisobutyl ether, an aqueous solution of thiacloprid and diethylene glycol monobenzyl ether, an aqueous solution of thiacloprid and diethylene glycol dimethyl ether, an aqueous solution of thiacloprid and diethylene glycol diethyl ether, an aqueous solution of thiacloprid and diethylene glycol methyl ethyl ether, an aqueous solution of thiacloprid and triethylene glycol monomethyl ether, an aqueous solution of thiacloprid and triethylene glycol monobutyl ether, an aqueous solution of thiacloprid and triethylene glycol dimethyl ether, an aqueous solution of thiacloprid and polyethylene glycol monomethyl ether, an aqueous solution of thiacloprid and propylene glycol monomethyl ether, an aqueous solution of thiacloprid and propylene glycol monopropyl ether, an aqueous solution of thiacloprid and dipropylene glycol monomethyl ether, an aqueous solution of thiacloprid and tripropylene glycol monomethyl ether, an aqueous solution of thiacloprid and 3-methoxy-3-methyl-1-butanol;

an aqueous solution of nitenpyram and ethylene glycol monoisopropyl ether, an aqueous solution of nitenpyram and ethylene glycol monobutyl ether, an aqueous solution of nitenpyram and ethylene glycol monoisobutyl ether, an aqueous solution of nitenpyram and ethylene glycol monoallyl ether, an aqueous solution of nitenpyram and diethylene glycol monomethyl ether, an aqueous solution of nitenpyram and diethylene glycol monoisopropyl ether, an aqueous solution of nitenpyram and diethylene glycol monobutyl ether, an aqueous solution of nitenpyram and diethylene glycol monoisobutyl ether, an aqueous solution of nitenpyram and diethylene glycol monobenzyl ether, an aqueous solution of nitenpyram and diethylene glycol dimethyl ether, an aqueous solution of nitenpyram and diethylene glycol diethyl ether, an aqueous solution of nitenpyram and diethylene glycol methyl ethyl ether, an aqueous solution of nitenpyram and triethylene glycol monomethyl ether, an aqueous solution of nitenpyram and triethylene glycol monobutyl ether, an aqueous solution of nitenpyram and triethylene glycol dimethyl ether, an aqueous solution of nitenpyram and polyethylene glycol monomethyl ether, an aqueous solution of nitenpyram and propylene glycol monomethyl ether, an aqueous solution of nitenpyram and propylene glycol monopropyl ether, an aqueous solution of nitenpyram and dipropylene glycol monomethyl ether, an aqueous solution of nitenpyram and tripropylene glycol monomethyl ether, an aqueous solution of nitenpyram and 3-methoxy-3-methyl-1-butanol; and the like.

Preferable examples of aqueous composition include:

an aqueous solution of dinotefuran and ethylene glycol monobutyl ether, an aqueous solution of dinotefuran and ethylene glycol monoisobutyl ether, an aqueous solution of dinotefuran and ethylene glycol monoallyl ether, an aqueous solution of dinotefuran and diethylene glycol monobutyl ether, an aqueous solution of dinotefuran and diethylene glycol monoisobutyl ether, an aqueous solution of dinotefuran and diethylene glycol monobenzyl ether, an aqueous solution of dinotefuran and propylene glycol monopropyl ether, an aqueous solution of dinotefuran and 3-methoxy-3-methyl-1-butanol;

an aqueous solution of imidacloprid and ethylene glycol monobutyl ether, an aqueous solution of imidacloprid and ethylene glycol monoisobutyl ether, an aqueous solution of imidacloprid and ethylene glycol monoallyl ether, an aqueous solution of imidacloprid and diethylene glycol monobutyl ether, an aqueous solution of imidacloprid and diethylene glycol monoisobutyl ether, an aqueous solution of imidacloprid and diethylene glycol monobenzyl ether, an aqueous solution of imidacloprid and propylene glycol monopropyl ether, an aqueous solution of imidacloprid and 3-methoxy-3-methyl-1-butanol;

an aqueous solution of clothianidin and ethylene glycol monobutyl ether, an aqueous solution of clothianidin and ethylene glycol monoisobutyl ether, an aqueous solution of clothianidin and ethylene glycol monoallyl ether, an aqueous solution of clothianidin and diethylene glycol monobutyl ether, an aqueous solution of clothianidin and diethylene glycol monoisobutyl ether, an aqueous solution of clothianidin and diethylene glycol monobenzyl ether, an aqueous solution of clothianidin and propylene glycol monopropyl ether, an aqueous solution of clothianidin and 3-methoxy-3-methyl-1-butanol;

an aqueous solution of thiamethoxam and ethylene glycol monobutyl ether, an aqueous solution of thiamethoxam and ethylene glycol monoisobutyl ether, an aqueous solution of thiamethoxam and ethylene glycol monoallyl ether, an aqueous solution of thiamethoxam and diethylene glycol monobutyl ether, an aqueous solution of thiamethoxam and diethylene glycol monoisobutyl ether, an aqueous solution of thiamethoxam and diethylene glycol monobenzyl ether, an aqueous solution of thiamethoxam and propylene glycol monopropyl ether, an aqueous solution of thiamethoxam and 3-methoxy-3-methyl-1-butanol;

an aqueous solution of acetamiprid and ethylene glycol monobutyl ether, an aqueous solution of acetamiprid and ethylene glycol monoisobutyl ether, an aqueous solution of acetamiprid and ethylene glycol monoallyl ether, an aqueous solution of acetamiprid and diethylene glycol monobutyl ether, an aqueous solution of acetamiprid and diethylene glycol monoisobutyl ether, an aqueous solution of acetamiprid and diethylene glycol monobenzyl ether, an aqueous solution of acetamiprid and propylene glycol monopropyl ether, an aqueous solution of acetamiprid and 3-methoxy-3-methyl-1-butanol; and the like. The most preferable aqueous composition is an aqueous solution of dinotefuran and 3-methoxy-3-methyl-1-butanol.

Next, an explanation is provided of a method for producing the aqueous composition containing a glycol ether, an agrochemical and water.

The aqueous composition containing a glycol ether, an agrochemical and water can be produced by a known method such as dissolving an agrochemical and a glycol ether in a solvent containing, for example, water, and if necessary, mixing in and dissolving a surfactant or other incorporated component and/or water.

There are no particular limitations on the water used, examples thereof include purified water, distilled water, ion exchange water, pure water, ultrapure water, sterile water and filtered water, and any water can be used.

There are no particular limitations on the order in which the agrochemical and glycol ether are dissolved in a solvent (such as water), and the order can be suitably selected corresponding to the properties of each component. There are no particular limitations on the form of the agrochemical component and the glycol ether used as raw materials, and may be in the form of a solid or liquid. Namely, a solid agrochemical component and a glycol ether may be separately dissolved in a solvent, or a solid agrochemical component may be dissolved in a solvent followed by dissolving the mixture and a glycol ether in a solvent. There are no particular limitations on the order of dissolving them and the order can be suitably selected corresponding to the properties of each component. Any combination selected from the combination of a liquid agrochemical component and a liquid glycol ether, the combination of a solid agrochemical component and a liquid glycol ether, the combination of a solid agrochemical component and a solid glycol ether, and the combination of a liquid agrochemical component and a solid glycol ether can be used alone or after mixing in advance in order to dissolve in a solvent.

An agrochemical component of any of an insecticide, fungicide, herbicide or plant growth regulator and the like can be incorporated as an agrochemical component in the fertilizer and agrochemical composition of the present invention.

Examples of plant growth regulators include hydrazide maleic hydrazide and salts thereof, abscisic acid, inabenfide, paclobutrazol, uniconazole, triapentenol and cycocel.

An agrochemical component that is any of a solid, semi-solid or liquid at normal temperature can be used for the agrochemical component. For example, two or more of agrochemicals having completely different target applications, in the manner of insecticides, fungicides or herbicides, can be incorporated.

Although there are no particular limitations on any or all of the agrochemical component, glycol ether and fertilizer component used provided they dissolve in a solvent, the range thereof is preferably 0.01% to 50% for the agrochemical component, 0.1% to 80% for the glycol ether and 0.1% to 95% for the total weight of the fertilizer component, more preferably 0.01% to 10% for the agrochemical component, 0.1% to 15% for the glycol ether and 0.1% to 90% for the total weight of the fertilizer component, even more preferably 0.03% to 5% for the agrochemical component, 3% to 10% for the glycol ether and 10% to 85% for the total weight of the fertilizer component, and most preferably 1% to 4% for the agrochemical component, 3% to 5% for the glycol ether and 50% to 85% for the total weight of the fertilizer component.

A solvent other than water and glycol ether can be incorporated as necessary in the fertilizer and agrochemical composition in addition to the aforementioned incorporated components. There are no particular limitations on the solvent provided it is a solvent that is miscible with water to a certain degree, and specific examples thereof include ether-based solvents such as tetrahydrofuran or 1,4-dioxane; nitrile-based solvents such as acetonitrile, propionitrile, butyronitrile, isobutyronitrile or malononitrile; alcohol-based solvents such as methanol, ethanol, propanol, isopropanol, 1-butanol, 2-butanol, isobutanol, t-butanol, allyl alcohol, ethylene glycol, 1,2-propanediol (propylene glycol), 1,3-propanediol, 1,2-butanediol, 1,3-butanediol, 1,4-butanediol or glycerin; ketone-based solvents such as acetone, methyl ethyl ketone or diethyl ketone; carbonate-based solvents such as dimethyl carbonate, diethyl carbonate, ethylene carbonate or propylene carbonate; ester-based solvents such as methyl formate, ethyl formate, methyl acetate, ethyl acetate, γ-butyrolactone, methyl lactate or ethyl lactate; amide-based solvents such as formamide, N,N-dimethylformamide, N,N-diethylformamide, N,N-dimethyl acetamide, N,N-diethylacetamide, N,N-dimethylpropionamide or N-methylpyrrolidone; carb amide-based solvents such as tetramethylurea or 1,3-dimethyl-2-imidazolidinone; sulfoxide-based solvents such as dimethylsulfoxide; sulfone-based solvents such as dimethylsulfone or sulfolane; and, amine-based solvents such as ammonia, methylamine, dimethylamine, diethylamine, triethylamine, isopropylamine, diisopropylamine, ethyldiisopropylamine, pyrrolidine, N-methylpyrrolidine, piperidine, N-methylpiperidine, morpholine, N-methylmorpholine, pyridine or ethanolamine. One of or two or more of these solvents may be added. The incorporated amount thereof is normally, for example, 0.1 part by weight to 50 parts by weight, preferably 0.1 part by weight to 30 parts by weight, and more preferably 0.1 part by weight to 10 parts by weight, in a fertilizer and agrochemical mixed liquid formulation.

A surfactant can be incorporated as necessary in the fertilizer and agrochemical composition in addition to the aforementioned incorporated components. There are no particular limitations on the surfactant provided it is normally used in the formulation of agrochemicals, and examples of surfactants that can be used include nonionic surfactants, anionic surfactants and cationic surfactants, preferably one of or two or more of a nonionic surfactant or anionic surfactant can be used, and more preferably one of or two or more of a nonionic surfactant can be used.

Specific examples of surfactants include nonionic surfactants such as polyoxyethylene alkyl allyl ethers, polyoxyethylene alkyl phenyl ethers, polyoxyethylene styryl phenyl ethers, polyoxyethylene-polyoxypropylene block copolymers, polyoxyethylene oleyl esters, polyoxyethylene fatty acid esters or sorbitan fatty acid esters;

anionic surfactants such as alkyl sulfate ester salts, alkylbenzene sulfonates, α-olefin sulfonates, alkyl succinates, polyoxyethylene alkyl aryl ether sulfates and phosphates, polyoxyethylene styryl phenyl ether sulfates and phosphates or alkyl imine salts; and, cationic surfactants such as primary to tertiary fatty amines, alkylammonium chlorides, tetraalkylammonium chlorides, trialkylbenzylammonium salts, alkylpyridinium salts or alkyl hydroxyethyl imidazolium salts, and compounded surfactants, such as an anionic surfactant and cationic surfactant, are also included. These surfactants may be used alone or two or more may be used in combination. The incorporated amount thereof is normally, for example, 0.1 part by weight to 70 parts by weight, preferably 0.1 part by weight to 30 parts by weight, and even more preferably 0.1 part by weight to 10 parts by weight, in the fertilizer and agrochemical mixed liquid formulation.

Additives can be incorporated as necessary in the fertilizer and agrochemical composition in addition to the aforementioned incorporated components. Additives such as lactic acid, hydrochloric acid, malic acid, sodium citrate, citric acid, disodium hydrogen phosphate, sodium dihydrogen phosphate, dipotassium hydrogen phosphate, potassium dihydrogen phosphate, phthalic acid, potassium hydrogen phthalate, sodium hydroxide, potassium hydroxide, sodium carbonate, potassium carbonate, succinic acid, sodium borate or N-ethylmorpholine can be incorporated as pH adjusters for improving stability of the agrochemical component, for example, at an incorporated ratio of 0.01 part by weight to 10 parts by weight, and preferably 0.05 parts by weight to 5 parts by weight, in the entire fertilizer and agrochemical composition. Antioxidants such as dibutylhydroxytoluene can be incorporated at an incorporation ratio of 0.001 part by weight to 1 part by weight, and preferably 0.005 parts by weight to 0.5 parts by weight. Ultraviolet absorbers such as 2-hydroxy-4-n-octoxybenzophenone can be incorporated at an incorporation ratio of 0.001 part by weight to 1 part by weight, and preferably 0.005 parts by weight to 0.5 parts by weight. Antifoaming agents such as acetylcholine-based antifoaming agents, silicone-based antifoaming agents, fluorine-based antifoaming agents or fatty acid-based antifoaming agents can be incorporated at an incorporation ratio of 0.001 part by weight to 5 parts by weight, and preferably 0.01 part by weight to 2 parts by weight. In addition, antimicrobial agents such as benzothiazole derivatives, sorbic acid, potassium sorbate, butyl p-hydroxybenzoate, glutaraldehyde, thiazuron or BNPK (2-bromo-2-nitropropane-1,3-diol) can be incorporated at an incorporation ratio of 0.01 part by weight to 5 parts by weight, and preferably 0.01 part by weight to 2 parts by weight. Moreover, although adjuvants described below such as colorants, crystallization preventive agents, thickeners, dispersants, chelating agents, effect expression promoting agents, composition homogenization accelerators or nitrification inhibitors may also each be added as necessary. These adjuvants are not limited to those exemplified here.

Examples of colorants include: azoic dye, azo dye, acridine, aniline dye, aniline black, indanthrene, eosin, congo red, dihydroindole, methylene blue, phenazine derivative dye, neutral red, phenolphthalein, fuchsin, fluorescein, para red, mauve, carotene; carotenoids such as xanthophylls, cryptoxanthin, zeaxanthin, fucoxanthin, lycopene, lutein; flavonoids such as flavones, flavanones, ants crawl, anthocyans, catechin; quinones such as melanin; porphyrin dye such as chlorophyll, chlorophyllide, bacteriochlorophyll, cytochrome, pheophorbide, Feo porphyrin, hemerythrin, hemoglobin, hemovanadin, hemocyanin, porphyrin, porphine, myoglobin; phycobilin-based pigments such as phycocyanin, phycobilin, phycoerythrin, phytochrome, biliverdin, bilirubin; alizarin, anthocyans, anthraquinone, indigo, urobilin, erythrocruorin, carthamin, hexane cretin Chin, curcumin, crocetin, chlorine, chlorocruorin, genistein, cochineal, Gosshiporu, commelinin, shikonin, Suterukopirin, tannin, Tsurashin, bixin, hypericin, Pin'nagurobin, brazilin, purpurin, betacyanin, berberine, Horubirin, mangosteen (mangostin), Morinjin, laminaran, leghemoglobin, litmus, rhodopsin, rhodoxanthin, Rodomachin, and in addition, for example, carbon black, red iron oxide, solvent Red 23, CI acid Blue 1 (C.I. Acid Blue 1), CI acid yellow 23 (C.I. acid yellow 23), and the like.

Examples of crystallization preventive agents include ethylene glycol, propylene glycol, glycerin, cyclodextrins, alkylene oxide adduct of glycerin, and the like.

Examples of thickeners include products available from Sansho Co., Ltd. or the like, for example, roast bean gum such as MEYPROLBG FLEUR™ M-200, guar gum such as SUPERGEL™ 200, guar gum derivatives such as JAGUAR™ C-13S, carrageenan such as WG-108, pectin such as YM-150-LJ™, xanthan gum, such as KELZAN™, gellan gum, such as KELCOGEL™ AFT, Daiyu Tan gum such as KELCO-CRETE™ DG, starches such as SB GUM-R™, dextrin such as MALTRIN(registered trademark) M040, cellulose derivatives (carboxymethyl cellulose derivatives) such as FINNFIX™, tara gum such as Supinogamu, and the like.

Examples of dispersants include products available from Kao Corporation or the like, for example, beta-naphthalenesulfonic acid formalin condensate sodium salt such as Demol™ N, special aromatic sulfonic acid-formalin condensate sodium salt such as, Demol™ SN-B, special polycarboxylic acid type polymeric surfactant such as Demol™ P, poly-carboxylic acid sodium salt such as Nopukosupasu™ 44-C, poly-carboxylic acid ammonium salts such as Nopukosupasu™ 5600, special poly-carboxylic acids ammonium salt such as SN Disperse Santo™ 5023, polyphosphate amino alcohol neutralization products such as SN dispersion Santo™ 2060, condensed naphthalene sulfonic acid ammonium salts such as Rome PWA-40™ and the like.

Examples of chelating agents include products available from Chelest Co., for example, EDTA (Ethylene Diamine Tetraacetic Acid), NTA (Nitrilo Triacetic Acid), DTPA (Diethylene Triamine Pentaacetic Acid), HEDTA (Hydroxyethyl Ethylene Diamine Triacetic Acid), TTHA (Triethylene Tetramine Hexaacetic Acid), PDTA (1,3-Propanediamine Tetraacetic Acid), DPTA-OH (1,3-Diamino-2-hydroxypropane Tetraacetic Acid), HIDA (Hydroxyethyl Imino Diacetic Acid), DHEG (Dihydroxyethyl Glycine), GEDTA (Glycol Ether Diamine Tetraacetic Acid), CMGA (Dicarboxymethyl Glutamic Acid), EDDS ((S,S)-Ethylene Diamine Disuccinic Acid), HEDP (Hydroxyethylidene Diphosphonic Acid), NTMP (Nitrilotris (Methylene Phosphonic Acid)), PBTC (Phosphonobutane Tricarboxylic Acid), EDTMP (Ethylene Diamine Tetra (Methylene Phosphonic Acid)), EDTA metal salts such as EDTA.Fe.Na.$H_2O$, DTPA metal salts such as DTPA.Fe.Na.H, PDTA metal salts such as PDTA.Fe.$NR_4H_2O$, $HOCH_2$ $(CHOH)_4COONa$ and the like.

Examples of effect expression promoting agents include ferrous sulfate, copper sulfate, zinc sulfate, ammonium molybdate and the like.

Examples of composition homogenization accelerators include gypsum, paraffin and mineral oil, cornstarch, zeolite and the like.

Examples of nitrification inhibitors include 2-amino-4-chloro-6-methyl-pyrimidine (AM), N-2,5-dichlorophenyl Saku Sina bromide acid (DCS), dicyandiamide, 1-amidino-2-thiourea (ASU) and the like.

The fertilizer and agrochemical composition can normally be used as a foliage treatment agent, seed treatment agent or directly sprayed agent. When producing an aqueous composition containing the fertilizer and agrochemical composition by diluting the prepared fertilizer and agrochemical composition, water such as agricultural water, industrial water, well water or tap water can be used in addition to the water described above provided it does not impair the function or performance of the fertilizer and agrochemical composition. Although the dilution factor used when preparing an aqueous composition can be suitably selected according to the target application, crop or soil and the like, the fertilizer and agrochemical composition can be diluted at a dilution factor of 10-fold to 5000-fold and preferably 50-fold to 2000-fold.

In the case of using for foliage treatment, although varying according to the type and content of the active ingredient, a diluted solution of the fertilizer and agrochemical composition typically diluted with water by about 100-fold to 5000-fold is sprayed onto foliage. In addition, a diluted solution of the fertilizer and agrochemical composition diluted with water by about 10-fold to 1000-fold may be sprayed from the air from a helicopter. In the case of using for seed treatment, seeds are soaked in a solution of the fertilizer and agrochemical composition diluted with water by about 10-fold to 100-fold, or seeds are sprayed with a solution of the fertilizer and agrochemical composition diluted with water by about 2-fold to 100-fold. In addition, in the case of spraying directly, although the fertilizer and agrochemical composition can be placed in a 100 mL to 1000 mL plastic bottle having a stoppered opening followed by transferring to a sprayer directly without diluting, the spraying method is not limited thereto. In addition, the applied amount and application time of the fertilizer and agrochemical composition or aqueous composition containing the fertilizer and agrochemical composition can be suitably determined corresponding to the agrochemical active ingredient incorporated therein.

The present invention may include an agrochemical formulation containing an agrochemical and a glycol ether. The agrochemical formulation preferably further includes water. An "agrochemical" used in the agrochemical formulation refers to a fungicide, insecticide, and other chemicals that include materials using that chemical as a raw material or material used for the purpose of control, which are used to control fungi, nematodes, mites, insects, rodents and other animals and plants or viruses (to be referred to as "pests") that damage agricultural crops that include trees and forestry products, to be collectively referred to as "agricultural crops", and plant growth regulator, germination inhibitor or other chemical used to enhance or inhibit the physiological functions of agricultural crops. There are no particular limitations on the chemical used for agriculture, any chemical can be used, and may be any of an insecticide, fungicide or herbicide. Specific examples of agrochemicals include: insecticides selected from the group consisting of carbamate acetylcholinesterase (AChE) inhibitors such as alanycarb, aldicarb, bendiocarb, benfuracarb, butocarboxim, butoxycarboxim, NAC (carbaryl), carbofuran, carbosulfan, ethiofencarb, BMPC (fenobucarb), formetanate, furathiocarb, MIPC (isoprocarb), methiocarb, methomyl, MTMC (metolcarb), oxamyl, pirimicarb, PHC (propoxur), thiodicarb, thiofanox, triazamate, trimethacarb, XMC or MPMC (xylylcarb), organophosphorous acetylcholinesterase (AChE) inhibitors such as acephate, azamethiphos, azinphos-ethyl, azinphos-methyl, cadusafos, chlorethoxyfos, CVP (chlorfenvinphos), chlormephos, chlorpyrifos, chlorpyrifos-methyl, coumaphos, CYAP (cyanophos), demeton-S-methyl, diazinon, DDVP (dichlorvos), dicrotophos, dimethoate, dimethylvinphos, ethyl thiomethone (disulfoton), EPN, ethion, ethoprophos, famphur, fenamiphos, MEP (fenitrothion), MPP (fenthion), fosthiazate, heptenophos, imicyafos, isofenphos, isopropyl-O-(methoxyamino-thiophosphoryl) salicylate, isoxathion, marathon (malathion), mecarbam, methamidophos, DMTP (methidathion), mevinphos, monocrotophos, BRP (naled), omethoate, oxydimethon-methyl, parathion, parathion-methyl, PAP (phenthoate), phorate, phosalone, PMP (phosmet), phosphamidon, phoxim, pirimphos-methyl, profenofos, propetamphos, prothiofos, pyraclofos, pyridaphenthion, quinalphos, sulfotep, tebupirimfos, temephos, terbufos, CVMP (tetrachlorvinphos), thiometon, triazophos, DEP (trichlorfon) or vamidothion, cyclodiene organochlorine GABA-gated chlorine ion channel blockers such as chlordane or benzoepin (endosulfan), phenylpyrazole (fiprole) GABA-gated chlorine ion channel blockers such as ethiprole and fipronil, pyrethroid and pyrethrin sodium channel modulators such as acrinathrin, allethrin (allethrin, d-cis-trans-, d-trans-isomers), bifenthrin, bioallethrin (bioallethrin, S-cyclopentenyl isomer), bioresmethrin, cycloprothrin, cyfluthrin (cyfluthrin, beta isomer), cyhalothrin (cyhalothrin, lamda-, gamma-isomers), cypermethrin (cypermethrin, alpha-, beta-, theta-, xi-isomers), cyphenothrin [(1R)-trans isomer], deltamethrin, empenthrin [(EZ)-(1R)-isomer], esfenvalerate, etofenprox, fenpropathrin, fenvalerate, flucythrinate, flumethrin, fluvalinate (tau-fluvalinate), halfenprox, imiprothrin, kadethrin, permethrin, phenothrin [(1R)-trans isomer], prallethrin, pyrethrin, resmethrin, silafluofen, tefluthrin, phthalthrin (tetramethrin), tetramethrin [(1R)-isomer], tralomethrin or transfluthrin, DDT and methoxychlor sodium channel modulators such as DDT or methoxychlor, neonicotinoid nicotinic acetylcholine receptor (nAChR) competitive modulators such as acetamiprid, clothianidin, dinotefuran, imidacloprid, nitenpyram, thiacloprid or thiamethoxam, nicotin nicotinic acetylcholine receptor (nAChR) competitive modulators such as nicotine sulfate (nicotine), sulfoximine nicotinic acetylcholine receptor (nAChR) competitive modulators such as sulfoxaflor, butenolide nicotinic acetylcholine receptor (nAChR) competitive modulators such as spinetoram or spinosad, avermectin and milbemycin glutamate-gated chloride channel (GluCl) allosteric modulators such as abamectin, emamectin benzoate, lepimectin or milbemectin, juvenile hormone mimics such as hydroprene, kinoprene, methoprene, fenoxycarb or pyriproxyfen, miscellaneous non-specific (multisite) inhibitors such as methyl bromide (methylbromide), alkyl halides other than methyl bromide, chloropicrin, cryolite (sodium aluminum fluoride), sulfuryl fluoride, borax, boric acid, disodium octaborate, sodium borate, sodium metaborate, tartar emetic, dazomet or metam, pyridine azomethine derivative chordotonal organ TRPV channel modulators such as pymetrozine or pyrifluquinazon, mite growth inhibitors such as clofentezine, hexythiazox, diflovidazin or etoxazole, microbial disruptors of insect midgut membranes such as *Bacillus thuringiensis* subspecies *israelensis*, *B.t.* subsp. *aizawai*, *B.t.* subsp. *kurstaki*, *B.t.* subsp. *tenebrionis*, B. t. proteins contained in crops (Cry1Ab, Cry1Ac, Cry1Fa, Cry1A.105, Cry2Ab, Vip3A, mCry3A, Cry3Ab, Cry3Bb and Cry34Ab1/Cry35Ab1) or *Bacillus sphaericus*, inhibitors of mitochondrial ATP synthase such as diafenthiuron, azocyclotin, tricyclohexyltin hydroxide (cyhexatin), fenbutatin oxide, BPPS (propargite) or tetradifon, uncouplers of oxidative phosphorylation via disruption of the proton gradient such as chlorfenapyr, DNOC or sulfluramid, nereistoxin analogue nicotinic acetylcholine receptor (nAChR) channel blockers such as bensultap, cartap, thiocyclam or thiosultap-sodium, benzoylurea inhibitors of chitin biosynthesis (type 0) such as bistrifluron, chlorfluazuron, diflubenzuron, flucycloxuron, flufenoxuron, hexaflumuron, lufenuron, novaluron, noviflumuron, teflubenzuron or triflumuron, inhibitors of chitin biosynthesis (type 1) such as buprofezin, molting disruptors (dipteran) such as cyromazine, diacylhydrazine ecdysone receptor agonists such as chromafenozide, halofenozide, methoxyfenozide or tebufenozide, octopamine receptor agonists such as amitraz, mitochondrial complex III electron transport inhibitors such as hydramethylnon, acequinocyl, fluacrypyrim or bifenazate, mitochondrial complex I electron transport inhibitors such as fenazaquin, fenpyroximate, pyrimidifen, pyridaben, tebufenpyrad, tolfenpyrad or derris (rotenone), voltage-dependent sodium channel blockers such as indoxacarb or metaflumizone, tetronic acid and tetramic acid derivative inhibitors of acetyl CoA carboxylase such as spirodiclofen, spiromesifen or spirotetramat, mitochondrial complex IV electron transport inhibitors such as aluminium phosphide, calcium phosphide, phosphine, zinc phosphide, calcium cyanide, potassium cyanide or sodium cyanide, mitochondrial complex II electron transport inhibitors such as cyenopyrafen, cyflumetofen or pyflubumide, diamide ryanodine receptor modulators such as chlorantraniliprole, cyantraniliprole or flubendiamide, flonicamid chordotonal organ modulators (undefined target site) such as flonicamid, natural enemy insect, mite and nematode-based biopesticides such as *Steinernema carpocapsae*, *Phytoseiulus persimilis*, *Amblyseius cucumeris*, *Aphidoletes aphidimyza*, *Orius sauteri*, *Orius strigicollis*, *Encarsia formosa*, *Diglyphus isaea*, *Aphidius colemani*, *Dacnusa sibirica Telenga* or *Neochrysocharis formosa*, microbial pesticides such as *Pasteuria penetrans*, *Bacillus thuringiensis* (BT), *Monacrosporium phymatopagum*, *Paecilomyces tenuipes*, *Beauveria brongniartii* or *Beauveria bassiana*, spiracle-blocking agrochemicals such as starch, reduced starch saccharification products, machine oil or sodium oleate, pheromone agents such as Konagakon Plus, Confuser G, Confuser N, Confuser V, Sukashiba-con, Nitolure (fall webworm), Hamaki-con N, Ferodin SL, Yotoukon H or Yotoukon S, azadirachtin, benzomate (benzoximate), phenisobromolate (bromopropylate), chinomethionat, quinoxaline (quinomethionate), sodium aluminum fluoride, kelthane (dicofol), pyridalyl, pyrifluquinazon, sulfur, ferric phosphate agents, metaaldehyde and 1,3-dichloropropene;

fungicides selected from the group consisting of acylanaline PA fungicides (phenylamides) such as benalaxyl, benalaxyl M, furalaxyl, metalaxyl or metalaxyl M, oxazolidinone PA fungicides (phenylamides) such as oxadixyl, butyrolactone PA fungicides (phenylamides) such as ofurace, hydroxyl(2-amino)pyrimidines such as bupirimate, dimethirimol or ethirimol, isoxazole heteroaromatics such as hydroxyisoxazole (hymexazol), isothiazolone heteroaromatics such as octhilinone, carboxylic acids such as oxolinic acid, benzimidazole MBC fungicides (methyl benzimidazole carbamate) such as benomyl, carbendazole (carbendazim), fuberidazole or thiabendazole, thiophanate MBC fungicides (methyl benzimidazole carbamate) such as thiophanate or thiophanate-methyl, N-phenyl carbamates such as diethofencarb, toluamide benzamides such as zoxamide, ethylamino-thiazole-carboxamide thiazole carboxamides such as ethaboxam, phenylureas such as pencycuron, pyridinylmethyl-benzamide benzamides such as fluopicolide, aminocyanoacrylate cyanoacrylates such as phenamacril, pyrimidineamines such as diflumetorim, pyrazole-5-carboxamide pyrazole MET 1 such as tolfenpyrad, phenyl-benzamide SDHI (succinate dehydrogenase inhibitors) such as benodanil, flutolanil or mepronil, phenyl-oxo-ethyl thiophene amide SDHI (succinate dehydrogenase inhibitors) such as isofetamid, pyridinyl-ethyl-benzamide SDHI (succinate dehydrogenase inhibitors) such as fluopyram, furan-carboxamide SDHI (succinate dehydrogenase inhibitors) such as fenfuram, oxathiin-carboxamide SDHI (succinate dehydrogenase inhibitors) such as carboxin or oxycarboxin, thiazole-carboxamide SDHI (succinate dehydrogenase inhibitors) such as thifluzamide, pyrazole-4-carboxamide SDHI (succinate dehydrogenase inhibitors) such as benzovindiflupyr, bixafen, fluxapyroxad, furametpyr, isopyrazam, penflufen, penthiopyrad or sedaxane, N-methoxy-(phenylethyl)-pyrazole-carboxamide SDHI (succinate dehydrogenase inhibitors) such as pydiflumetofen, pyridine-carboxamide SDHI (succinate dehydrogenase inhibitors) such as boscalid, methoxy-acrylate QoI-fungicides (Quinone outside inhibitors) such as azoxystrobin, coumoxystrobin, enoxastrobin, flufenoxystrobin, picoxystrobin or pyraoxystrobin, methoxy-acetamide QoI-fungicides (Quinone outside inhibitors) such as mandestrobin, methoxy-carbamate QoI-fungicides (Quinone outside inhibitors) such as pyraclostrobin, pyrametostrobin or triclopyricarb, oximino-acetate QoI-fungicides (Quinone outside inhibitors) such as kresoxim-methyl or trifloxystrobin, oximino-acetamide QoI-fungicides (Quinone outside inhibitors) such as dimoxystrobin, fenaminstrobin, metominostrobin or orysastrobin, oxazolidine-dione QoI-fungicides (Quinone outside inhibitors) such as famoxadone, dihydro-dioxazine QoI-fungicides (Quinone outside inhibitors) such as fluoxastrobin, imidazolinone QoI-fungicides (Quinone outside inhibitors) such as fenamidone, benzyl-carbamate QoI-fungicides (Quinone outside inhibitors) such as pyribencarb, cyano-imidazole QiI-fungicides (Quinone inside inhibitors) such as cyazofamid, sulfamoyl-triazole QiI-fungicides (Quinone inside inhibitors) such as amisulbrom, dinitrophenyl crotonates such as binapacryl, meptyldinocap or DPC (dinocap), 2,6-dinitroanilines such as fluazinam, tri-phenyl tin compound organic tin compounds such as fentin acetate, fentin chloride or fentin hydroxide, thiophene carboxamides such as silthiofam, triazolo-pyrimidylamine QoSI fungicides (Quinone outside inhibitors, stigmatellin binding type) such as ametoctradin, anilino-pyrimidine AP-fungicides (aniline-pyrimidines) such as cyprodinil, mepanipyrim or pyrimethanil, enopyranuronic acid antibiotics such as blasticidin-S, hexopyranosyl antibiotics such as kasugamycin, glucopyranosyl antibiotics such as streptomycin, tetracycline antibiotics such as oxytetracycline, allyloxyquinoline aza-naphthalenes such as quinoxyfen, quinazolinone aza-naphthalenes such as proquinazid, phenylpyrrole PP fungicides (phenylpyrroles) such as fenpiclonil or fludioxonil, dicarboximides such as chlozolinate, dimethachlone, iprodione, procymidone or vinclozolin, phosphoro-thiolates such as EDDP (edifenphos), IBP (iprobenfos) or pyrazophos, dithiolanes such as isoprothiolane, aromatic hydrocarbon AH-fungicides (aromatic hydrocarbons, including chlorophenyls and nitroanilines) such as biphenyl, chloroneb, CNA (dicloran), PCNB (quintozene), tecnazene or tolclofos-methyl, 1,2,4-thiadiazole heteroaromatics such as eclomezol (etridiazole), carbamates such as iodocarb, propamocarb or prothiocarb, microbial (*Bacillus* species): *Bacillus* species and the fungicidal lipopeptide produced such as *Bacillus subtilis* strain QST713, *Bacillus subtilis* strain FZB24, *Bacillus subtilis* strain MBI600 or *Bacillus subtilis* strain D747, terpene hydrocarbon and terpene alcohol plant extracts such as *Melaleuca alternifolia* (tea tree) extract, piperazine DMI fungicides (demethylation inhibitors, SBI: class I) such as triforine, pyridine DMI fungicides (demethylation inhibitors, SBI: class I) such as pyrifenox or pyrisoxazole, pyrimidine DMI fungicides (demethylation inhibitors, SBI: class I) such as fenarimol or nuarimol, imidazole DMI fungicides (demethylation inhibitors, SBI: class I) such as imazalil, oxpoconazole, pefurazoate, prochloraz or triflumizole, triazole DMI fungicides (demethylation inhibitors, SBI: class I) such as azaconazole, bitertanol, bromuconazole, cyproconazole, difenoconazole, diniconazole, epoxiconazole, etaconazole, fenbuconazole, fluquinconazole, flusilazole, flutriafol, hexaconazole, imibenconazole, ipconazole, metconazole, myclobutanil, penconazole, propiconazole, simeconazole, tebuconazole, tetraconazole, triadimefon, triadimenol or triticonazole, triazolinethione DMI fungicides (demethylation inhibitors, SBI: class I) such as prothioconazole, morpholine amines (morpholines, SBI: class II) such as aldimorph, dodemorph, fenpropimorph or tridemorph, piperidine amines (morpholines, SBI: class II) such as fenpropidin or piperalin, spiroketal-amine amines (morpholines, SBI: class II) such as spiroxamine, hydroxyanilides (SBI: class III) such as fenhexamid, amino-pyrazolinones (SBI: class III) such as fenpyrazamine, thiocarbamates (SBI: class IV) such as pyributicarb, allylamines (SBI: class IV) such as naftifine or terbinafine, peptidyl pyrimidine nucleotide polyoxines such as polyoxin, cinnamic acid amide CAA fungicides (carboxylic acid amides) such as dimethomorph, flumorph or pyrimorph, valinamide carbamate CAA fungicides (carboxylic acid amides) such as benthiavalicarb, iprovalicarb or valifenalate, mandelic acid amide CAA fungicides (carboxylic acid amides) such as mandipropamid, isobenzo-furanone MBI-R (melanin biosynthesis inhibitors-reductase) such as fthalide, pyrrolo-quinolinone MBI-R (melanin biosynthesis inhibitors-reductase) such as pyroquilon, triazolobenzo-thiazole MBI-R (melanin biosynthesis inhibitors-reductase) such as tricyclazole, cyclopropane-carboxamide MBI-D (melanin biosynthesis inhibitors-dehydratase) such as carpropamid, carboxamide MBI-D (melanin biosynthesis inhibitors-dehydratase) such as diclocymet, propionamide MBI-D (melanin biosynthesis inhibitors-dehydratase) such as fenoxanil, trifluoro-ethyl-carbamate MBI-P (melanin biosynthesis inhibitors-polyketide synthase) such as tolprocarb, benzo-thiadiazoles BTH such as acibenzolar-S-methyl, benzisothiazoles such as probenazole, thiadiazole carboxamides such as tiadinil or isotianil, natural polysaccharides such as laminarin, plant extracts such as *Reynoutria sachalinensis* extract, cyanoacetamide-oximes such as cymoxanil, ethyl phosphonate phosphonates such as fosetyl-Al, phosphonates such as phosphorous acid and salts, phthalamic acids such as teclofthalam, benzotriazines such as triazoxide, benzene-sulfonamides such as flusulfamide, pyridazinones such as diclomezine, thiocarbamates such as methasulfocarb, phenyl-acetamides such as cyflufenamid, benzophenone allyl-phenyl-ketones such as metrafenone, benzoylpyridine allyl-phenyl-ketones such as pyriofenone, guanidines such as guanidine (dodine), cyano-methylene-thiazolidine thiazolidines such as flutianil, pyrimidinone-hydrazones such as ferimzone, piperidinyl-thiazole-isoxazolines such as oxathiapiprolin, 4-quinoline-acetates such as tebufloquin, tetrazolyloximes such as picarbutrazox, glucopyranosyl antiobiotics such as validamycin, inorganic compounds such as copper (various salts) or sulfur, dithio-carbamates and analogues thereof such as ferbam, manzeb, maneb, metiram, propineb, thiuram, zineb or ziram, phthalimides such as captan, difoltan (captafol) or folpet, chloronitriles (phthalonitriles) such as TPN (chlorothalonil), sulfamides such as sulfene (dichlofluanid) or tolyfluanid, bis-guanidines such as guazatine or iminoctadine acetate/iminoctadine albesilate (iminoctadine), triazines such as triazine (anilazine), quinones (anthraquinones) such as dithianon, quinoxalines such as quinoxaline (quinomethionate), maleimides such as fluoroimide, polypeptides such as extract from the cotyledons of lupine plantlets ("PLAD"), physical inhibitors such as machine oil or organic oil, bicarbonate agents such as potassium bicarbonate, silver agents, organic copper agents such as 8-hydroxyquinoline copper, dodecylbenzenesulfonic acid bis(ethylenediamine) copper(II) complex salt or copper nonylphenol sulfonate, and soil disinfectants such as dazomet, chloropicrin, methyl isothiocyanate, carbam-sodium or ammonium N-methyldithiocarbaminate; and, herbicides selected from the group consisting of allyloxy propionate inhibitors of acetyl CoA carboxylase (ACCase) such as clodinafop-propargyl, cyhalofop-butyl, diclofop-methyl, fenoxaprop-P-ethyl, fluazifop P, haloxyfop-R-methyl, propaquizafop or quizalofop-p-ethyl, cyclohexanedione inhibitors of acetyl CoA carboxylase (ACCase) such as alloxydim, butroxydim, clethodim, cycloxydim, profoxydim, sethoxydim, tepraloxydim or tralkoxydim, phenylpyrazoline inhibitors of acetyl CoA carboxylase (ACCase) such as pinoxaden, sulfonylurea inhibitors of acetolactic acid synthase (ALS) (acetohydroxy acid synthase (AHAS) inhibitors) such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, flupyrsulfuron, foramsulfuron, halosulfuron-methyl, imazosulfuron, iodosulfuron, mesosulfuron, metsulfuron-methyl, nicosulfuron, oxasulfuron, primisulfuron, prosulfuron, pyrazosulfuron-ethyl, rimsulfuron, sulfometuron-methyl, sulfosulfuron, thifensulfuron-methyl, triasulfuron or tritosulfuron, imidazolinone inhibitors of acetolactic acid synthase (ALS) (acetohydroxy acid synthase (AHAS) inhibitors) such as imazapic, imazamethabenz methyl, imazamox, imazapyr, imazaquin or imazethapyr, triazolopyrimidine inhibitors of acetolactic acid synthase (ALS) (acetohydroxy acid synthase (AHAS) inhibitors) such as cloransulam-methyl, diclosulam, florasulam, flumetsulam, metosulam or penoxsulam, pyrimidinyl(thio)benzoate inhibitors of acetolactic acid synthase (ALS) (acetohydroxy acid synthase (AHAS) inhibitors) such as bispyribac-sodium, pyribenzoxim, pyriftalid, pyrithiobac-sodium or pyriminobac-methyl, sulfonylaminocarbonyl-triazolinone inhibitors of acetolactic acid synthase (ALS) (acetohydroxy acid synthase (AHAS) inhibitors) such as flucarbazone-sodium or propoxycarbazone-sodium, triazine inhibitors of photosynthesis at photochemical system II such as ametryn, atrazine, cyanazine, desmetryn, dimethametryn, prometon, prometryn, propazines (propazine), CAT (simazine), simetryn, terbumeton, terbuthylazine, terbutryn or trietazine, triazinone inhibitors of photosynthesis at photochemical system II such as hexazinone, metamitron or metribuzin, triazolinone inhibitors of photosynthesis at photochemical system II such as amicarbazone, uracil inhibitors of photosynthesis at photochemical system II such as bromacil, lenacil or terbacil, pyridazinone inhibitors of photosynthesis at photochemical system II such as PAC (chloridazon), phenyl-carbamate inhibitors of photosynthesis at photochemical system II such as desmedipham or phenmedipham, urea inhibitors of photosynthesis at photochemical system II such as chlorbromuron, chlorotoluron, chloroxuron, dimefuron, DCMU (diuron), ethidimuron, fenuron, fluometuron, isoproturon, isouron, linuron, methabenzthiazuron, metobromuron, metoxuron, monolinuron, neburon, siduron or tebuthiuron, amide inhibitors of photosynthesis at photochemical system II such as DCPA (propanil) or CMMP (pentanochlor), nitrile inhibitors of photosynthesis at photochemical system II such as bromofenoxim, bromoxynil or ioxynil, benzothiadiazinone inhibitors of photosynthesis at photochemical system II such as bentazon, phenyl-pyridazine inhibitors of photosynthesis at photochemical system II such as pyridate or pyridafol, bipyridylium photochemical system I electron diverting agents such as diquat or paraquat, diphenylether inhibitors of protoporphyrinogen oxidase (PPO) such as acifluorfen, bifenox, chlomethoxynil (chlomethoxyfen), fluoroglycofen-ethyl, fomesafen, halosafen, lactofen or oxyfluorfen, phenylpyrazole inhibitors of protoporphyrinogen oxidase (PPO) such as fluazolate or pyraflufen-ethyl, N-phenylphthalimide inhibitors of protoporphyrinogen oxidase (PPO) such as cinidon-ethyl, flumioxazin or flumiclorac-pentyl, thiadiazole inhibitors of protoporphyrinogen oxidase (PPO) such as fluthiacet-methyl or thidiazimin, oxadiazole inhibitors of protoporphyrinogen oxidase (PPO) such as oxadiazon or oxadiargyl, triazolinone inhibitors of protoporphyrinogen oxidase (PPO) such as azafenidin, carfentrazone-ethyl or sulfentrazone, oxazolidinedione inhibitors of protoporphyrinogen oxidase (PPO) such as pentoxazone, pyrimidindione inhibitors of protoporphyrinogen oxidase (PPO) such as benzfendizone or butafenacil, inhibitors of protoporphyrinogen oxidase (PPO) such as pyraclonil, profluazol or flufenpyr-ethyl, pyridazinone inhibitors of carotenoid biosynthesis at the phytoene desaturase step (PDS) such as norflurazon, pyridinecarboxamide inhibitors of carotenoid biosynthesis at the phytoene desaturase step (PDS) such as diflufenican or picolinafen, inhibitors of carotenoid biosynthesis at the phytoene desaturase step (PDS) such as beflubutamid, fluridone, flurochloridone or flurtamone, triketone inhibitors of 4-hydroxyphenyl-pyruvate-dioxygenase (4-HPPD) such as mesotrione or sulcotrione, isoxazole inhibitors of 4-hydroxyphenyl-pyruvate-dioxygenase (4-HPPD) such as isoxachlortole or isoxaflutole, pyrazole inhibitors of 4-hydroxyphenyl-pyruvate-dioxygenase (4-HPPD) such as benzofenap, pyrazolate (pyrazolynate) or pyrazoxyfen, inhibitors of 4-hydroxyphenyl-pyruvate-dioxygenase (4-HPPD) such as benzobicyclon, triazole inhibitors of carotenoid biosynthesis (unknown target site) such as ATA (amitrole), isoxazolidinone inhibitors of carotenoid biosynthesis (unknown target site) such as clomazone, urea inhibitors of carotenoid biosynthesis (unknown target site) such as fluometuron, diphenylether inhibitors of carotenoid biosynthesis (unknown target site) such as aclonifen, glycine inhibitors of EPSP synthase such as glyphosate or glyphosate-trimesium (sulfosate), phosphinic acid inhibitors of glutamine synthetase such as glufosinate or bialaphos (bilanafos), carbamate inhibitors of DHP (dihydropteroate) synthase such as asulam, dinitroaniline microtubule assembly inhibitors such as bethrodine (benfluralin), butralin, dinitramine, ethalfluralin, oryzalin, pendimethalin or trifluralin, phosphoramidate microtubule assembly inhibitors such as amiprophos-methyl or butamifos, pyridine microtubule assembly inhibitors such as dithiopyr or thiazopyr, benzamide microtubule assembly inhibitors such as propyzamide or tebutam, benzoic acid microtubule assembly inhibitors such as TCTP (chlorthal-dimethyl), carbamate inhibitors of mitosis/microtubule organisation such as IPC (chlorpropham), propham or carbetamide, chloroacetamide inhibitors of VLCFAs (inhibitors of cell division) such as acetochlor, alachlor, butachlor, dimethachlor, dimethenamid, metazachlor, metolachlor, pethoxamid, pretilachlor, propachlor, propisochlor or thenylchlor, acetamide inhibitors of VLCFAs (inhibitors of cell division) such as diphenamid, napropamide or naproanilide, oxyacetamide inhibitors of VLCFAs (inhibitors of cell division) such as flufenacet or mefenacet, tetrazolinone inhibitors of VLCFAs (inhibitors of cell division) such as fentrazamide, inhibitors of VLCFAs (inhibitors of cell division) such as anilofos, cafenstrole or piperophos, nitrile inhibitors of cell wall (cellulose) synthesis such as DBN (dichlobenil) or DCBN (chlorthiamid), benzamide inhibitors of cell wall (cellulose) synthesis such as isoxaben, triazolocarboxamide inhibitors of cell wall (cellulose) synthesis such as flupoxam, quinoline carboxylic acid inhibitors of cell wall (cellulose) synthesis such as quinclorac, dinitrophenol uncoupling (membrane disruption) agents such as DNOC, DNBP (dinoseb) or dinoterb, thiocarbamate inhibitors of lipid synthesis (non-ACCase inhibitors) such as butylate, hexylthiocarbam (cycloate), dimepiperate, EPTC, esprocarb, molinate, orbencarb, pebulate, prosulfocarb, benthiocarb (thiobencarb), tiocarbazil, triallate or vernolate, phosphorodithioate inhibitors of lipid synthesis (non-ACCase inhibitors) such as SAP (bensulide), benzofuran inhibitors of lipid synthesis (non-ACCase inhibitors) such as benfuresate or ethofumesate, chloro-carbonic-acid inhibitors of lipid synthesis (non-ACCase inhibitors) such as TCA, DPA (dalapon) or tetrapion (flupropanate), phenoxy-carboxylic-acid indole acetic acid-like agents (synthetic auxins) such as clomeprop, 2,4-PA (2,4-D), 2,4-DB, dichlorprop, MCPA, MCPB or MCPP (mecoprop), benzoic acid indole acetic acid-like agents (synthetic auxins) such as chloramben, MDBA (dicamba) or TCBA (2,3,6-TBA), pyridine carboxylic acid indole acetic acid-like agents (synthetic auxins) such as clopyralid, fluroxypyr, picloram or triclopyr, quinoline carboxylic acid indole acetic acid-like agents (synthetic auxins) such as quinclorac or quinmerac, indole acetic acid-like agents (synthetic auxins) such as benazolin-ethyl, phthalamate inhibitors of auxin transport such as NPA (naptalam), semicarbazone inhibitors of auxin transport such as diflufenzopyr-sodium, arylaminopropionic acids such as flamprop-M-methyl/isopropyl, pyrazoliums such as difenzoquat, organoarsenicals such as DMSA or MSMA, microorganisms such as *Xanthomonas campestris*, bromobutide, (chlor)-flurenol, cinmethylin, cumyluron, dazomet, dymron, methyl dymron, etobenzanid, fosamine, indanofan, carbam/carbam sodium salt, oxaziclomefone, oleic acid, pelargonic acid, pyributicarb, chlorates and cyanates.

Among these, the agrochemical is preferably an insecticide selected from the group consisting of carbamate acetylcholinesterase (AChE) inhibitors, organophosphorous acetylcholinesterase (AChE) inhibitors, phenylpyrazole (fiprole) GABA-gated chlorine ion channel blockers, pyrethroid and pyrethrin sodium channel modulators, sodium channel modulators, neonicotinoid nicotinic acetylcholine receptor (nAChR) competitive modulators, sulfoximine nicotinic acetylcholine receptor (nAChR) competitive modulators, spinosyn nicotinic acetylcholine receptor (nAChR) allosteric modulators, avermectin and milbemycin glutamate-gated chloride channel (GluCl) allosteric modulators, chordotonal organ TRPV channel modulators, uncouplers of oxidative phosphorylation via disruption of the proton gradient, mitochondrial complex III electron transport inhibitors, mitochondrial complex I electron transport inhibitors, voltage-dependent sodium channel blockers, tetronic acid and tetramic acid derivative inhibitors of acetyl CoA carboxylase, diamide ryanodine receptor modulators, flonicamid chordotonal organ modulators (undefined target site), quinoxaline (quinomethionate), pyridalyl and metaaldehyde; or, a fungicide selected from the group consisting of acylanaline PA fungicides (phenylamides), oxazolidinone PA fungicides (phenylamides), butyrolactone PA fungicides (phenyl amides), isoxazole heteroaromatics, benzimidazole MBC fungicides (methyl benzimidazole carbamate), N-phenyl carbamates, phenyl-benzamide SDHI (succinate dehydrogenase inhibitors), phenyl-oxo-ethyl thiophene amide SDHI (succinate dehydrogenase inhibitors), pyridinyl-ethyl-benzamide SDHI (succinate dehydrogenase inhibitors), furan-carboxamide SDHI (succinate dehydrogenase inhibitors), oxathiin-carboxamide SDHI (succinate dehydrogenase inhibitors), thiazole-carboxamide SDHI (succinate dehydrogenase inhibitors), pyrazole-4-carboxamide SDHI (succinate dehydrogenase inhibitors), N-methoxy-(phenyl-ethyl)-pyrazole-carboxamide SDHI (succinate dehydrogenase inhibitors), pyridine-carboxamide SDHI (succinate dehydrogenase inhibitors), methoxy-acrylate QoI-fungicides (Quinone outside inhibitors), methoxy-acetamide QoI-fungicides (Quinone outside inhibitors), methoxy-carbamate QoI-fungicides (Quinone outside inhibitors), oximino-acetate QoI-fungicides (Quinone outside inhibitors), oximino-acetamide QoI-fungicides (Quinone outside inhibitors), oxazolidine-dione QoI-fungicides (Quinone outside inhibitors), dihydro-dioxazine QoI-fungicides (Quinone outside inhibitors), imidazolinone QoI-fungicides (Quinone outside inhibitors), benzyl-carbamate QoI-fungicides (Quinone outside inhibitors), cyano-imidazole QiI-fungicides (Quinone inside inhibitors), sulfamoyl-triazole QiI-fungicides (Quinone inside inhibitors), 2,6-dinitroanilines, anilino-pyrimidine AP-fungicides (aniline-pyrimidines), phenylpyrrole PP-fungicides (phenylpyrroles), dicarboximides, piperazine DMI-fungicides (demethylation inhibitors, SBI: class I), pyridine DMI-fungicides (demethylation inhibitors, SBI: class I), pyrimidine DMI-fungicides (demethylation inhibitors, SBI: class I), imidazole DMI-fungicides (demethylation inhibitors, SBI: class I), triazole DMI-fungicides (demethylation inhibitors, SBI: class I), triazolinethione DMI-fungicides (demethylation inhibitors, SBI: class I), isobenzo-furanone MBI-R (melanin biosynthesis inhibitors-reductase), pyrrolo-quinolinone MBI-R (melanin biosynthesis inhibitors-reductase), triazolobenzo-thiazole MBI-R (melanin biosynthesis inhibitors-reductase), cyclopropane-carboxamide MBI-D (melanin biosynthesis inhibitors-dehydratase), carboxamide MBI-D (melanin biosynthesis inhibitors-dehydratase), propionamide MBI-D (melanin biosynthesis inhibitors-dehydratase), benzo-thiadiazoles BTH, benzisothiazoles, thiadiazole-carboxamides, cyanoacetamide-oximes, benzene-sulfonamides, pyridazinones, guanidines and quinoxalines.

The agrochemical is particularly preferably an insecticide selected from the group consisting of carbamate acetylcholinesterase (AChE) inhibitors, organophosphorous acetylcholinesterase (AChE) inhibitors, phenylpyrazole (fiprole) GABA-gated chlorine ion channel blockers, pyrethroid and pyrethrin sodium channel modulators, sodium channel modulators, neonicotinoid nicotinic acetylcholine receptor (nAChR) competitive modulators, sulfoximine nicotinic acetylcholine receptor (nAChR) competitive modulators, avermectin and milbemycin glutamate-gated chloride channel (GluCl) allosteric modulators, chordotonal organ TRPV channel modulators, uncouplers of oxidative phosphorylation via disruption of the proton gradient, diamide ryanodine receptor modulators, and flonicamid chordotonal organ modulators (undefined target site); or, a fungicide selected from the group consisting of isoxazole heteroaromatics, benzimidazole MBC fungicides (methyl benzimidazole carbamate), phenyl-benzamide SDHI (succinate dehydrogenase inhibitors), phenyl-oxo-ethyl thiophene amide SDHI (succinate dehydrogenase inhibitors), pyridinyl-ethyl-benzamide SDHI (succinate dehydrogenase inhibitors), furan-carboxamide SDHI (succinate dehydrogenase inhibitors), oxathiin-carboxamide SDHI (succinate dehydrogenase inhibitors), thiazole-carboxamide SDHI (succinate dehydrogenase inhibitors), pyrazole-4-carboxamide SDHI (succinate dehydrogenase inhibitors), N-methoxy-(phenyl-ethyl)-pyrazole-carboxamide SDHI (succinate dehydrogenase inhibitors), pyridine-carboxamide SDHI (succinate dehydrogenase inhibitors), methoxy-acrylate QoI-fungicides (Quinone outside inhibitors), methoxy-acetamide QoI-fungicides (Quinone outside inhibitors), methoxy-carbamate QoI-fungicides (Quinone outside inhibitors), oximino-acetate QoI-fungicides (Quinone outside inhibitors), oximino-acetamide QoI-fungicides (Quinone outside inhibitors), oxazolidine-dione QoI-fungicides (Quinone outside inhibitors), dihydro-dioxazine QoI-fungicides (Quinone outside inhibitors), imidazolinone QoI-fungicides (Quinone outside inhibitors), benzyl-carbamate QoI-fungicides (Quinone outside inhibitors), piperazine DMI-fungicides (demethylation inhibitors, SBI: class I), pyridine DMI-fungicides (demethylation inhibitors, SBI: class I), pyrimidine DMI-fungicides (demethylation inhibitors, SBI: class I), imidazole DMI-fungicides (demethylation inhibitors, SBI: class I), triazole DMI-fungicides (demethylation inhibitors, SBI: class I), triazolinethione DMI-fungicides (demethylation inhibitors, SBI: class I).

Specific examples of agrochemicals include: insecticides selected from the group consisting of aldicarb, bendiocarb, butocarboxim, butoxycarboxim, NAC (carbaryl), carbofuran, ethiofencarb, BPMC (fenobucarb), formetanate, MIPC (isoprocarb), methomyl, MTMC (metolcarb), oxamyl, pirimicarb, PHC (propoxur), thiofanox, triazamate, XMC, MPMC (xylylcarb), acephate, azamethiphos, cadusafos, CVP (chlorfenvinphos), demeton-S-methyl, DDVP (dichlorvos), dicrotophos, dimethoate, dimethylvinphos, ethoprophos, fenamiphos, fosthiazate, heptenophos, marathon (malathion), mecarbam, methamidophos, DMTP (methidathion), mevinphos, monocrotophos, omethoate, oxydemeton-methyl, phosphamidon, propetamphos, thiometon, DEP (trichlorfon), vamidothion, flumethrin, acetamiprid, clothianidin, dinotefuran, imidacloprid, nitenpyram, thiacloprid, thiamethoxam, nicotine sulfate (nicotine), sulfoxaflor, flupyradifurone, pyriproxyfen, methyl bromide (methylbromide), chloropicrin, sulfuryl fluoride, borax, tartar emetic, pymetrozine, flonicamid, BPPS (propargite), DNOC, cartap, thiocyclam, thiosultapsodium, cyromazine, hydrogen phosphide, hydrogen cyanide, azadirachtin, sodium aluminum fluoride, 1,3-dichloropropene, dicyclanil, ethylene dibromide, sabadilla and sulcofuron-sodium; and, fungicides selected from the group consisting of furalaxyl, metalaxyl, metalaxyl M, oxadixyl, ofurace, dimethirimol, hydroxyisoxazole (hymexazol), octhilinone, fenfuram, carboxin, oxycarboxin, furametpyr, metominostrobin, cyazofamid, pyrimethanil, kasugamycin, streptomycin, IBP (iprobenfos), echlomezol (etridiazole), propamocarb, prothiocarb, pyrifenox, imazalil, pefurazoate, triflumizole, flutriafol, myclobutanil, propiconazole, tetraconazole, fenpropidin, spiroxamine, validamycin, polyoxin, iprovalicarb, pyroquilon, cymoxanil, fosetyl, phosphorous acid and phosphites, flusulfamide, methasulfocarb, guanidine (dodine), ferimzone, potassium bicarbonate, ferbam, guazatine, iminoctadine acetate/iminoctadine albesilate (iminoctadine), copper sulfate, formaldehyde, 8-hydroxyquinoline sulfate, iodomethane, mercuric chloride, metam, methyl bromide, methyl isothiocyanate, mildiomycin, nabam, phenylmercuric acetate, 2-phenylphenol and polyoxin, and the agrochemical preferably contains at least one selected therefrom.

Among these, the agrochemical preferably includes at least one selected from the group consisting of acetamiprid, imidacloprid, clothianidin, dinotefuran, thiacloprid, thiamethoxam, nitenpyram and flonicamid, more preferably includes at least one selected from the group consisting of acetamiprid, imidacloprid, clothianidin, dinotefuran, thiacloprid, thiamethoxam and nitenpyram, even more preferably includes at least one selected from the group consisting of acetamiprid, imidacloprid, clothianidin, dinotefuran and thiamethoxam, and particularly preferably includes dinotefuran.

The agrochemical formulation can be produced by a known method such as dissolving an agrochemical (to also be referred to as the "agrochemical component") and glycol ether in a solvent containing water, and if necessary, mixing in and dissolving a surfactant or other incorporated component and/or water.

There are no particular limitations on the water used, examples thereof include purified water, distilled water, ion exchange water, pure water, ultrapure water, sterile water and filtered water, and any of water can be used.

There are no particular limitations on the order in which the agrochemical and glycol ether are dissolved in a solvent (such as water), and the order can be suitably selected corresponding to the properties of each component. There are no particular limitations on the form of the agrochemical component and fertilizer component used as raw materials, and may be in the form of a solid or liquid. Namely, a solid agrochemical component and a glycol ether may be separately dissolved in a solvent, or a solid agrochemical component may be mixed with a glycol ether followed by dissolving the mixture in a solvent. There are no particular limitations on the order of dissolving them and the order can be suitably selected corresponding to the properties of each component. Any combination selected from, for example, the combination of a liquid agrochemical component and a glycol ether and the combination of a solid agrochemical component and a glycol ether, can be used alone or after mixing in advance in order to dissolve in a solvent.

A desired agrochemical formulation can be produced by dissolving each component of a mixture added to a solvent while suitably warming or heating and suitably stirring. When insoluble matter is present, filtration treatment may be performed as necessary using, for example, a microfiltration membrane, ultrafiltration membrane or reverse osmosis membrane. Filtration can be performed using any method. In consideration of the properties of the agrochemical formulation, it is normally advantageous to filter the mixture using a roughly 1 μm filter. There are no particular limitations on the temperature at which the agrochemical formulation is prepared, and can be prepared at room temperature, while warming or while heating. The temperature of the mixed solvent during preparation is from 0° C. to the boiling point of the solvent, preferably 25° C. to 80° C., and particularly preferably 40° C. to 75° C.

A preferable agrochemical formulation containing a glycol ether, an agrochemical and water includes at least one of glycol ether selected form the group consisting of ethylene glycol monobutyl ether, ethylene glycol monoisobutyl ether, ethylene glycol monoallyl ether, diethylene glycol monobutyl ether, diethylene glycol monoisobutyl ether, diethylene glycol monobenzyl ether, propylene glycol monopropyl ether and 3-methoxy-3-methyl-1-butanol, and further preferably includes 3-methoxy-3-methyl-1-butanol as the glycol ether, and includes at least one of neonicotinoid selected from the group consisting of acetamiprid, imidacloprid, clothianidin, dinotefuran, thiacloprid, thiamethoxam and nitenpyram, and further preferably includes dinotefuran as the agrochemical.

Examples of agrochemical formulation containing a glycol ether, an agrochemical and water include:

an aqueous solution of dinotefuran and ethylene glycol monoisopropyl ether, an aqueous solution of dinotefuran and ethylene glycol monobutyl ether, an aqueous solution of dinotefuran and ethylene glycol monoisobutyl ether, an aqueous solution of dinotefuran and ethylene glycol monoallyl ether, an aqueous solution of dinotefuran and ethylene glycol monomethyl ether, an aqueous solution of dinotefuran and diethylene glycol monoisopropyl ether, an aqueous solution of dinotefuran and diethylene glycol monobutyl ether, an aqueous solution of dinotefuran and diethylene glycol monoisobutyl ether, an aqueous solution of dinotefuran and diethylene glycol monobenzyl ether, an aqueous solution of dinotefuran and diethylene glycol dimethyl ether, an aqueous solution of dinotefuran and diethylene glycol diethyl ether, an aqueous solution of dinotefuran and diethylene glycol methyl ethyl ether, an aqueous solution of dinotefuran and triethylene glycol monomethyl ether, an aqueous solution of dinotefuran and triethylene glycol monobutyl ether, an aqueous solution of dinotefuran and triethylene glycol dimethyl ether, an aqueous solution of dinotefuran and polyethylene glycol monomethyl ether, an aqueous solution of dinotefuran and propylene glycol monomethyl ether, an aqueous solution of dinotefuran and propylene glycol monopropyl ether, an aqueous solution of dinotefuran and dipropylene glycol monomethyl ether, an aqueous solution of dinotefuran and tripropylene glycol monomethyl ether, an aqueous solution of dinotefuran and 3-methoxy-3-methyl-1-butanol;

an aqueous solution of imidacloprid and ethylene glycol monoisopropyl ether, an aqueous solution of imidacloprid and ethylene glycol monobutyl ether, an aqueous solution of imidacloprid and ethylene glycol monoisobutyl ether, an aqueous solution of imidacloprid and ethylene glycol monoallyl ether, an aqueous solution of imidacloprid and diethylene glycol monomethyl ether, an aqueous solution of imidacloprid and diethylene glycol monoisopropyl ether, an aqueous solution of imidacloprid and diethylene glycol monobutyl ether, an aqueous solution of imidacloprid and diethylene glycol monoisobutyl ether, an aqueous solution of imidacloprid and diethylene glycol monobenzyl ether, an aqueous solution of imidacloprid and diethylene glycol dimethyl ether, an aqueous solution of imidacloprid and diethylene glycol diethyl ether, an aqueous solution of imidacloprid and diethylene glycol methyl ethyl ether, an aqueous solution of imidacloprid and triethylene glycol monomethyl ether, an aqueous solution of imidacloprid and triethylene glycol monobutyl ether, an aqueous solution of imidacloprid and triethylene glycol dimethyl ether, an aqueous solution of imidacloprid and polyethylene glycol monomethyl ether, an aqueous solution of imidacloprid and propylene glycol monomethyl ether, an aqueous solution of imidacloprid and propylene glycol monopropyl ether, an aqueous solution of imidacloprid and dipropylene glycol monomethyl ether, an aqueous solution of imidacloprid and tripropylene glycol monomethyl ether, an aqueous solution of imidacloprid and 3-methoxy-3-methyl-1-butanol;

an aqueous solution of clothianidin and ethylene glycol monoisopropyl ether, an aqueous solution of clothianidin and ethylene glycol monobutyl ether, an aqueous solution of clothianidin and ethylene glycol monoisobutyl ether, an aqueous solution of clothianidin and ethylene glycol monoallyl ether, an aqueous solution of clothianidin and diethylene glycol monomethyl ether, an aqueous solution of clothianidin and diethylene glycol monoisopropyl ether, an aqueous solution of clothianidin and diethylene glycol monobutyl ether, an aqueous solution of clothianidin and diethylene glycol monoisobutyl ether, an aqueous solution of clothianidin and diethylene glycol monobenzyl ether, an aqueous solution of clothianidin and diethylene glycol dimethyl ether, an aqueous solution of clothianidin and diethylene glycol diethyl ether, an aqueous solution of clothianidin and diethylene glycol methyl ethyl ether, an aqueous solution of clothianidin and triethylene glycol monomethyl ether, an aqueous solution of clothianidin and triethylene glycol monobutyl ether, an aqueous solution of clothianidin and triethylene glycol dimethyl ether, an aqueous solution of clothianidin and propylene glycol monomethyl ether, an aqueous solution of clothianidin and propylene glycol monomethyl ether, an aqueous solution of clothianidin and propylene glycol monopropyl ether, an aqueous solution of clothianidin and dipropylene glycol monomethyl ether, an aqueous solution of clothianidin and tripropylene glycol monomethyl ether, an aqueous solution of clothianidin and 3-methoxy-3-methyl-1-butanol;

an aqueous solution of thiamethoxam and ethylene glycol monoisopropyl ether, an aqueous solution of thiamethoxam and ethylene glycol monobutyl ether, an aqueous solution of thiamethoxam and ethylene glycol monoisobutyl ether, an aqueous solution of thiamethoxam and ethylene glycol monoallyl ether, an aqueous solution of thiamethoxam and diethylene glycol monomethyl ether, an aqueous solution of thiamethoxam and diethylene glycol monoisopropyl ether, an aqueous solution of thiamethoxam and diethylene glycol monobutyl ether, an aqueous solution of thiamethoxam and diethylene glycol monoisobutyl ether, an aqueous solution of thiamethoxam and diethylene glycol monobenzyl ether, an aqueous solution of thiamethoxam and diethylene glycol dimethyl ether, an aqueous solution of thiamethoxam and diethylene glycol diethyl ether, an aqueous solution of thiamethoxam and diethylene glycol methyl ethyl ether, an aqueous solution of thiamethoxam and triethylene glycol monomethyl ether, an aqueous solution of thiamethoxam and triethylene glycol monobutyl ether, an aqueous solution of thiamethoxam and triethylene glycol dimethyl ether, an aqueous solution of thiamethoxam and polyethylene glycol monomethyl ether, an aqueous solution of thiamethoxam and propylene glycol monomethyl ether, an aqueous solution of thiamethoxam and propylene glycol monopropyl ether, an aqueous solution of thiamethoxam and dipropylene glycol monomethyl ether, an aqueous solution of thiamethoxam and tripropylene glycol monomethyl ether, an aqueous solution of thiamethoxam and 3-methoxy-3-methyl-1-butanol;

an aqueous solution of acetamiprid and ethylene glycol monoisopropyl ether, an aqueous solution of acetamiprid and ethylene glycol monobutyl ether, an aqueous solution of acetamiprid and ethylene glycol monoisobutyl ether, an aqueous solution of acetamiprid and ethylene glycol monoallyl ether, an aqueous solution of acetamiprid and diethylene glycol monomethyl ether, an aqueous solution of acetamiprid and diethylene glycol monoisopropyl ether, an aqueous solution of acetamiprid and diethylene glycol monobutyl ether, an aqueous solution of acetamiprid and diethylene glycol monoisobutyl ether, an aqueous solution of acetamiprid and diethylene glycol monobenzyl ether, an aqueous solution of acetamiprid and diethylene glycol dimethyl ether, an aqueous solution of acetamiprid and diethylene glycol diethyl ether, an aqueous solution of acetamiprid and diethylene glycol methyl ethyl ether, an aqueous solution of acetamiprid and triethylene glycol monomethyl ether, an aqueous solution of acetamiprid and triethylene glycol monobutyl ether, an aqueous solution of acetamiprid and triethylene glycol dimethyl ether, an aqueous solution of acetamiprid and polyethylene glycol monomethyl ether, an aqueous solution of acetamiprid and propylene glycol monomethyl ether, an aqueous solution of acetamiprid and propylene glycol monopropyl ether, an aqueous solution of acetamiprid and dipropylene glycol monomethyl ether, an aqueous solution of acetamiprid and tripropylene glycol monomethyl ether, an aqueous solution of acetamiprid and 3-methoxy-3-methyl-1-butanol;

an aqueous solution of thiacloprid and ethylene glycol monoisopropyl ether, an aqueous solution of thiacloprid and ethylene glycol monobutyl ether, an aqueous solution of thiacloprid and ethylene glycol monoisobutyl ether, an aqueous solution of thiacloprid and ethylene glycol monoallyl ether, an aqueous solution of thiacloprid and diethylene glycol monomethyl ether, an aqueous solution of thiacloprid and diethylene glycol monoisopropyl ether, an aqueous solution of thiacloprid and diethylene glycol monobutyl ether, an aqueous solution of thiacloprid and diethylene glycol monoisobutyl ether, an aqueous solution of thiacloprid and diethylene glycol monobenzyl ether, an aqueous solution of thiacloprid and diethylene glycol dimethyl ether, an aqueous solution of thiacloprid and diethylene glycol diethyl ether, an aqueous solution of thiacloprid and diethylene glycol methyl ethyl ether, an aqueous solution of thiacloprid and triethylene glycol monomethyl ether, an aqueous solution of thiacloprid and triethylene glycol monobutyl ether, an aqueous solution of thiacloprid and triethylene glycol dimethyl ether, an aqueous solution of thiacloprid and polyethylene glycol monomethyl ether, an aqueous solution of thiacloprid and propylene glycol monomethyl ether, an aqueous solution of thiacloprid and propylene glycol monopropyl ether, an aqueous solution of thiacloprid and dipropylene glycol monomethyl ether, an aqueous solution of thiacloprid and tripropylene glycol monomethyl ether, an aqueous solution of thiacloprid and 3-methoxy-3-methyl-1-butanol;

an aqueous solution of nitenpyram and ethylene glycol monoisopropyl ether, an aqueous solution of nitenpyram and ethylene glycol monobutyl ether, an aqueous solution of nitenpyram and ethylene glycol monoisobutyl ether, an aqueous solution of nitenpyram and ethylene glycol monoallyl ether, an aqueous solution of nitenpyram and diethylene glycol monomethyl ether, an aqueous solution of nitenpyram and diethylene glycol monoisopropyl ether, an aqueous solution of nitenpyram and diethylene glycol monobutyl ether, an aqueous solution of nitenpyram and diethylene glycol monoisobutyl ether, an aqueous solution of nitenpyram and diethylene glycol monobenzyl ether, an aqueous solution of nitenpyram and diethylene glycol dimethyl ether, an aqueous solution of nitenpyram and diethylene glycol diethyl ether, an aqueous solution of nitenpyram and diethylene glycol methyl ethyl ether, an aqueous solution of nitenpyram and triethylene glycol monomethyl ether, an aqueous solution of nitenpyram and triethylene glycol monobutyl ether, an aqueous solution of nitenpyram and triethylene glycol dimethyl ether, an aqueous solution of nitenpyram and polyethylene glycol monomethyl ether, an aqueous solution of nitenpyram and propylene glycol monomethyl ether, an aqueous solution of nitenpyram and propylene glycol monopropyl ether, an aqueous solution of nitenpyram and dipropylene glycol monomethyl ether, an aqueous solution of nitenpyram and tripropylene glycol monomethyl ether, an aqueous solution of nitenpyram and 3-methoxy-3-methyl-1-butanol; and the like.

Preferable examples of agrochemical formulation include:

an aqueous solution of dinotefuran and ethylene glycol monobutyl ether, an aqueous solution of dinotefuran and ethylene glycol monoisobutyl ether, an aqueous solution of dinotefuran and ethylene glycol monoallyl ether, an aqueous solution of dinotefuran and diethylene glycol monobutyl ether, an aqueous solution of dinotefuran and diethylene glycol monoisobutyl ether, an aqueous solution of dinotefuran and diethylene glycol monobenzyl ether, an aqueous solution of dinotefuran and propylene glycol monopropyl ether, an aqueous solution of dinotefuran and 3-methoxy-3-methyl-1-butanol;

an aqueous solution of imidacloprid and ethylene glycol monobutyl ether, an aqueous solution of imidacloprid and ethylene glycol monoisobutyl ether, an aqueous solution of imidacloprid and ethylene glycol monoallyl ether, an aqueous solution of imidacloprid and diethylene glycol monobutyl ether, an aqueous solution of imidacloprid and diethylene glycol monoisobutyl ether, an aqueous solution of imidacloprid and diethylene glycol monobenzyl ether, an aqueous solution of imidacloprid and propylene glycol monopropyl ether, an aqueous solution of imidacloprid and 3-methoxy-3-methyl-1-butanol;

an aqueous solution of clothianidin and ethylene glycol monobutyl ether, an aqueous solution of clothianidin and ethylene glycol monoisobutyl ether, an aqueous solution of clothianidin and ethylene glycol monoallyl ether, an aqueous solution of clothianidin and diethylene glycol monobutyl ether, an aqueous solution of clothianidin and diethylene glycol monoisobutyl ether, an aqueous solution of clothianidin and diethylene glycol monobenzyl ether, an aqueous solution of clothianidin and propylene glycol monopropyl ether, an aqueous solution of clothianidin and 3-methoxy-3-methyl-1-butanol;

an aqueous solution of thiamethoxam and ethylene glycol monobutyl ether, an aqueous solution of thiamethoxam and ethylene glycol monoisobutyl ether, an aqueous solution of thiamethoxam and ethylene glycol monoallyl ether, an aqueous solution of thiamethoxam and diethylene glycol monobutyl ether, an aqueous solution of thiamethoxam and diethylene glycol monoisobutyl ether, an aqueous solution of thiamethoxam and diethylene glycol monobenzyl ether, an aqueous solution of thiamethoxam and propylene glycol monopropyl ether, an aqueous solution of thiamethoxam and 3-methoxy-3-methyl-1-butanol;

an aqueous solution of acetamiprid and ethylene glycol monobutyl ether, an aqueous solution of acetamiprid and ethylene glycol monoisobutyl ether, an aqueous solution of acetamiprid and ethylene glycol monoallyl ether, an aqueous solution of acetamiprid and diethylene glycol monobutyl ether, an aqueous solution of acetamiprid and diethylene glycol monoisobutyl ether, an aqueous solution of acetamiprid and diethylene glycol monobenzyl ether, an aqueous solution of acetamiprid and propylene glycol monopropyl ether, an aqueous solution of acetamiprid and 3-methoxy-3-methyl-1-butanol; and the like.

The most preferable agrochemical formulation is an aqueous solution of dinotefuran and 3-methoxy-3-methyl-1-butanol.

Next, an explanation is provided of a method for producing the agrochemical formulation containing a glycol ether, an agrochemical and water.

The agrochemical formulation containing a glycol ether, an agrochemical and water can be produced by a known method such as dissolving an agrochemical and a glycol ether in a solvent containing, for example, water, and if necessary, mixing in and dissolving a surfactant or other incorporated component and/or water.

There are no particular limitations on the water used, examples thereof include purified water, distilled water, ion exchange water, pure water, ultrapure water, sterile water and filtered water, and any water can be used.

There are no particular limitations on the order in which the agrochemical and glycol ether are dissolved in a solvent (such as water), and the order can be suitably selected corresponding to the properties of each component. There are no particular limitations on the form of the agrochemical component and the glycol ether used as raw materials, and may be in the form of a solid or liquid. Namely, a solid agrochemical component and a glycol ether may be separately dissolved in a solvent, or a solid agrochemical component may be dissolved in a solvent followed by dissolving the mixture and a glycol ether in a solvent. There are no particular limitations on the order of dissolving them and the order can be suitably selected corresponding to the properties of each component. Any combination selected from the combination of a liquid agrochemical component and a liquid glycol ether, the combination of a solid agrochemical component and a liquid glycol ether, the combination of a solid agrochemical component and a solid glycol ether, and the combination of a liquid agrochemical component and a solid glycol ether can be used alone or after mixing in advance in order to dissolve in a solvent.

An agrochemical component of any of an insecticide, fungicide, herbicide or plant growth regulator and the like can be incorporated as an agrochemical component in the agrochemical formulation.

Examples of plant growth regulators include hydrazide maleic hydrazide and salts thereof, abscisic acid, inabenfide, paclobutrazol, uniconazole, triapentenol and cycocel.

An agrochemical component that is any of a solid, semi-solid or liquid at normal temperature can be used for the agrochemical component. For example, two or more of agrochemicals having completely different target applications, in the manner of insecticides, fungicides or herbicides, can be incorporated.

Although there are no particular limitations on any or all of the agrochemical component and glycol ether used provided they dissolve in a solvent, the range thereof is preferably 0.01% to 50% for the agrochemical component and 0.1% to 80% for the glycol ether, more preferably 0.01% to 20% for the agrochemical component and 0.1% to 30% for the glycol ether, even more preferably 0.03% to 10% for the agrochemical component and 3% to 20% for the glycol ether, and most preferably 1% to 8% for the agrochemical component and 3% to 10% for the glycol ether.

A solvent other than water can be incorporated as necessary in the agrochemical formulation in addition to the aforementioned incorporated components. There are no particular limitations on the solvent provided it is a solvent that is miscible with water to a certain degree, and specific examples thereof include ether-based solvents such as tetrahydrofuran or 1,4-dioxane; nitrile-based solvents such as acetonitrile, propionitrile, butyronitrile, isobutyronitrile or malononitrile; alcohol-based solvents such as methanol, ethanol, propanol, isopropanol, 1-butanol, 2-butanol, isobutanol, t-butanol, allyl alcohol, ethylene glycol, 1,2-propanediol (propylene glycol), 1,3-propanediol, 1,2-butanediol, 1,3-butanediol, 1,4-butanediol or glycerin; ketone-based solvents such as acetone, methyl ethyl ketone or diethyl ketone; carbonate-based solvents such as dimethyl carbonate, diethyl carbonate, ethylene carbonate or propylene carbonate; ester-based solvents such as methyl formate, ethyl formate, methyl acetate, ethyl acetate, γ-butyrolactone, methyl lactate or ethyl lactate; amide-based solvents such as formamide, N,N-dimethylformamide, N,N-diethylformamide, N,N-dimethylacetamide, N,N-diethylacetamide, N,N-dimethylpropionamide or N-methylpyrrolidone; carbamide-based solvents such as tetramethylurea or 1,3-dimethyl-2-imidazolidinone; sulfoxide-based solvents such as dimethylsulfoxide; sulfone-based solvents such as dimethylsulfone or sulfolane; and, amine-based solvents such as ammonia, methylamine, dimethylamine, diethylamine, triethylamine, isopropylamine, diisopropylamine, ethyldiisopropylamine, pyrrolidine, N-methylpyrrolidine, piperidine, N-methylpiperidine, morpholine, N-methylmorpholine, pyridine or ethanolamine. One of or two or more of these solvents may be added. The incorporated amount thereof is normally, for example, 0.1 part by weight to 50 parts by weight, preferably 0.1 part by weight to 30 parts by weight, and more preferably 0.1 part by weight to 10 parts by weight, in an agrochemical formulation.

A surfactant can be incorporated as necessary in the agrochemical formulation in addition to the aforementioned incorporated components. There are no particular limitations on the surfactant provided it is normally used in the formulation of agrochemicals, and examples of surfactants that can be used include nonionic surfactants, anionic surfactants and cationic surfactants, preferably one of or two or more of a nonionic surfactant or anionic surfactant can be used, and more preferably one of or two or more of a nonionic surfactant can be used.

Specific examples of surfactants include nonionic surfactants such as polyoxyethylene alkyl allyl ethers, polyoxyethylene alkyl phenyl ethers, polyoxyethylene styryl phenyl ethers, polyoxyethylene-polyoxypropylene block copolymers, polyoxyethylene oleyl esters, polyoxyethylene fatty acid esters or sorbitan fatty acid esters;

anionic surfactants such as alkyl sulfate ester salts, alkylbenzene sulfonates, α-olefin sulfonates, alkyl succinates, polyoxyethylene alkyl aryl ether sulfates and phosphates, polyoxyethylene styryl phenyl ether sulfates and phosphates or alkyl imine salts; and, cationic surfactants such as primary to tertiary fatty amines, alkylammonium chlorides, tetraalkylammonium chlorides, trialkylbenzylammonium salts, alkylpyridinium salts or alkyl hydroxyethyl imidazolium salts, and compounded surfactants, such as an anionic surfactant and cationic surfactant, are also included. These surfactants may be used alone or two or more may be used in combination. The incorporated amount thereof is normally, for example, 0.1 part by weight to 70 parts by weight, preferably 0.1 part by weight to 30 parts by weight, and even more preferably 0.1 part by weight to 10 parts by weight, in the agrochemical formulation.

Additives can be incorporated as necessary in the agrochemical formulation in addition to the aforementioned incorporated components. Additives such as lactic acid, hydrochloric acid, malic acid, sodium citrate, citric acid, disodium hydrogen phosphate, sodium dihydrogen phosphate, dipotassium hydrogen phosphate, potassium dihydrogen phosphate, phthalic acid, potassium hydrogen phthalate, sodium hydroxide, potassium hydroxide, sodium carbonate, potassium carbonate, succinic acid, sodium borate or N-ethylmorpholine can be incorporated as pH adjusters for improving stability of the agrochemical component, for example, at an incorporated ratio of 0.01 part by weight to 10 parts by weight, and preferably 0.05 parts by weight to 5 parts by weight, in the entire fertilizer and agrochemical formulation. Antioxidants such as dibutylhydroxytoluene can be incorporated at an incorporation ratio of 0.001 part by weight to 1 part by weight, and preferably 0.005 parts by weight to 0.5 parts by weight. Ultraviolet absorbers such as 2-hydroxy-4-n-octoxybenzophenone can be incorporated at an incorporation ratio of 0.001 part by weight to 1 part by weight, and preferably 0.005 parts by weight to 0.5 parts by weight. Antifoaming agents such as acetylcholine-based antifoaming agents, silicone-based antifoaming agents, fluorine-based antifoaming agents or fatty acid-based antifoaming agents can be incorporated at an incorporation ratio of 0.001 part by weight to 5 parts by weight, and preferably 0.01 part by weight to 2 parts by weight. In addition, antimicrobial agents such as benzothiazole derivatives, sorbic acid, potassium sorbate, butyl p-hydroxybenzoate, glutaraldehyde, thiazuron or BNPK (2-bromo-2-nitropropane-1,3-diol) can be incorporated at an incorporation ratio of 0.01 part by weight to 5 parts by weight, and preferably 0.01 part by weight to 2 parts by weight.

Moreover, although adjuvants described below such as colorants, crystallization preventive agents, thickeners, dispersants, chelating agents, effect expression promoting agents, composition homogenization accelerators or nitrification inhibitors may also each be added as necessary. These adjuvants are not limited to those exemplified here.

Examples of colorants include: azoic dye, azo dye, acridine, aniline dye, aniline black, indanthrene, eosin, congo red, dihydroindole, methylene blue, phenazine derivative dye, neutral red, phenolphthalein, fuchsin, fluorescein, para red, mauve, carotene; carotenoids such as xanthophylls, cryptoxanthin, zeaxanthin, fucoxanthin, lycopene, lutein; flavonoids such as flavones, flavanones, ants crawl, anthocyans, catechin; quinones such as melanin; porphyrin dye such as chlorophyll, chlorophyllide, bacteriochlorophyll, cytochrome, pheophorbide, Feo porphyrin, hemerythrin, hemoglobin, hemovanadin, hemocyanin, porphyrin, porphine, myoglobin; phycobilin-based pigments such as phycocyanin, phycobilin, phycoerythrin, phytochrome, biliverdin, bilirubin; alizarin, anthocyans, anthraquinone, indigo, urobilin, erythrocruorin, carthamin, hexane cretin Chin, curcumin, crocetin, chlorine, chlorocruorin, genistein, cochineal, Gosshiporu, commelinin, shikonin, Suterukopirin, tannin, Tsurashin, bixin, hypericin, Pin'nagurobin, brazilin, purpurin, betacyanin, berberine, Horubirin, mangosteen (mangostin), Morinjin, laminaran, leghemoglobin, litmus, rhodopsin, rhodoxanthin, Rodomachin, and in addition, for example, carbon black, red iron oxide, solvent Red 23, CI acid Blue 1 (C.I.Acid Blue 1), CI acid yellow 23 (CI acid yellow 23), and the like.

Examples of crystallization preventive agents include ethylene glycol, propylene glycol, glycerin, cyclodextrins, alkylene oxide adduct of glycerin, and the like.

Examples of thickeners include products available from Sansho Co., Ltd. or the like, for example, roast bean gum such as MEYPROLBG FLEUR™ M-200, guar gum such as SUPERGEL™ 200, guar gum derivatives such as JAGUAR™ C-13S, carrageenan such as WG-108, pectin such as YM-150-LJ™, xanthan gum, such as KELZAN™, gellan gum, such as KELCOGEL™ AFT, Daiyu Tan gum such as KELCO-CRETE™ DG, starches such as SB GUM-R™, dextrin such as MALTRIN(registered trademark) M040, cellulose derivatives (carboxymethyl cellulose derivatives) such as FINNFIX™, tara gum such as Supinogamu, and the like.

Examples of dispersants include products available from Kao Corporation or the like, for example, beta-naphthalenesulfonic acid formalin condensate sodium salt such as Demol™ N, special aromatic sulfonic acid-formalin condensate sodium salt such as, Demol™ SN-B, special polycarboxylic acid type polymeric surfactant such as Demol™ P, poly-carboxylic acid sodium salt such as Nopukosupasu™ 44-C, poly-carboxylic acid ammonium salts such as Nopukosupasu™ 5600, special poly-carboxylic acids ammonium salt such as SN Disperse Santo™ 5023, polyphosphate amino alcohol neutralization products such as SN dispersion Santo™ 2060, condensed naphthalene sulfonic acid ammonium salts such as Rome PWA-40™ and the like.

Examples of chelating agents include products available from Chelest Co., for example, EDTA (Ethylene Diamine Tetraacetic Acid), NTA (Nitrilo Triacetic Acid), DTPA (Diethylene Triamine Pentaacetic Acid), HEDTA (Hydroxyethyl Ethylene Diamine Triacetic Acid), TTHA (Triethylene Tetramine Hexaacetic Acid), PDTA (1,3-Propanediamine Tetraacetic Acid), DPTA-OH (1,3-Diamino-2-hydroxypropane Tetraacetic Acid), HIDA (Hydroxyethyl Imino Diacetic Acid), DHEG (Dihydroxyethyl Glycine), GEDTA (Glycol Ether Diamine Tetraacetic Acid), CMGA (Dicarboxymethyl Glutamic Acid), EDDS ((S,S)-Ethylene Diamine Disuccinic Acid), HEDP (Hydroxyethylidene Diphosphonic Acid), NTMP (Nitrilotris (Methylene Phosphonic Acid)), PBTC (Phosphonobutane Tricarboxylic Acid), EDTMP (Ethylene Diamine Tetra (Methylene Phosphonic Acid)), EDTA metal salts such as EDTA.Fe.Na.$H_2O$, DTPA metal salts such as DTPA.Fe.Na.H, PDTA metal salts such as PDTA.Fe.$NR_4H_2O$, $HOCH_2$ $(CHOH)_4COONa$ and the like.

Examples of effect expression promoting agents include ferrous sulfate, copper sulfate, zinc sulfate, ammonium molybdate and the like.

Examples of composition homogenization accelerators include gypsum, paraffin and mineral oil, cornstarch, zeolite and the like.

Examples of nitrification inhibitors include 2-amino-4-chloro-6-methyl-pyrimidine (AM), N-2,5-dichlorophenyl Saku Sina bromide acid (DCS), dicyandiamide, 1-amidino-2-thiourea (ASU) and the like.

The agrochemical formulation can normally be used as a foliage treatment agent, seed treatment agent or directly sprayed agent. When producing an aqueous composition containing the agrochemical formulation by diluting the prepared agrochemical formulation, water such as agricultural water, industrial water, well water or tap water can be used in addition to the water described above provided it does not impair the function or performance of the agrochemical formulation. Although the dilution factor used when preparing an aqueous composition can be suitably selected according to the target application, crop or soil and the like, the agrochemical formulation can be diluted at a dilution factor of 10-fold to 5000-fold and preferably 50-fold to 2000-fold.

In the case of using for foliage treatment, although varying according to the type and content of the active ingredient, a diluted solution of agrochemical formulation typically diluted with water by about 100-fold to 5000-fold is sprayed onto foliage. In addition, a diluted solution of agrochemical formulation diluted with water by about 10-fold to 1000-fold may be sprayed from the air from a helicopter. In the case of using for seed treatment, seeds are soaked in a solution of the agrochemical formulation diluted with water by about 10-fold to 100-fold, or seeds are sprayed with a solution of the agrochemical formulation diluted with water by about 2-fold to 100-fold. In addition, in the case of spraying directly, although the agrochemical formulation can be placed in a 100 mL to 1000 mL plastic bottle having a stoppered opening followed by transferring to a sprayer directly without diluting, the spraying method is not limited thereto. In addition, the applied amount and application time of the agrochemical formulation or aqueous composition containing the agrochemical formulation can be suitably determined corresponding to the agrochemical active ingredient incorporated therein.

EXAMPLES

Although the following provides a more detailed explanation of the present invention through examples thereof, the present invention is not limited to these examples.

Example 1 (Fertilizer and Agrochemical Formulation)

Example 1-A

Dinotefuran (2.5 g, using 2.51 g of sample having purity of 99.6%), Solfit(registered trademark) (3-methoxy-3-methyl-1-butanol, 3.0 g, Kuraray Co., Ltd., fine grade), purified water (44.5 g) and Hyponex(registered trademark)

Gen-eki (highly concentrated liquid fertilizer) (N:P:K=6:10:5, 50.0 g, Hyponex Japan Corp., Ltd.) were mixed and the resulting mixture was stirred at 60° C. to obtain a fertilizer and agrochemical formulation (100.0 g).

Example 1-B to Example 1-Y

The desired fertilizer and agrochemical formulations were obtained using prescribed amounts (g) of dinotefuran, glycol ether, purified water and Hyponex(registered trademark) Gen-eki (highly concentrated liquid fertilizer) in compliance with the method of the aforementioned Example 1-A by mixing the components while stirring at 60° C. The results are shown in below, including the results for Example 1-A. All of the fertilizer and agrochemical formulations of Examples 1-A to 1-Y were transparent, homogeneous liquids.

TABLE 1-1

Fertilizer and Agrochemical Formulation

| Example | Dinotefuran (g) | Glycol ether | Glycol ether (g) | Purified water (g) | Hyponex ® Gen-eki (highly concentrated liquid fertilizer) (g) |
|---|---|---|---|---|---|
| 1-A | 2.5 | Solfit ® | 3.0 | 44.5 | 50.0 |
| 1-B | 2.5 | Solfit ® | 10.0 | 22.5 | 65.0 |
| 1-C | 2.5 | Solfit ® | 5.0 | 17.5 | 75.0 |
| 1-D | 2.5 | Solfit ® | 5.0 | 7.5 | 85.0 |
| 1-E | 5.0 | Solfit ® | 10.0 | 35.0 | 50.0 |
| 1-F | 5.0 | Solfit ® | 10.0 | 25.0 | 60.0 |
| 1-G | 2.5 | Ethylene glycol monoallyl ether | 5.0 | 42.5 | 50.0 |
| 1-H | 2.5 | Diethylene glycol dimethyl ether | 5.0 | 42.5 | 50.0 |
| 1-I | 2.5 | Ethylene glycol monoisopropyl ether | 5.0 | 42.5 | 50.0 |
| 1-J | 2.5 | Ethylene glycol monobutyl ether | 5.0 | 42.5 | 50.0 |
| 1-K | 2.5 | Ethylene glycol monoisobutyl ether | 5.0 | 42.5 | 50.0 |
| 1-L | 2.5 | Diethylene glycol monomethyl ether | 5.0 | 42.5 | 50.0 |

TABLE 1-2

Fertilizer and Agrochemical Formulation

| Example | Dinotefuran (g) | Glycol ether | Glycol ether (g) | Purified water (g) | Hyponex ® Gen-eki (highly concentrated liquid fertilizer) (g) |
|---|---|---|---|---|---|
| 1-M | 2.5 | Deithylene glycol monoisopropyl ether | 5.0 | 42.5 | 50.0 |
| 1-N | 2.5 | Diethylene glycol monoisobutyl ether | 5.0 | 42.5 | 50.0 |
| 1-O | 2.5 | Diethylene glycol monobutyl ether | 5.0 | 42.5 | 50.0 |
| 1-P | 2.5 | Diethylene glycol diethyl ether | 5.0 | 42.5 | 50.0 |
| 1-Q | 2.5 | Diethylene glycol methyl ethyl ether | 5.0 | 42.5 | 50.0 |
| 1-R | 2.5 | Triethylene glycol monomethyl ether | 5.0 | 42.5 | 50.0 |
| 1-S | 2.5 | Triethylene glycol monobutyl ether | 5.0 | 42.5 | 50.0 |
| 1-T | 2.5 | Triethylene glycol dimethyl ether | 5.0 | 42.5 | 50.0 |
| 1-U | 2.5 | Polyethylene glycol monomethyl ether | 5.0 | 42.5 | 50.0 |
| 1-V | 2.5 | Propylene glycol monomethyl ether | 5.0 | 42.5 | 50.0 |
| 1-W | 2.5 | Propylene glycol monopropyl ether | 5.0 | 42.5 | 50.0 |
| 1-X | 2.5 | Dipropylene glycol monomethyl ether | 5.0 | 42.5 | 50.0 |
| 1-Y | 2.5 | Tripropylene glycol monomethyl ether | 5.0 | 42.5 | 50.0 |

Reference Example 1 (Fertilizer and Agrochemical Formulation)

Reference Example 1-a

Dinotefuran (2.5 g, using 2.51 g of sample having purity of 99.6%), purified water (47.5 g) and Hyponex(registered trademark) Gen-eki (highly concentrated liquid fertilizer) (N:P:K=6:10:5, 50.0 g, Hyponex Japan Corp., Ltd.) were mixed and the resulting mixture was stirred at 60° C. to obtain a fertilizer and agrochemical formulation (100.0 g).

Reference Example 1-b to Reference Example 1-f

The desired fertilizer and agrochemical formulations were obtained using prescribed amounts (g) of dinotefuran, purified water and Hyponex(registered trademark) Gen-eki (highly concentrated liquid fertilizer) in compliance with the method of the aforementioned Reference Example 1-a by mixing the components while stirring at 60° C. The results are shown in below, including the results for Reference Example 1-a.

TABLE 2

Fertilizer and Agrochemical Formulation

| Reference Example | Dinotefuran (g) | Glycol ether (g) | Purified water (g) | Hyponex ® Gen-eki (highly concentrated liquid fertilizer) (g) |
|---|---|---|---|---|
| 1 - a | 2.5 | 0 | 47.5 | 50.0 |
| 1 - b | 2.5 | 0 | 32.5 | 65.0 |
| 1 - c | 2.5 | 0 | 22.5 | 75.0 |
| 1 - d | 2.5 | 0 | 12.5 | 85.0 |
| 1 - e | 5.0 | 0 | 45.0 | 50.0 |
| 1-f | 5.0 | 0 | 35.0 | 60.0 |

Test Example 1 (Contained Concentration of Dinotefuran)

Test Example 1-A

Dinotefuran (0.5 g, purity: 99.6%) was placed in a 10 mL sample bottle followed by the addition of the fertilizer and agrochemical formulation of Example 1-A (5 mL) to obtain a sample. This sample was stored for 4 weeks at 25° C. while shaking occasionally. After filtering this sample, the resulting filtrate (solubility measurement sample) was analyzed by HPLC, to show the contained concentration (%) of dinotefuran was 3.3%.

Test Examples 1-B to 1-Y and Reference Examples 1-a to 1-f

Solubility measurement samples were prepared in compliance with Test Example 1-A using the fertilizer and agrochemical formulations obtained in Examples 1-B to 1-Y and Reference Examples 1-a to 1-f followed by determining the contained concentration (%) of dinotefuran of each sample. The results are shown in Table 3-1 and 3-2.

TABLE 3-1

Solubility Measurement Samples

| Example | Contained Concentration of Dinotefuran (%) |
|---|---|
| 1-A | 3.3 |
| 1-B | 4.9 |
| 1-C | 3.0 |
| 1-D | 2.8 |
| 1-E | 5.2 |
| 1-F | 5.1 |
| 1-G | 3.8 |
| 1-H | 3.1 |
| 1-I | 3.5 |
| 1-J | 4.5 |
| 1-K | 4.3 |
| 1-L | 2.8 |
| 1-M | 3.3 |
| 1-N | 3.9 |
| 1-O | 3.9 |
| 1-P | 3.6 |
| 1-Q | 3.3 |
| 1-R | 2.8 |
| 1-S | 3.6 |
| 1-T | 3.0 |
| 1-U | 2.8 |
| 1-V | 3.1 |
| 1-W | 4.0 |
| 1-X | 3.2 |
| 1-Y | 3.4 |

TABLE 3-2

Solubility Measurement Samples

| Reference Example | Contained Concentration of Dinotefuran (%) |
|---|---|
| 1-a | 2.4 |
| 1-b | 1.9 |
| 1-c | 1.6 |
| 1-d | 1.3 |
| 1-e | 2.4 |
| 1-f | 2.0 |

According to the above results, while the concentrations of dinotefuran in the samples of the reference examples, which do not contain glycol ether, were lower than the initial content concentrations, the concentrations of the samples containing glycol ether were sufficient for use as a fertilizer and agrochemical formulation. Namely, the fertilizer and agrochemical formulations of the present invention containing glycol ether were shown to dissolve the required amount of agrochemical, that is dinotefuran, and liquid formulations thereof remained stable.

Example 2 (Fertilizer and Agrochemical Formulation) and Test Example 2 (Concentration of Contained Agrochemical (Agrochemical Solubility))

Example 2-A

Solfit(registered trademark), Hyponex(registered trademark) Gen-eki (highly concentrated liquid fertilizer) and purified water were mixed at a weight ratio of 3:50:44.5 followed by the addition of imidacloprid at 25° C. while stirring until it remained insoluble. This mixture was allowed to stand in a constant temperature room of 25° C.

and stored for 9 days while shaking occasionally. The mixture was then filtered to obtain the desired fertilizer and agrochemical formulation.

Test Example 2-1

This fertilizer and agrochemical formulation (Example 2-A) was analyzed by HPLC, and determination of the contained concentration (%) of imidacloprid yielded a value of 0.093%.

Example 2-B/Test Example 2-B to Example 2-H/Test Example 2-H

The desired fertilizer and agrochemical formulations (Examples 2-B to 2-H) were obtained using clothianidin, thiamethoxam or acetamiprid as shown in the following Table 4 in compliance with the method of the aforementioned Example 2-A.

These fertilizer and agrochemical formulations were analyzed for the concentration of contained agrochemical (agrochemical solubility) (%) by HPLC in compliance with the method of Test Example 2-A. The results are shown in Table 4, including the results of Example 2-A/Test Example 2-A.

compliance with Example 2-A using the same fertilizer component and purified water with the exception of replacing the Solfit(registered trademark) used in Example 2-A with purified water.

Reference Test Example 2-a

In compliance with the method of Test Example 2-A, the contained concentration (agrochemical solubility) (%) of imidacloprid of the fertilizer and agrochemical formulation obtained in Reference Example 2-a was determined 0.041% (Reference Test Example 2-a).

Reference Example 2-2/Reference Test Example 2-2 to Reference Example 2-8/Reference Test Example 2-8

The water-containing fertilizer and agrochemical formulations indicated in the following Table 5 (Reference Examples 2-a to 2-h) were obtained in compliance with the method of the aforementioned Reference Example 2-a using clothianidin, thiamethoxam or acetamiprid instead of the

TABLE 4

| Example | Agrochemical component | Concetration of Contained Agrochemical (%) | Components of Fertilizer and Agrochemical Formulation other than Agrochemical (mixing weight ratio) |
|---|---|---|---|
| 2-A | Imidacloprid | 0.093 | Solfit ®:Hyponex ® Gen-eki (highly concentrated liquid fertilizer):purified water (3:50:44.5) |
| 2-B | Imidacloprid | 0.078 | Solfit ®:Hanakoujou ® Gen-eki (highly concentrated liquid fertilizer):purified water (3:50:44.5) |
| 2-C | Clothianidin | 0.031 | Solfit ®:Hyponex ® Gen-eki (highly concentrated liquid fertilizer):purified water (3:50:44.5) |
| 2-D | Clothianidin | 0.030 | Solfit ®:Hanakoujou ® Gen-eki (highly concentrated liquid fertilizer):purified water (3:50:44.5) |
| 2-E | Thiamethoxam | 0.322 | Solfit ®:Hyponex ® Gen-eki (highly concentrated liquid fertilizer):purified water (3:50:44.5) |
| 2-F | Thiamethoxam | 0.311 | Solfit ®:Hanakoujou ® Gen-eki (highly concentrated liquid fertilizer):purified water (3:50:44.5) |
| 2-G | Acetamiprid | 0.269 | Solfit ®:Hyponex ® Gen-eki (highly concentrated liquid fertilizer):purified water (3:50:44.5) |
| 2-H | Acetamiprid | 0.249 | Solfit ®:Hanakoujou ® Gen-eki (highly concentrated liquid fertilizer):purified water (3:50:44.5) |

Reference Example 2/Reference Test Example 2

Reference Example 2-a

The desired fertilizer and agrochemical formulation (Reference Example 2-a) was obtained as a reference example in imidacloprid of Reference Example 2-a. The concentrations of contained agrochemical (agrochemical solubility) (%) of these fertilizer and agrochemical formulations were analyzed in compliance with Reference Test Example 2-a. The results are shown in Table 5, including the results of Reference Example 2-a/Reference Test Example 2-a.

TABLE 5

| Reference Example | Agrochemical component | Concetration of Contained Agrochemical (%) | Components of Fertilizer and Agrochemical Formulation other than Agrochemical (mixing weight ratio) |
|---|---|---|---|
| 2-a | Imidacloprid | 0.041 | Hyponex ® Gen-eki (highly concentrated liquid fertilizer):purified water (50:47.5) |
| 2-b | Imidacloprid | 0.039 | Hanakoujou ® Gen-eki (highly concentrated liquid fertilizer):purified water (50:47.5) |
| 2-c | Clothianidin | 0.019 | Hyponex ® Gen-eki (highly concentrated liquid fertilizer):purified water (50:47.5) |
| 2-d | Clothianidin | 0.017 | Hanakoujou ® Gen-eki (highly concentrated liquid fertilizer):purified water (50:47.5) |
| 2-e | Thiamethoxam | 0.230 | Hyponex ® Gen-eki (highly concentrated liquid fertilizer):purified water (50:47.5) |
| 2-f | Thiamethoxam | 0.226 | Hanakoujou ® Gen-eki (highly concentrated liquid fertilizer):purified water (50:47.5) |
| 2-g | Acetamiprid | 0.164 | Hyponex ® Gen-eki (highly concentrated liquid fertilizer):purified water (50:47.5) |
| 2-h | Acetamiprid | 0.152 | Hanakoujou ® Gen-eki (highly concentrated liquid fertilizer):purified water (50:47.5) |

According to the above results, the fertilizer and agrochemical formulations containing Solfit(registered trademark), a representative example of a glycol ether, demonstrated improved solubility of the agrochemical component, in comparison with fertilizer and agrochemical formulations not containing glycol ether in the reference examples.

Example 3 (Preparation of Fertilizer and Agrochemical Formulations) Example 3-G

The desired fertilizer and agrochemical formulation (Example 3-G) was obtained by adding dinotefuran (5.0 g, using 5.02 g of sample having purity of 99.6%), Solfit(registered trademark) (10.0 g), purified water (35.0 g) and Hanakoujou (registered trademark) Gen-eki (highly concentrated liquid fertilizer) (N:P:K=5:10:5, 50.0 g) followed by stirring the mixture at 75° C. until the components dissolved.

Examples 3-A to 3-F, Example 3-H and Example 3-I

The desired fertilizer and agrochemical formulations (Examples 3-A to 3-F, Example 3-H and Example 3-I) were obtained in compliance with the method of the aforementioned Example 3-G using prescribed amounts of dinotefuran, glycol ether, purified water and fertilizer component (Hyponex(registered trademark) Gen-eki (highly concentrated liquid fertilizer) or Hanakoujou(registered trademark) Gen-eki (highly concentrated liquid fertilizer)) as shown in the following Table 6. The results are shown in Table 6, including the results for Example 3-G.

TABLE 6

| Example | Dinotefuran Content (g) | Solfit ® Content (g) | Purified Water Content (g) | Fertilizer Component | Fertilizer Component Content (g) |
|---|---|---|---|---|---|
| 3-A | 2.5 | 3.0 | 44.5 | Hyponex ® Gen-eki (highly concentrated liquid fertilizer) | 50.0 |
| 3-B | 2.5 | 10.0 | 22.5 | Hyponex ® Gen-eki (highly concentrated liquid fertilizer) | 65.0 |
| 3-C | 2.5 | 5.0 | 17.5 | Hyponex ® Gen-eki (highly concentrated liquid fertilizer) | 75.0 |
| 3-D | 2.5 | 5.0 | 7.5 | Hyponex ® Gen-eki (highly concentrated liquid fertilizer) | 85.0 |
| 3-E | 5.0 | 10.0 | 35.0 | Hyponex ® Gen-eki (highly concentrated liquid fertilizer) | 50.0 |
| 3-F | 5.0 | 10.0 | 25.0 | Hyponex ® Gen-eki (highly concentrated liquid fertilizer) | 60.0 |
| 3-G | 5.0 | 10.0 | 35.0 | Hanakoujou ® Gen-eki (highly concentrated liquid fertilizer) | 50.0 |
| 3-H | 5.0 | 10.0 | 25.0 | Hanakoujou ® Gen-eki (highly concentrated liquid fertilizer) | 60.0 |
| 3-I | 2.5 | 3.0 | 44.5 | Hanakoujou ® Gen-eki (highly concentrated liquid fertilizer) | 50.0 |

Reference Example 3-a to Reference Example 3-i (Preparation of Fertilizer and Agrochemical Formulations)

The desired fertilizer and agrochemical formulations (Reference Examples 3-a to 3-i) were obtained in compliance with the method of the aforementioned Example 3-G using prescribed amounts of dinotefuran, purified water and fertilizer component (Hyponex(registered trademark) Gen-eki (highly concentrated liquid fertilizer) or Hanakoujou (registered trademark) Gen-eki (highly concentrated liquid fertilizer)) as shown in the following table. The results are shown in Table 7.

TABLE 7

| Example | Dinotefuran Content (g) | Solfit ® Content (g) | Purified Water Content (g) | Fertilizer Component | Fertilizer Component Content (g) |
|---|---|---|---|---|---|
| 3-a | 2.5 | 0 | 47.5 | Hyponex ® Gen-eki (highly concentrated liquid fertilizer) | 50.0 |
| 3-b | 2.5 | 0 | 32.5 | Hyponex ® Gen-eki (highly concentrated liquid fertilizer) | 65.0 |
| 3-c | 2.5 | 0 | 22.5 | Hyponex ® Gen-eki (highly concentrated liquid fertilizer) | 75.0 |
| 3-d | 2.5 | 0 | 12.5 | Hyponex ® Gen-eki (highly concentrated liquid fertilizer) | 85.0 |
| 3-e | 5.0 | 0 | 45.0 | Hyponex ® Gen-eki (highly concentrated liquid fertilizer) | 50.0 |
| 3-f | 5.0 | 0 | 35.0 | Hyponex ® Gen-eki (highly concentrated liquid fertilizer) | 60.0 |
| 3-g | 5.0 | 0 | 45.0 | Hanakoujou ® Gen-eki (highly concentrated liquid fertilizer) | 50.0 |
| 3-h | 5.0 | 0 | 35.0 | Hanakoujou ® Gen-eki (highly concentrated liquid fertilizer) | 60.0 |
| 3-i | 2.5 | 0 | 47.5 | Hanakoujou ® Gen-eki (highly concentrated liquid fertilizer) | 50.0 |

Test Example 3 (Stability of Fertilizer and Agrochemical Formulation)

Stability of the fertilizer and agrochemical composition was measured using the fertilizer and agrochemical formulation of Example 3-A as a representative example thereof. The test sample was stored for 12 days at 40° C. and 54° C. followed by investigation of the residual percentage of dinotefuran and changes in appearance of the liquid formulation. The results are shown in Table 8.

TABLE 8

| Fertilizer and Agrochemical Formulation | Residual Percentage (%) | Storage Conditions | Changes in Appearance |
|---|---|---|---|
| Example 3-A | 99.0 | 40° C., 12 days | None |
| Example 3-A | 95.0 | 54° C., 12 days | None |

According to the above results, the fertilizer and agrochemical formulation of the present invention was not observed to undergo decomposition of the agrochemical component, dinotefuran, and changes in appearance of the liquid formulation were not observed, thereby confirming the stability of the liquid formulation.

Test Example 4 (Stability of Fertilizer and Agrochemical Formulation)

Stability of the fertilizer and agrochemical composition of the present invention was measured using the fertilizer and agrochemical formulations of Examples 3-G to 3-I as representative examples thereof. The test samples were stored for 7 days and 16 days at 54° C. followed by investigation of the residual percentage of dinotefuran and changes in the appearance of the liquid formulation. The results are shown in Table 9.

TABLE 9

| Fertilizer and Agrochemical Formulation | Residual Percentage after 7 Days (%) | Residual Percentage after 16 Days (%) | Changes in Appearance |
|---|---|---|---|
| Example 3-G | 100 | 98.9 | None |
| Example 3-H | 100 | 97.3 | None |
| Example 3-I | 100 | 98.9 | None |

According to the above results, the fertilizer and agrochemical formulations of the present invention were not observed to undergo decomposition of the agrochemical component, dinotefuran, and changes in appearance of the liquid formulation were not observed, thereby confirming the stability of the liquid formulation.

Test Example 5 (Homogeneity of Fertilizer and Agrochemical Formulation)

Homogeneity of fertilizer and agrochemical formulations were measured using the fertilizer and agrochemical formulations of Example 3-B, Example 3-D, Example 3-E, Example 3-F, Reference Example 3-b, Reference Example 3-d, Reference Example 3-e and Reference Example 3-f as representative examples thereof. The test samples were stored for 4 days at −5° C. followed by investigation of crystallization in the liquid formulations and changes in appearance of the liquid formulations.

TABLE 10

| Fertilizer and Agrochemical Formulation | Stability |
|---|---|
| Example 3-B | ○ ● |
| Example 3-D | ○ ● |
| Example 3-E | ○ ● |
| Example 3-F | ○ ● |
| Reference Example 3-b | X |
| Reference Example 3-d | X |
| Reference Example 3-e | X |
| Reference Example 3-f | X |

○: No crystallization
●: No change in appearance
X: Crystallization
⊠: Change in appearance According to the above results, while crystallization was observed in the fertilizer and agrochemical formulations of Reference Examples 3-b, 3-d, 3-e and 3-f not containing Solfit(registered trademark), crystallization was not observed in the fertilizer and agrochemical formulations containing Solfit(registered trademark), thereby confirming stability of the liquid formulations at low temperatures.

Test Example 6 (Low-Temperature Stability of Fertilizer and Agrochemical Formulations)

Low-temperature stability was measured using the fertilizer and agrochemical formulations of Example 3-G and Example 3-H and the fertilizer and agrochemical formulations of Reference Example 3-g and Reference Example 3-h as representative examples thereof. The test samples were stored for 7 days at 5° C. followed by investigation of crystallization in the liquid formulations and changes in appearance of the liquid formulations. The results are shown in Table 11.

TABLE 11

| Fertilizer and Agrochemical Formulation | Stability |
|---|---|
| Example 3-G | ○ ● |
| Example 3-H | ○ ● |
| Reference Example 3-g | X |
| Reference Example 3-h | X |

○: No crystallization
●: No change in appearance
X: Crystallization
⊠: Change in appearance According to the above results, while crystallization was observed in the fertilizer and agrochemical formulation of Reference Examples 3-g and 3-h not containing Solfit (registered trademark), crystallization was not observed in the fertilizer and agrochemical formulations of the present invention containing Solfit(registered trademark), thereby confirming stability of the liquid formulation s at low temperatures.

Test Example 7 (Flammability of Fertilizer and Agrochemical Mixed Liquid Formulation)

The flammability of the fertilizer and agrochemical formulations of Example 3-E and Example 3-G was investigated using a Cleveland open-cup flash point tester. The results are shown in Table 12.

TABLE 12

| Temperature | Fertilizer and Agrochemical Formulation of Example 3-E | Fertilizer and Agrochemical Formulation of Example 3-G |
|---|---|---|
| 20° C. | No ignition | No ignition |
| 25° C. | No ignition | No ignition |
| 30° C. | No ignition | No ignition |
| 35° C. | No ignition | No ignition |
| 40° C. | No ignition | No ignition |
| 45° C. | No ignition | No ignition |
| 50° C. | No ignition | No ignition |
| 55° C. | No ignition | No ignition |
| 60° C. | No ignition | No ignition |
| 65° C. | No ignition | No ignition |
| 70° C. | No ignition | No ignition |
| 75° C. | No ignition | No ignition |
| 80° C. | No ignition | No ignition |
| 85° C. | No ignition | No ignition |
| 90° C. | No ignition | No ignition |
| 95° C. | No ignition | No ignition |
| 100° C. | No ignition Embers extinguished with steam | No ignition Embers extinguished with steam |

According to the above results, since none of the fertilizer and agrochemical formulations of Examples 3-E and 3-G ignited, the fertilizer and agrochemical formulation of the present invention was confirmed to be a liquid formulation having an extremely low level of danger.

Example 4 (Preparation of Diluted Fertilizer and Agrochemical Formulation Solutions (Fertilizer and Agrochemical Aqueous Formulations))

Example 4-A-100

1 g of the fertilizer and agrochemical formulation of Example 3-A was diluted with 99 g of purified water to obtain a fertilizer and agrochemical aqueous composition (4-A-100).

Example 4-A-250

0.4 g of the fertilizer and agrochemical formulation of Example 3-A were diluted with 99.6 g of purified water to obtain a fertilizer and agrochemical aqueous composition (4-A-250).

Example 4-A-500

0.2 g of the fertilizer and agrochemical formulation of Example 3-A were diluted with 99.8 g of purified water to obtain a fertilizer and agrochemical aqueous composition (4-A-500).

Example 4-A-1000

0.1 g of the fertilizer and agrochemical formulation of Example 3-A were diluted with 99.9 g of purified water to obtain a fertilizer and agrochemical aqueous composition (4-A-1000).

Examples 4-E-100, 4-E-250, 4-E-500, 4-E-1000, 4-H-100, 4-H-250, 4-H-500 and 4-H-1000

The fertilizer and agrochemical mixed liquid formulations of Examples 3-E and 3-H were diluted with purified water in compliance with the methods of the aforementioned Examples 4-A-100, 4-A-250, 4-A-500 and 4-A-1000 to obtain the desired fertilizer and agrochemical aqueous compositions (Examples 4-E-100, 4-E-250, 4-E-500, 4-E-1000, 4-H-100, 4-H-250, 4-H-500 and 4-H-1000) as shown in the following Table 13. The results are shown in Table 13, including the results for Examples 4-A-100, 4-A-250, 4-A-500 and 4-A-1000.

TABLE 13

| Example | Dinotefuran Content (g) | Solfit ® Content (g) | Purified Water Content (g) | Fertilizer Component | Fertilizer Component Content (g) |
| --- | --- | --- | --- | --- | --- |
| 4-A-100 | 0.025 | 0.030 | 99.445 | Hyponex ® Gen-eki (highly concentrated liquid fertilizer) | 0.50 |
| 4-A-250 | 0.010 | 0.012 | 99.778 | Hyponex ® Gen-eki (highly concentrated liquid fertilizer) | 0.20 |
| 4-A-500 | 0.0050 | 0.0060 | 99.889 | Hyponex ® Gen-eki (highly concentrated liquid fertilizer) | 0.10 |
| 4-A-1000 | 0.0025 | 0.0030 | 99.9445 | Hyponex ® Gen-eki (highly concentrated liquid fertilizer) | 0.050 |
| 4-E-100 | 0.050 | 0.10 | 99.35 | Hyponex ® Gen-eki (highly concentrated liquid fertilizer) | 0.50 |
| 4-E-250 | 0.020 | 0.040 | 99.74 | Hyponex ® Gen-eki (highly concentrated liquid fertilizer) | 0.20 |
| 4-E-500 | 0.010 | 0.020 | 99.87 | Hyponex ® Gen-eki (highly concentrated liquid fertilizer) | 0.10 |
| 4-E-1000 | 0.0050 | 0.010 | 99.935 | Hyponex ® Gen-eki (highly concentrated liquid fertilizer) | 0.050 |
| 4-H-100 | 0.050 | 0.10 | 99.25 | Hanakoujou ® Gen-eki (highly concentrated liquid fertilizer) | 0.60 |
| 4-H-250 | 0.020 | 0.040 | 99.70 | Hanakoujou ® Gen-eki (highly concentrated liquid fertilizer) | 0.24 |
| 4-H-500 | 0.010 | 0.020 | 99.85 | Hanakoujou ® Gen-eki (highly concentrated liquid fertilizer) | 0.12 |
| 4-H-1000 | 0.0050 | 0.010 | 99.925 | Hanakoujou ® Gen-eki (highly concentrated liquid fertilizer) | 0.060 |

Reference Examples 4-a-100, 4-a-250, 4-a-500, 4-a-1000, 4-e-100, 4-e-250, 4-e-500, 4-e-1000, 4-h-100, 4-h-250, 4-h-500 and 4-h-1000

The fertilizer and agrochemical compositions of Reference Examples 3-a, 3-e and 3-h were diluted with purified water in compliance with the methods of the aforementioned Examples 4-A-100, 4-A-250, 4-A-500 and 4-A-1000 to obtain desired diluted solutions of fertilizer and agrochemical mixed liquid formulations (Reference Examples 4-a-100, 4-a-250, 4-a-500, 4-a-1000, 4-e-100, 4-e-250, 4-e-500, 4-e-1000, 4-h-100, 4-h-250, 4-h-500 and 4-h-1000) as shown in the following Table 14. The results are shown in Table 14.

TABLE 14

| Reference Example | Dinotefuran Content (g) | Solfit ® Content (g) | Purified Water Content (g) | Fertilizer Component | Fertilizer Component Content (g) |
| --- | --- | --- | --- | --- | --- |
| 4-a-100 | 0.025 | 0 | 99.475 | Hyponex ® Gen-eki (highly concentrated liquid fertilizer) | 0.50 |
| 4-a-250 | 0.010 | 0 | 99.79 | Hyponex ® Gen-eki (highly concentrated liquid fertilizer) | 0.20 |
| 4-a-500 | 0.0050 | 0 | 99.895 | Hyponex ® Gen-eki (highly concentrated liquid fertilizer) | 0.10 |
| 4-a-1000 | 0.0025 | 0 | 99.9475 | Hyponex ® Gen-eki (highly concentrated liquid fertilizer) | 0.050 |
| 4-e-100 | 0.050 | 0 | 99.45 | Hyponex ® Gen-eki (highly concentrated liquid fertilizer) | 0.50 |
| 4-e-250 | 0.020 | 0 | 99.78 | Hyponex ® Gen-eki (highly concentrated liquid fertilizer) | 0.20 |
| 4-e-500 | 0.010 | 0 | 99.89 | Hyponex ® Gen-eki (highly concentrated liquid fertilizer) | 0.10 |
| 4-e-1000 | 0.0050 | 0 | 99.945 | Hyponex ® Gen-eki (highly concentrated liquid fertilizer) | 0.050 |
| 4-h-100 | 0.050 | 0 | 99.35 | Hanakoujou ® Gen-eki (highly concentrated liquid fertilizer) | 0.60 |
| 4-h-250 | 0.020 | 0 | 99.74 | Hanakoujou ® Gen-eki (highly concentrated liquid fertilizer) | 0.24 |
| 4-h-500 | 0.010 | 0 | 99.87 | Hanakoujou ® Gen-eki (highly concentrated liquid fertilizer) | 0.12 |

TABLE 14-continued

| Reference Example | Dinotefuran Content (g) | Solfit ® Content (g) | Purified Water Content (g) | Fertilizer Component | Fertilizer Component Content (g) |
|---|---|---|---|---|---|
| 4-h-1000 | 0.0050 | 0 | 99.935 | Hanakoujou ® Gen-eki (highly concentrated liquid fertilizer) | 0.060 |

Test Example 8 (Homogeneity of Diluted Fertilizer and Agrochemical Formulation Solutions)

Homogeneity of fertilizer and agrochemical formulations of the present invention were measured using the diluted fertilizer and agrochemical formulation solutions of Examples 4-A-100, 4-A-250, 4-E-1000 and 4-H-500 and Reference Examples 4-a-100, 4-a-250, 4-e-1000 and 4-h-500 as representative examples thereof. The test samples were stored for 6 days to 15 days at −0.5° C. or −0.3° C. followed by an investigation of crystallization in the diluted liquid formulation solutions and changes in the appearance thereof. The test was carried out in triplicate for each diluted liquid formulation solution. The results are shown in Table 15.

TABLE 15

| Fertilizer and Agrochemical Formulation Diluted Solution | Storage Lot Conditions | | Stability |
|---|---|---|---|
| Example 4-A-100 | 1 | −0.5° C., 6 days | ○ ● |
| Example 4-A-100 | 2 | −0.5° C., 6 days | ○ ● |
| Example 4-A-100 | 3 | −0.5° C., 6 days | ○ ● |
| Example 4-A-250 | 1 | −0.3° C., 15 days | ○ ● |
| Example 4-A-250 | 2 | −0.3° C., 15 days | ○ ● |
| Example 4-A-250 | 3 | −0.3° C., 15 days | ○ ● |
| Example 4-E-1000 | 1 | −0.5° C., 8 days | ○ ● |
| Example 4-E-1000 | 2 | −0.5° C., 8 days | ○ ● |
| Example 4-E-1000 | 3 | −0.5° C., 8 days | ○ ● |
| Example 4-H-500 | 1 | −0.3° C., 7 days | ○ ● |
| Example 4-H-500 | 2 | −0.3° C., 7 days | ○ ● |
| Example 4-H-500 | 3 | −0.3° C., 7 days | ○ ● |
| Reference Example 4-a-100 | 1 | −0.5° C., 6 days | ⊠ (Freezing) |
| Reference Example 4-a-100 | 2 | −0.5° C., 6 days | ⊠ (Freezing) |
| Reference Example 4-a-100 | 3 | −0.5° C., 6 days | ⊠ (Freezing) |
| Reference Example 4-a-250 | 1 | −0.3° C., 15 days | ⊠ (Freezing) |
| Reference Example 4-a-250 | 2 | −0.3° C., 15 days | ○ ● |
| Reference Example 4-a-250 | 3 | −0.3° C., 15 days | ⊠ (Freezing) |
| Reference Example 4-e-1000 | 1 | −0.5° C., 8 days | ⊠ (Freezing) |
| Reference Example 4-e-1000 | 2 | −0.5° C., 8 days | ⊠ (Freezing) |
| Reference Example 4-e-1000 | 3 | −0.5° C., 8 days | ⊠ (Freezing) |
| Reference Example 4-h-500 | 1 | −0.3° C., 7 days | ⊠ (Freezing) |
| Reference Example 4-h-500 | 2 | −0.3° C., 7 days | ⊠ (Freezing) |
| Reference Example 4-h-500 | 3 | −0.3° C., 7 days | ⊠ (Freezing) |

○: No crystallization
●: No change in appearance
X: Crystallization
⊠: Change in appearance According to the above results, in contrast to changes in appearance (freezing) being observed in all lots of the diluted fertilizer and agrochemical formulation solutions of Reference Examples 4-a-100, 4-a-250, 4-e-1000 and 4-h-500 not containing Solfit(registered trademark) used as controls, with the exception of Lot 2 of Reference Example 4-a-250, there was no crystallization or changes in appearance observed in the diluted fertilizer and agrochemical formulation solutions of Examples 4-A-100, 4-A-250, 4-E-1000 and 4-H-500 containing Solfit(registered trademark) of the present invention, thereby confirming the stability of the diluted liquid formulation solutions at low temperatures.

Example 5 (Preparation Example of Premix, Corresponding to Example 1)

Solfit(registered trademark) and purified water (445 g) were mixed and the resulting mixture was stirred to obtain 6.32% of Solfit(registered trademark) aqueous solution (475 g). To 6.32% of Solfit(registered trademark) aqueous solution (47.5 g), dinotefuran (2.5 g; using 2.5 g of sample having purity of 99.6%) was added and stirred for 1 hr. at 45° C. to obtain an aqueous solution containing 5.0% of dinotefuran and 6% of Solfit(registered trademark).

Example 6 (Preparation Example of Premix, Corresponding to Example 2)

To 6.32% of Solfit(registered trademark) aqueous solution (47.5 g), imidacloprid (0.0898 g; using 0.0905 g of sample having purity of 99.2%) was added and the resulting mixture was stirred for 1 hr. at 60° C. while occasionally disrupted by ultrasonic to obtain an aqueous solution containing 0.189% of imidacloprid and 6.30% of Solfit(registered trademark).

Example 7 (Preparation Example of Premix, Corresponding to Example 2)

To 6.32% of Solfit(registered trademark) aqueous solution (47.5 g), clothianidin (0.0272 g; using 0.0284 g of sample having purity of 95.8%) was added and the resulting mixture was stirred for 30 min. at 60° C. while occasionally disrupted by ultrasonic to obtain an aqueous solution containing 0.0573% of imidacloprid and 6.32% of Solfit(registered trademark).

Example 8 (Preparation Example of Premix, Corresponding to Example 2)

To 6.32% of Solfit(registered trademark) aqueous solution (47.5 g), thiamethoxam (0.284 g; using 0.290 g of sample having purity of 98.0%) was added and the resulting mixture was stirred for 15 min. at 60° C. while occasionally disrupted by ultrasonic to obtain an aqueous solution containing 0.594% of imidacloprid and 6.28% of Solfit(registered trademark).

Example 9 (Preparation Example of Premix, Corresponding to Example 2)

To 6.32% of Solfit(registered trademark) aqueous solution (47.5 g), acetamiprid (0.252 g; using 0.253 g of sample having purity of 99.6%) was added and the resulting mixture was stirred for 20 min. at 60° C. while occasionally disrupted by ultrasonic to obtain an aqueous solution of 0.527% of acetamiprid and 6.28% of Solfit(registered trademark).

Example 10 (Preparation Example of Premix, Corresponding to Example 3)

Dinotefuran (5 g; using 5.00 g of sample having purity 99.6%) and Solfit(registered trademark) (10 g) were mixed with purified water (35.0 g) and the resulting mixture was stirred for 20 min. at 60° C. An aqueous solution containing 10% of dinotefuran and 20% Solfit(registered trademark) was obtained.

Example 11 (Preparation Example of Premix)

Dinotefuran (12.5 g; using 12.5 g of sample having purity 99.6%) and Solfit(registered trademark)(15.0 g) were mixed with purified water (72.5 g) and the resulting mixture was stirred for 20 min. at 60° C. An aqueous solution containing 12.5% of dinotefuran and 15.0% Solfit(registered trademark) was obtained.

Example 12 (Preparation Example of Premix)

Dinotefuran (24.9 g; using 25.0 g of sample having purity 99.6%) and Solfit(registered trademark)(30.0 g) were mixed with purified water (45.0 g) and the resulting mixture was stirred for 20 min. at 60° C. An aqueous solution containing 25.0% of dinotefuran and 30% Solfit(registered trademark) was obtained.

Example 13 (Preparation of Fertilizer and Agrochemical Formulation; Corresponding to Example 1: Aqueous Solution of Agrochemical-Solfit(Registered Trademark)+Concentrated Liquid Fertilizer)

To 50 g of the aqueous solution containing 5.0% of dinotefuran and 6% of Solfit(registered trademark) obtained in Example 5, 50 g of Hyponex(registered trademark) Gen-eki (highly concentrated liquid fertilizer) was added and the resulting mixture was stirred to obtain a fertilizer and agrochemical formulation.

Example 14 (Preparation of Fertilizer and Agrochemical Formulation: Concentrated Liquid Fertilizer+Concentrated Aqueous Solution of Agrochemical-Solfit(Registered Trademark)+Water)

To 50 g of Hyponex(registered trademark) Gen-eki (highly concentrated liquid fertilizer), 20 g of the aqueous solution containing 12.5% of dinotefuran and 15.0% of Solfit(registered trademark) obtained in Example 11 was added and resulting mixture was shaken to obtain a fertilizer and agrochemical formulation 14A. To obtained formulation 14A, 30 g of purified water was added and the resulting mixture was shaken to obtain a fertilizer and agrochemical formulation 14B.

Example 15 (Preparation of Fertilizer and Agrochemical Formulation: Concentrated Aqueous Solution of Agrochemical-Solfit(Registered Trademark)+Concentrated Liquid Fertilizer+Water)

To 10 g of the aqueous solution containing 25% of dinotefuran and 30% of Solfit(registered trademark) obtained in Example 12, 50 g of Hanakoujou(registered trademark) Gen-eki (highly concentrated liquid fertilizer) was added and resulting mixture was shaken to obtain a fertilizer and agrochemical formulation 15A. To obtained formulation 15A, 40 g of water was added and the resulting mixture was shaken to obtain a fertilizer and agrochemical formulation 15B.

Example 16 (Preparation of Fertilizer and Agrochemical Formulation; Corresponding to Example 2: Aqueous Solution of Agrochemical-Solfit(Registered Trademark)+Concentrated Liquid Fertilizer)

To 47.5905 g of the aqueous solution containing 0.189% of imidacloprid and 6.30% of Solfit(registered trademark). obtained in Example 6, 50 g of Hyponex(registered trademark) Gen-eki (highly concentrated liquid fertilizer) was added and the resulting mixture was stirred to obtain a fertilizer and agrochemical formulation.

Example 17 (Preparation of Fertilizer and Agrochemical Formulation; Corresponding to Example 2: Aqueous Solution of Agrochemical-Solfit+Concentrated Liquid Fertilizer)

To 47.5284 g of the aqueous solution containing 0.0573% of clotianidin and 6.32% of Solfit(registered trademark). obtained in Example 7, 50 g of Hanakoujou(registered trademark) Gen-eki (highly concentrated liquid fertilizer) was added and the resulting mixture was stirred to obtain a fertilizer and agrochemical formulation.

Example 18 (Preparation of Fertilizer and Agrochemical Formulation; Corresponding to Example 2: Aqueous Solution of Agrochemical-Solfit (Registered Trademark)+Concentrated Liquid Fertilizer)

To 47.790 g of the aqueous solution containing 0.594% of thiamethoxam and 6.28% of Solfit(registered trademark) obtained in Example 8, 50 g of Hanakoujou(registered trademark) Gen-eki (highly concentrated liquid fertilizer) was added and the resulting mixture was stirred to obtain a fertilizer and agrochemical formulation.

Example 19 (Preparation of Fertilizer and Agrochemical Formulation; Corresponding to Example 2: Aqueous Solution of Agrochemical-Solfit(Registered Trademark).+Concentrated Liquid Fertilizer)

To 47.753 g of the aqueous solution containing 0.527% of acetamiprid and 6.28% of Solfit(registered trademark) obtained in Example 9, 50 g of Hyponex(registered trademark) Gen-eki (highly concentrated liquid fertilizer) was added and the resulting mixture was stirred to obtain a fertilizer and agrochemical formulation.

Example 20 (Preparation of Fertilizer and Agrochemical Formulation; Corresponding to Example 3: Aqueous Solution of Agrochemical-Solfit(Registered Trademark).+Concentrated Liquid Fertilizer)

To 50 g of the aqueous solution containing 10% of dinotefuran and 20% of Solfit(registered trademark) obtained in Example 10, 50 g of Hyponex(registered trademark) Gen-eki (highly concentrated liquid fertilizer) was added and the resulting mixture was stirred to obtain a fertilizer and agrochemical formulation.

Example 21 (Preparation of Fertilizer and Agrochemical Formulation: Simultaneously Adding Agrochemical Formulation and Glycol Ether to Concentrated Liquid Fertilizer)

To dinotefuran (24.9 g: using 25.0 g of sample having purity of 99.6%), 445 g of purified water was added and the resulting mixture was stirred for 30 min. at 60° C. to obtain an aqueous solution containing 5.3% of dinotefrun. To 50 g of Hyponex(registered trademark) Gen-eki (highly concentrated liquid fertilizer), 47 g of the aqueous solution containing 5.3% of dinotefrun and 3.0 g of Solfit(registered trademark) were added simultaneously while stirring to obtain a fertilizer and agrochemical formulation.

Example 22 (Preparation of Fertilizer and Agrochemical Formulation: Adding Agrochemical Formulation to Concentrated Liquid Fertilizer Followed by Adding Glycol Ether)

To 50 g of Hyponex(registered trademark) Gen-eki (highly concentrated liquid fertilizer), 47 g of aqueous solution containing 5.3% of dinotefuran was added while stirring. To the obtained solution, 3.0 g of Solfit(registered trademark) was added while stirring to obtain a fertilizer and agrochemical formulation.

Example 23 (Preparation of Fertilizer and Agrochemical Formulation: Adding Glycol Ether to Concentrated Liquid Fertilizer Followed by Adding Agrochemical Formulation)

To 50 g of Hyponex(registered trademark) Gen-eki (highly concentrated liquid fertilizer), 3.0 g of Solfit(registered trademark) was added while stirring. To the obtained solution, 47 g of aqueous solution containing 5.3% of dinotefuran was added while stirring to obtain a fertilizer and agrochemical formulation.

Example 24 (Preparation of Fertilizer and Agrochemical Formulation: Simultaneously Adding Concentrated Liquid Fertilizer and Glycol Ether to Agrochemical Formulation)

To 47 g of aqueous solution containing 5.3% of dinotefuran, 50 g of Hyponex(registered trademark) Gen-eki (highly concentrated liquid fertilizer) and 3.0 g of Solfit (registered trademark) were added simultaneously while stirring to obtain a fertilizer and agrochemical formulation.

Example 25 (Preparation of Fertilizer and Agrochemical Formulation: Adding Concentrated Liquid Fertilizer to Agrochemical Formulation Followed by Adding Glycol Ether)

To 47 g of aqueous solution containing 5.3% of dinotefuran, 50 g of Hyponex(registered trademark) Gen-eki (highly concentrated liquid fertilizer) was added while stirring. To the obtained solution, 3.0 g of Solfit(registered trademark) was added while stirring to obtain a fertilizer and agrochemical formulation.

Example 26 (Preparation of Fertilizer and Agrochemical Formulation: Adding Glycol Ether to Agrochemical Formulation Followed by Adding Concentrated Liquid Fertilizer)

To 47 g of aqueous solution containing 5.3% of dinotefuran, 3.0 g of Solfit(registered trademark) was added while stirring. To the obtained solution, 50 g of Hyponex(registered trademark) Gen-eki (highly concentrated liquid fertilizer) was added while stirring to obtain a fertilizer and agrochemical formulation.

Example 27 (Preparation of Fertilizer and Agrochemical Formulation: Simultaneously Adding Agrochemical Formulation and Concentrated Liquid Fertilizer to Glycol Ether)

To 3.0 g of Solfit(registered trademark), 47 g of aqueous solution containing 5.3% of dinotefuran and 50 g of Hyponex(registered trademark) Gen-eki (highly concentrated liquid fertilizer) were added simultaneously while stirring to obtain a fertilizer and agrochemical formulation.

Example 28 (Preparation of Fertilizer and Agrochemical Formulation: Adding Agrochemical Formulation to Glycol Ether Followed by Adding Concentrated Liquid Fertilizer)

To 3.0 g of Solfit(registered trademark), 47 g of aqueous solution containing 5.3% of dinotefuran was added while stirring. To the obtained solution, 50 g of Hyponex(registered trademark) Gen-eki (highly concentrated liquid fertilizer) was added while stirring to obtain a fertilizer and agrochemical formulation.

Example 29 (Preparation of Fertilizer and Agrochemical Formulation: Adding Concentrated Liquid Fertilizer to Glycol Ether Followed by Adding Agrochemical Formulation)

To 3.0 g of Solfit(registered trademark), 50 g of Hyponex (registered trademark) Gen-eki (highly concentrated liquid fertilizer) was added while stirring. To the obtained solution, 47 g of aqueous solution containing 5.3% of dinotefuran was added while stirring to obtain a fertilizer and agrochemical formulation.

Example 30 (Preparation of Fertilizer and Agrochemical Formulation: Adding Agrochemical Bulk to Aqueous Solution of Glycol Ether Followed by Adding Liquid Fertilizer)

To 47.5 g of aqueous solution containing 6.32% of Solfit(registered trademark), dinotefuran (2.5 g; using 2.5 g of sample having purity 99.6%) was added. To the obtained mixture, 50 g of Hyponex(registered trademark) Gen-eki (highly concentrated liquid fertilizer) was added and the resulting mixture was stirred for 20 min. at 60° C. to obtain a dissolved fertilizer and agrochemical formulation.

Example 31 (Preparation of Fertilizer and Agrochemical Formulation: Adding Liquid Fertilizer to Aqueous Solution of Glycol Ether Followed by Adding Agrochemical Bulk)

To 47.5 g of aqueous solution containing 6.32% of Solfit(registered trademark), 50 g of Hyponex(registered trademark) Gen-eki (highly concentrated liquid fertilizer) was added. To the obtained solution, dinotefuran (2.5 g; using 2.5 g of sample having purity 99.6%) was added. The obtained mixture was stirred for 20 min. at 60° C. to obtain a dissolved fertilizer and agrochemical formulation.

Example 32 (Preparation of Fertilizer and Agrochemical Formulation: Adding Water to Premix Followed by Adding Powdery Fertilizer Bulk)

To 50 g of premix that is an aqueous solution containing 5.0% of dinotefuran and 6% of Solfit(registered trademark), 30 g of water was added. To the obtained mixture, 20 g of Peters(registered trademark) (15-11-29) was added and then heated to 50° C. While keeping at 50° C., the resulting mixture was stirred for 30 min. to obtain a dissolved fertilizer and agrochemical formulation.

Example 33 (Preparation of Fertilizer and Agrochemical Formulation: Adding Water to Premix Followed by Adding Powdery Fertilizer Bulk)

To 50 g of premix that is an aqueous solution containing 5.0% of dinotefuran and 6% of Solfit(registered trademark), 31.2 g of water was added. To the obtained mixture, 18.75 g of Universol(registered trademark) (16-5-25) was added and then heated to 50° C. While keeping at 50° C., the resulting mixture was stirred for 30 min. to obtain a dissolved fertilizer and agrochemical formulation.

Example 34 (Preparation of Fertilizer and Agrochemical Formulation: Adding Water to Premix Followed by Adding Powdery Fertilizer Bulk)

To 30 g of water, 50 g of premix that is an aqueous solution containing 5.0% of dinotefuran and 6% of Solfit (registered trademark) was added. To the obtained mixture, 20 g of Peters(registered trademark) (15-11-29) was added and then heated to 50° C. While keeping at 50° C., the resulting mixture was stirred for 30 min. to obtain a dissolved fertilizer and agrochemical formulation.

Example 35 (Preparation of Fertilizer and Agrochemical Formulation: Adding Premix to Water Followed by Adding Powdery Fertilizer Bulk)

To 31.25 g of water, 50 g of premix that is an aqueous solution containing 5.0% of dinotefuran and 6% of Solfit (registered trademark) was added. To the obtained mixture, 18.75 g of Universol(registered trademark) (16-5-25) was added and then heated to 50° C. While keeping at 50° C., the resulting mixture was stirred for 30 min. to obtain a dissolved fertilizer and agrochemical formulation.

Example 36 (Preparation of Fertilizer and Agrochemical Formulation: Adding Water to Premix Followed by Adding Powdery Fertilizer Bulk)

To 50 g of premix that is an aqueous solution containing 5.0% of dinotefuran and 6% of Solfit(registered trademark), 33.3 g of water was added and the resulting mixture was heated to 50° C. while stirring and then 2 g of urea, 6 g of potassium nitrate and 8.7 g of phosphate monobasic ammonia were added. The obtained mixture was kept at 50° C. and stirred for 30 min. to obtain a dissolved fertilizer and agrochemical formulation. The formulation contained fertilizer components as N–P–K=2.65–5.22–2.64.

Example 37 (Preparation of Fertilizer and Agrochemical Formulation: Adding Water to Premix Followed by Adding Powdery Fertilizer Bulk)

To 50 g of premix that is an aqueous solution containing 5.0% of dinotefuran and 6% of Solfit(registered trademark), 33.3 g of water was added and the resulting mixture was heated to 50° C. while stirring and then 5.5 g of urea, 5 g of potassium nitrate, 2.5 g of phosphate monobasic ammonia and 3.7 g of phosphate monobasic potassium were added. The obtained mixture was kept at 50° C. and stirred for 30 min. to obtain a dissolved fertilizer and agrochemical formulation. The formulation contained fertilizer components as N–P–K=3.45–3.38–3.45.

Example 38 (Preparation of Fertilizer and Agrochemical Formulation: Adding Water to Premix Followed by Adding Powdery Fertilizer Bulk)

To 50 g of premix that is an aqueous solution containing 5.0% of dinotefuran and 6% of Solfit(registered trademark), 33.3 g of water was added and the resulting mixture was heated to 50° C. while stirring and then 4 g of urea, 8.5 g of potassium nitrate and 4.2 g of dihydrogen phosphate ammonia were added. The obtained mixture was kept at 50° C. and stirred for 30 min. to obtain a dissolved fertilizer and agrochemical formulation. The formulation contained fertilizer components as N–P–K=3.82–2.14–3.74.

The disclosures of Japanese patent Application No. 2015-086227, filed on Apr. 20, 2015 are incorporated by reference herein. All publications, patent applications, and technical standards mentioned in this specification are herein incorporated by reference to the same extent as if each individual publication, patent application, or technical standard was specifically and individually indicated to be incorporated by reference.

INDUSTRIAL APPLICABILITY

According to the present invention, a fertilizer and agrochemical formulation can be provided that have the properties of a stable and homogeneous liquid, not only under harsh conditions, but also at low temperatures, while also having an extremely low level of danger. Therefore, the fertilizer and agrochemical formulation, an aqueous composition containing a fertilizer and an agrochemical and method for use thereof, and a raw material for producing the fertilizer and agrochemical formulation that are not found in conventional can be provided.

The invention claimed is:

1. A transparent, homogeneous liquiform fertilizer and agrochemical formulation comprising an active agrochemical that is not a fertilizer and a fertilizer together with glycol ether, wherein the content ratio of the active agrochemical is 0.01% by weight to 10% by weight with respect to the total weight of the formulation, and the particle diameter of particles in the transparent, homogeneous liquiform fertilizer and agrochemical formulation is less than 100 nm by using a particle size distribution analyzer.

2. The formulation according to claim 1, which comprises water.

3. The formulation according to claim 1, wherein the active agrochemical comprises:
an insecticide selected from the group consisting of
carbamate acetylcholinesterase (AChE) inhibitors, organophosphorous acetylcholinesterase (AChE) inhibitors, cyclodiene organochlorine GABA-gated chlorine ion channel blockers, phenylpyrazole (fiprole) GABA-gated chlorine ion channel blockers, pyrethroid and pyrethrin sodium channel modulators, DDT and methoxychlor sodium channel modulators, neonicotinoid nicotinic acetylcholine receptor (nAChR) competitive modulators, nicotin nicotinic acetylcholine receptor (nAChR) competitive modulators, sulfoximine nicotinic acetylcholine receptor (nAChR) competitive modulators, butenolide nicotinic acetylcholine receptor (nAChR) competitive modulators, spinosyn nicotinic acetylcholine receptor (nAChR) allosteric modulators, avermectin and milbemycin glutamate-gated chloride channel (GluCI) allosteric modulators, juvenile hormone mimics, miscellaneous non-specific (multisite) inhibitors, pyridine azomethine derivative chordotonal organ TRPV channel modulators, mite growth inhibitors, microbial disruptors of insect midgut membranes, inhibitors of mitochondrial ATP synthase, uncouplers of oxidative phosphorylation via disruption of the proton gradient, nereistoxin analogue nicotinic acetylcholine receptor (nAChR) channel blockers, benzoylurea inhibitors of chitin biosynthesis (type 0), inhibitors of chitin biosynthesis (type 1), molting disruptors (dipteran), diacylhydrazine ecdysone receptor agonists, octopamine receptor agonists, mitochondrial complex III electron transport inhibitors, mitochondrial complex I electron transport inhibitors, voltage-dependent sodium channel blockers, tetronic acid and tetramic acid derivative inhibitors of acetyl CoA carboxylase, mitochondrial complex IV electron transport inhibitors, mitochondrial complex II electron transport inhibitors, diamide ryanodine receptor modulators, flonicamid chordotonal organ modulators (undefined target site), natural enemy insect, mite and nematode-based biopesticides, microbial pesticides, spiracle-blocking agrochemicals, pheromone agents, azadirachtin, benzomate (benzoximate), phenisobromolyate (bromopropylate), quinoxaline (quinomethionate), sodium aluminum fluoride, kelthane (such as dicofol), pyridalyl, pyrifluquinazon, sulfur, ferric phosphate agents, metaldehyde and 1,3-dichloropropene; a fungicide selected from the group consisting of acylanaline PA fungicides (phenylamides), oxazolidinone PA fungicides (phenylamides), butyrolactone PA fungicides (phenylamides), hydroxyl(2-amino)pyrimidines, isoxazole heteroaromatics, isothiazolone heteroaromatics, carboxylic acids, benzimidazole MBC fungicides (methyl benzimidazole carbamate), thiophanate MBC fungicides (methyl benzimidazole carbamate), N-phenyl carbamates, toluamide benzamides, ethylamino-thiazole-carboxamide thiazole carboxamides, phenylureas, pyridinylmethyl-benzamide benzamides, aminocyanoacrylate cyanoacrylates, pyrimidineamines, pyrazole-5-carboxamide pyrazole MET 1, phenyl-benzamide SDHI (succinate dehydrogenase inhibitors), phenyl-oxo-ethyl thiophene amide SDHI (succinate dehydrogenase inhibitors), pyridinyl-ethyl-benzamide SDHI (succinate dehydrogenase inhibitors), furan-carboxamide SDHI (succinate dehydrogenase inhibitors), oxathiin-carboxamide SDHI (succinate dehydrogenase inhibitors), thiazole-carboxamide SDHI (succinate dehydrogenase inhibitors), pyrazole-4-carboxamide SDHI (succinate dehydrogenase inhibitors), N-methoxy-(phenyl-ethyl)-pyrazole-carboxamide SDHI (succinate dehydrogenase inhibitors), pyridine-carboxamide SDHI (succinate dehydrogenase inhibitors), methoxy-acrylate QoI-fungicides (Quinone outside inhibitors), methoxy-acetamide QoI-fungicides (Quinone outside inhibitors), methoxy-carbamate QoI-fungicides (Quinone outside inhibitors), oximino-acetate QoI-fungicides (Quinone outside inhibitors), oximino-acetamide QoI-fungicides (Quinone outside inhibitors), oxazolidine-dione QoI-fungicides (Quinone outside inhibitors), dihydro-dioxazine QoI-fungicides (Quinone outside inhibitors), imidazolinone QoI-fungicides (Quinone outside inhibitors), benzyl-carbamate QoI-fungicides (Quinone outside inhibitors), cyano-imidazole QiI-fungicides (Quinone inside inhibitors), sulfamoyl-triazole QiI-fungicides (Quinone inside inhibitors), dinitrophenyl crotonates, 2,6-dinitroanilines, tri-phenyl tin compound organic tin compounds, thiophene carboxamides, triazolo-pyrimidylamine QoSI fungicides (Quinone outside inhibitors, stigmatellin binding type), anilino-pyrimidine AP-fungicides (aniline-pyrimidines), enopyranuronic acid antibiotics, hexopyranosyl antibiotics, glucopyranosyl antibiotics, tetracycline antibiotics, allyloxyquinoline aza-naphthalenes, quinazolinone aza-naphthalenes, phenylpyrrole PP-fungicides (phenylpyrroles), dicarboximides, phosphoro-thiolates, dithiolanes, aromatic hydrocarbon AH-fungicides (aromatic hydrocarbons, including chlorophenyls and nitroanilines), 1,2,4-thiadiazole heteroaromatics, carbamates, microbial (*Bacillus* species): *Bacillus* species and the fungicidal lipopeptide produced, terpene hydrocarbon and terpene alcohol plant extracts, piperazine DMI-fungicides (demethylation inhibitors, SBI: class I), pyridine DMI-fungicides (demethylation inhibitors, SBI: class I), pyrimidine DMI-fungicides (demethylation inhibitors, SBI: class I), imidazole DMI-fungicides (demethylation inhibitors, SBI: class I), triazole DMI-fungicides (demethylation inhibitors, SBI: class I), triazolinethione DMI-fungicides (demethylation inhibitors, SBI: class I), morpholine amines (morpholines, SBI: class II), piperidine amines (morpholines, SBI: class II), spiroketalamine amines (morpholines, SBI: class II), hydroxyanilides (SBI: class III), amino-pyrazolinones (SBI: class III), thiocarbamates (SBI: class IV), allylamines (SBI: class IV), glucopyranosyl antibiotics, peptidyl pyrimidine nucleotide polyoxines, cinnamic acid amide CAA-fungicides (carboxylic acid amides), valinamide carbamate CAA-fungicides (carboxylic acid amides), mandelic acid amide CAA-fungicides (carboxylic acid amides), isobenzo-furanone MBI-R (melanin biosynthesis inhibitors-reductase), pyrroloquinolinone MBI-R (melanin biosynthesis inhibitors-reductase), triazolobenzo-thiazole MBI-R (melanin biosynthesis inhibitors-reductase), cyclopropane-carboxamide MBI-D (melanin biosynthesis inhibitors-dehydratase), carboxamide MBI-D (melanin biosynthesis inhibitors-dehydratase), propionamide MBI-D (melanin biosynthesis inhibitors-dehydratase), trifluoroethyl-carbamate MBI-P (melanin biosynthesis inhibitors-polyketide synthase), benzo-thiadiazoles BTH, benzisothiazoles, thiadiazole-carboxamides, natural polysaccharides, plant extracts, cyanoacetamide-oximes, ethyl phosphonate phosphonates, phosphonates, phthalamic acids, benzotriazines, benzene-sulfonamides, pyridazinones, thiocarbamates, phenyl-acetamides, benzophenone allyl-phenyl-ketones, benzoylpyridine allyl-phenyl-ketones, guanidines, cyanomethylene-thiazolidine thiazolidines, pyrimidinone-hydrazones, piperidinyl-thiazole-isoxazolines, 4-quinoline-acetates, tetrazolyloximes, glucopyranosyl antibiotics, inorganic compounds, dithio-carbamates and analogues thereof, phthalimides, chloronitriles (phthalonitriles), sulfamides, bis-guanidines, triazines, quinones (anthraquinones), quinoxalines, maleimides, polypeptides, physical inhibitors, bicarbonate agents, silver agents, organic copper agents and soil disinfectants; or, a herbicide selected from the group consisting of allyloxy propionate inhibitors of acetyl CoA carboxylase (ACCase), cyclohexanedione inhibitors of acetyl CoA carboxylase (ACCase), phenylpyrazoline inhibitors of acetyl CoA carboxylase (ACCase), sulfonylurea inhibitors of acetolactic acid synthase (ALS) (acetohydroxy acid synthase (AHAS) inhibitors), imidazolinone inhibitors of acetolactic acid synthase (ALS) (acetohydroxy acid synthase (AHAS) inhibitors), triazolopyrimidine inhibitors of acetolactic acid synthase (ALS) (acetohydroxy acid synthase (AHAS) inhibitors), pyrimidinyl(thio)benzoate inhibitors of acetolactic acid synthase (ALS) (acetohydroxy acid synthase (AHAS) inhibitors), sulfonylaminocarbonyl-triazolinone inhibitors of acetolactic acid synthase (ALS) (acetohydroxy acid synthase (AHAS) inhibitors), triazine inhibitors of photosynthesis at photochemical system II, triazinone inhibitors of photosynthesis at photochemical system II, triazolinone inhibitors of photosynthesis at photochemical system II, uracil inhibitors of photosynthesis at photochemical system II, pyridazinone inhibitors of photosynthesis at photochemical system II, phenylcarbamate inhibitors of photosynthesis at photochemical system II, urea inhibitors of photosynthesis at photochemical system II, amide inhibitors of photosynthesis at photochemical system II, nitrile inhibitors of photosynthesis at photochemical system II, benzothiadiazinone inhibitors of photosynthesis at photochemical system II, phenyl-pyridazine inhibitors of photosynthesis at photochemical system II, bipyridylium photochemical system I electron diverting agents, diphenylether inhibitors of protoporphyrinogen oxidase (PPO), phenylpyrazole inhibitors of protoporphyrinogen oxidase (PPO), N-phenylphthalimide inhibitors of protoporphyrinogen oxidase (PPO), thiadiazole inhibitors of protoporphyrinogen oxidase (PPO), oxadiazole inhibitors of protoporphyrinogen oxidase (PPO), triazolinone inhibitors of protoporphyrinogen oxidase (PPO), oxazolidinedione inhibitors of protoporphyrinogen oxidase (PPO), pyrimidindione inhibitors of protoporphyrinogen oxidase (PPO), inhibitors of protoporphyrinogen oxidase (PPO), pyridazinone inhibitors of carotenoid biosynthesis at the phytoene desaturase step (PDS), pyridinecarboxamide inhibitors of carotenoid biosynthesis at the phytoene desaturase step (PDS), inhibitors of carotenoid biosynthesis at the phytoene desaturase step (PDS), triketone inhibitors of 4-hydroxyphenyl-pyruvate-dioxygenase (4-HPPD), isoxazole inhibitors of 4-hydroxyphenyl-pyruvate-dioxygenase (4-HPPD), pyrazole inhibitors of 4-hydroxyphenyl-pyruvate-dioxygenase (4-HPPD), inhibitors of 4-hydroxyphenyl-pyruvate-dioxygenase (4-HPPD), triazole inhibitors of carotenoid biosynthesis (unknown target site), isoxazolidinone inhibitors of carotenoid biosynthesis (unknown target site), urea inhibitors of carotenoid biosynthesis (unknown target site), diphenylether inhibitors of carotenoid biosynthesis (unknown target site), glycine inhibitors of EPSP synthase, phosphinic acid inhibitors of glutamine synthetase, carbamate inhibitors of DHP (dihydropteroate) synthase, dinitroaniline microtubule assembly inhibitors, phosphoramidate microtubule assembly inhibitors, pyridine microtubule assembly inhibitors, benzamide microtubule assembly inhibitors, benzoic acid microtubule assembly inhibitors, carbamate inhibitors of mitosis/microtubule organisation, chloroacetamide inhibitors of VLCFAs (inhibitors of cell division), acetamide inhibitors of VLCFAs (inhibitors of cell division), oxyacetamide inhibitors of VLCFAs (inhibitors of cell division), tetrazolinone inhibitors of VLCFAs (inhibitors of cell division), inhibitors of VLCFAs (inhibitors of cell division), nitrile inhibitors of cell wall (cellulose) synthesis, benzamide inhibitors of cell wall (cellulose) synthesis, triazolocarboxamide inhibitors of cell wall (cellulose) synthesis, quinoline carboxylic acid inhibitors of cell wall (cellulose) synthesis, dinitrophenol uncoupling (membrane disruption) agents, thiocarbamate inhibitors of lipid synthesis (non-ACCase inhibitors), phosphorodithioate inhibitors of lipid synthesis (non-ACCase inhibitors), benzofuran inhibitors of lipid synthesis (non-ACCase inhibitors), chloro-carbonic-acid inhibitors of lipid synthesis (non-ACCase inhibitors), phenoxy-carboxylic-acid indole acetic acid-like agents (synthetic auxins), benzoic acid indole acetic acid-like agents (synthetic auxins), pyridine carboxylic acid indole acetic acid-like agents (synthetic auxins), quinoline carboxylic acid indole acetic acid-like agents (synthetic auxins), indole acetic acid-like agents (synthetic auxins), phthalamate inhibitors of auxin transport, semicarbazone inhibitors of auxin transport, arylaminopropionic acids, pyrazoliums, organoarsenicals, microorganisms, bromobutide, (chlor)-flurenol, cinmethylin, cumyluron, dazomet, dymron, methyl dymron, etobenzanid, fosamine, indanofan, carbam/carbam sodium salt, oxaziclomefone, oleic acid, pelargonic acid, pyributicarb, chlorates and cyanates.

4. The formulation according to claim 1, wherein the active agrochemical comprises:

an insecticide selected from the group consisting of carbamate acetylcholinesterase (AChE) inhibitors, organophosphorous acetylcholinesterase (AChE) inhibitors, phenylpyrazole (fiprole) GABA-gated chlorine ion channel blockers, pyrethroid and pyrethrin sodium channel modulators, sodium channel modulators, neonicotinoid nicotinic acetylcholine receptor (nAChR) competitive modulators, sulfoximine nicotinic acetylcholine receptor (nAChR) competitive modulators, spinosyn nicotinic acetylcholine receptor (nAChR) allosteric modulators, avermectin and milbemycin glutamate-gated chloride channel (GluCl) allosteric modulators, chordotonal organ TRPV channel modulators, uncouplers of oxidative phosphorylation via disruption of the proton gradient, mitochondrial complex III electron transport inhibitors, mitochondrial complex I electron transport inhibitors, voltage-dependent sodium channel blockers, tetronic acid and tetramic acid derivative inhibitors of acetyl CoA carboxylase, diamide ryanodine receptor modulators, flonicamid chordotonal organ modulators (undefined target site), quinoxaline (quinomethionate), pyridalyl and metaaldehyde; or, a fungicide selected from the group consisting of acylanaline PA fungicides (phenylamides), oxazolidinone PA fungicides (phenylamides), butyrolactone PA fungicides (phenylamides), isoxazole heteroaromatics, benzimidazole MBC fungicides (methyl benzimidazole carbamate), N-phenyl carbamates, phenyl-benzamide SDHI (succinate dehydrogenase inhibitors), phenyl-oxo-ethyl thiophene amide SDHI (succinate dehydrogenase inhibitors), pyridinyl-ethyl-benzamide SDHI (succinate dehydrogenase inhibitors), furan-carboxamide SDHI (succinate dehydrogenase inhibitors), oxathiin-carboxamide SDHI (succinate dehydrogenase inhibitors), thiazole-carboxamide SDHI (succinate dehydrogenase inhibitors), pyrazole-4-carboxamide SDHI (succinate dehydrogenase inhibitors), N-methoxy-(phenyl-ethyl)-pyrazole-carboxamide SDHI (succinate dehydrogenase inhibitors), pyridine-carboxamide SDHI (succinate dehydrogenase inhibitors), methoxy-acrylate QoI-fungicides (Quinone outside inhibitors), methoxy-acetamide QoI-fungicides (Quinone outside inhibitors), methoxy-carbamate QoI-fungicides (Quinone outside inhibitors), oximino-acetate QoI-fungicides (Quinone outside inhibitors), oximino-acetamide QoI-fungicides (Quinone outside inhibitors), oxazolidine-dione QoI-fungicides (Quinone outside inhibitors), dihydro-dioxazine QoI-fungicides (Quinone outside inhibitors), imidazolinone QoI-fungicides (Quinone outside inhibitors), benzyl-carbamate QoI-fungicides (Quinone outside inhibitors), cyano-imidazole QiI-fungicides (Quinone inside inhibitors), sulfamoyl-triazole QiI-fungicides (Quinone inside inhibitors), 2,6-dinitroanilines, anilino-pyrimidine AP-fungicides (aniline-pyrimidines), phenylpyrrole PP-fungicides (phenylpyrroles), dicarboximides, piperazine DMI-fungicides (demethylation inhibitors, SBI: class I), pyridine DMI-fungicides (demethylation inhibitors, SBI: class I), pyrimidine DMI-fungicides (demethylation inhibitors, SBI: class I), imidazole DMI-fungicides ((demethylation inhibitors, SBI: class I), triazole DMI-fungicides (demethylation inhibitors, SBI: class I), triazolinethione DMI-fungicides (demethylation inhibitors, SBI: class I), isobenzo-furanone MBI-R (melanin biosynthesis inhibitors-reductase), pyrrolo-quinolinone MBI-R (melanin biosynthesis inhibitors-reductase), triazolobenzo-thiazole MBI-R (melanin biosynthesis inhibitors-reductase), cyclopropane-carboxamide MBI-D (melanin biosynthesis inhibitors-dehydratase), carboxamide MBI-D (melanin biosynthesis inhibitors-dehydratase), propionamide MBI-D (melanin biosynthesis inhibitors-dehydratase), benzo-thiadiazoles BTH, benzisothiazoles, thiadiazole-carboxamides, cyanoacetamide-oximes, benzene-sulfonamides, pyridazinones, guanidines and quinoxalines.

5. The formulation according to claim 1, wherein the active agrochemical comprises:
an insecticide selected from the group consisting of carbamate acetylcholinesterase (AChE) inhibitors, organophosphorous acetylcholinesterase (AChE) inhibitors, phenylpyrazole (fiprole) GABA-gated chlorine ion channel blockers, pyrethroid and pyrethrin sodium channel modulators, sodium channel modulators, neonicotinoid nicotinic acetylcholine receptor (nAChR) competitive modulators, sulfoximine nicotinic acetylcholine receptor (nAChR) competitive modulators, avermectin and milbemycin glutamate-gated chloride channel (GluCl) allosteric modulators, chordotonal organ TRPV channel modulators, uncouplers of oxidative phosphorylation via disruption of the proton gradient, diamide ryanodine receptor modulators, and flonicamid chordotonal organ modulators (undefined target site); or,
a fungicide selected from the group consisting of isoxazole heteroaromatics, benzimidazole MBC fungicides (methyl benzimidazole carbamate), phenyl-benzamide SDHI (succinate dehydrogenase inhibitors), phenyl-oxo-ethyl thiophene amide SDHI (succinate dehydrogenase inhibitors), pyridinyl-ethyl-benzamide SDHI (succinate dehydrogenase inhibitors), furan-carboxamide SDHI (succinate dehydrogenase inhibitors), oxathiin-carboxamide SDHI (succinate dehydrogenase inhibitors), thiazole-carboxamide SDHI (succinate dehydrogenase inhibitors), pyrazole-4-carboxamide SDHI (succinate dehydrogenase inhibitors), [N-methoxy-(phenyl-ethyl)-pyrazole-carboxamide SDHI (succinate dehydrogenase inhibitors)], pyridine-carboxamide SDHI (succinate dehydrogenase inhibitors), methoxy-acrylate QoI-fungicides (Quinone outside inhibitors), methoxy-acetamide QoI-fungicides (Quinone outside inhibitors), methoxy-carbamate QoI-fungicides (Quinone outside inhibitors), oximino-acetate QoI-fungicides (Quinone outside inhibitors), oximino-acetamide QoI-fungicides (Quinone outside inhibitors), oxazolidine-dione QoI-fungicides (Quinone outside inhibitors), dihydro-dioxazine QoI-fungicides (Quinone outside inhibitors), imidazolinone QoI-fungicides (Quinone outside inhibitors), benzyl-carbamate QoI-fungicides (Quinone outside inhibitors), piperazine DMI-fungicides (demethylation inhibitors, SBI: class I), pyridine DMI-fungicides (demethylation inhibitors, SBI: class I), pyrimidine DMI-fungicides (demethylation inhibitors, SBI: class I), imidazole DMI-fungicides ((demethylation inhibitors, SBI: class I), triazole DMI-fungicides (demethylation inhibitors, SBI: class I), triazolinethione DMI-fungicides (demethylation inhibitors, SBI: class I).

6. The formulation according to claim 1, wherein the active agrochemical has aqueous solubility at 25° C. of 100 ppm or more.

7. The formulation according to claim 1, wherein the active agrochemical comprises:
an insecticide selected from the group consisting of aldicarb, bendiocarb, butocarboxim, butoxycarboxim, NAC (carbaryl), carbofuran, ethiofencarb, BPMC (fenobucarb), formetanate, MIPC (isoprocarb), methomyl, MTMC (metolcarb), oxamyl, pirimicarb, PHC (propoxur), thiofanox, triazamate, XMC, MPMC (xylylcarb), acephate, azamethiphos, cadusafos, CVP (chlorfenvinphos), demeton-S-methyl, DDVP (dichlorvos), dicrotophos, dimethoate, dimethylvinphos, ethoprophos, fenamiphos, fosthiazate, heptenophos, marathon (malathion), mecarbam, methamidophos, DMTP (methidathion), mevinphos, monocrotophos, omethoate, oxydimethone-methyl, phosphamidon, propetamphos, thiometone, DEP (trichlorfon), vamidothion, flumethrin, acetamiprid, clothianidin, dinotefuran, imidacloprid, nitenpyram, thiacloprid, thiamethoxam, nicotine sulfate (nicotine), sulfoxaflor, flupyradifurone, pyriproxyfen, methyl bromide (methylbromide), chloropicrin, sulfuryl fluoride, borax, tartar emetic, pymetrozine, flonicamid, BPPS (propargite), DNOC, cartap, thiocyclam, thiosultap-sodium, cyromazine, hydrogen phosphide, hydrogen cyanide, azadirachtin, sodium aluminum fluoride, 1,3-dichloropropene, dicyclanil, ethylene dibromide, sabadilla and sulcofuron-sodium; or, a fungicide selected from the group consisting of furalaxyl, metalaxyl, metalaxyl M, oxadixyl, ofurace, dimethirimol, hydroxyisoxazole (hymexazol), octhilinone, fenfuram, carboxin, oxycarboxin, furametpyr, metominostrobin, cyazofamid, pyrimethanil, kasugamycin, streptomycin, IBP (iprobenfos), echlomezol (etridiazole), propamocarb, prothiocarb, pyrifenox, imazalil, pefurazoate, triflumizole, flutriafol, myclobutanil, propiconazole, tetraconazole, fenpropidin, spiroxamine, validamycin, polyoxin, iprovalicarb, pyroquilon, cymoxanil, fosetyl, phosphorous acid and phosphites, flusulfamide, methasulfocarb, guanidine (dodine), ferimzone, potassium bicarbonate, ferbam, guazatine, iminoctadine acetate/iminoctadine albesilate (iminoctadine), copper sulfate, formaldehyde, 8-hydroxyquinoline sulfate, iodomethane, mercuric chloride, metam, methyl bromide, methyl isothiocyanate, mildiomycin, nabam, phenylmercuric acetate, 2-phenylphenol and polyoxin.

8. The formulation according to claim 1, wherein the active agrochemical comprises at least one selected from the group consisting of acetamiprid, imidacloprid, clothianidin, dinotefuran, thiacloprid, thiamethoxam, nitenpyram and flonicamid.

9. The formulation according to claim 1, wherein the active agrochemical comprises at least one of neonicotinoid selected from the group consisting of acetamiprid, imidacloprid, clothianidin, dinotefuran, thiacloprid, thiamethoxam and nitenpyram.

10. The formulation according to claim 1, wherein the active agrochemical comprises at least one of neonicotinoid selected from the group consisting of acetamiprid, imidacloprid, clothianidin, dinotefuran and thiamethoxam.

11. The formulation according to claim 1, wherein the active agrochemical comprises dinotefuran.

12. The formulation according to claim 1, wherein the fertilizer is a soluble fertilizer.

13. The formulation according to claim 12, wherein the soluble fertilizer comprises any of one or more of fertilizer components selected from the group consisting of nitrogen (N), phosphorous (P), potassium (K), silicon (Si), magnesium (Mg), manganese (Mn), boron (B), calcium (Ca) and sulfur (S) as plant essential elements.

14. The formulation according to claim 12, wherein the soluble fertilizer comprises at least two of fertilizer components selected from the group consisting of nitrogen (N), phosphorous (P) and potassium (K) as plant essential elements.

15. The formulation according to claim 12, wherein the soluble fertilizer comprises the fertilizer components of nitrogen (N), phosphorous (P) and potassium (K) as plant essential elements.

16. The formulation according to claim 12, wherein the soluble fertilizer further comprises any of one or more of fertilizer components selected from the group consisting of iron (Fe), copper (Cu), zinc (Zn), molybdenum (Mo), cobalt (Co) and chlorine (Cl) as plant essential elements.

17. The formulation according to claim 12, wherein the soluble fertilizer comprises nitrogen (N), phosphorous (P) and potassium (K) at a ratio of 1:2:1.

18. The formulation according to claim 12, wherein the soluble fertilizer comprises nitrogen (N), phosphorous (P) and potassium (K) at a ratio of 1.2:2:1.

19. The formulation according to claim 12, wherein the content ratio of the soluble fertilizer is 0.1% by weight to 95% by weight with respect to the total weight of the formulation.

20. The formulation according to claim 1, wherein the glycol ether comprises at least one selected from the group consisting of ethylene glycol monomethyl ether, ethylene glycol monoethyl ether, ethylene glycol monopropyl ether, ethylene glycol monoisopropyl ether, ethylene glycol monobutyl ether, ethylene glycol monoisobutyl ether, ethylene glycol mono-t-butyl ether, ethylene glycol mono-2-methylpentyl ether, ethylene glycol monohexyl ether, ethylene glycol mono-2-ethylhexyl ether, ethylene glycol monovinyl ether, ethylene glycol monoallyl ether, ethylene glycol monobenzyl ether, ethylene glycol monophenyl ether, ethylene glycol dimethyl ether, ethylene glycol diethyl ether, diethylene glycol monomethyl ether, diethylene glycol monoethyl ether, diethylene glycol monopropyl ether, diethylene glycol monoisopropyl ether, diethylene glycol monobutyl ether, diethylene glycol monoisobutyl ether, diethylene glycol monohexyl ether, diethylene glycol mono-2-ethylhexyl ether, diethylene glycol monoallyl ether, diethylene glycol monobenzyl ether, diethylene glycol monophenyl ether, diethylene glycol mono(methylphenyl) ether, diethylene glycol dimethyl ether, diethylene glycol methyl ethyl ether, diethylene glycol diethyl ether, diethylene glycol dibutyl ether, diethylene glycol divinyl ether, diethylene glycol ethyl vinyl ether, triethylene glycol monomethyl ether, triethylene glycol monoethyl ether, triethylene glycol monobutyl ether, triethylene glycol monovinyl ether, triethylene glycol dimethyl ether, tetraethylene glycol monophenyl ether, tetraethylene glycol diethyl ether, polyethylene glycol monomethyl ether, propylene glycol monomethyl ether, propylene glycol monoethyl ether, propylene glycol monopropyl ether, propylene glycol monoisopropyl ether, propylene glycol monobutyl ether, propylene glycol phenyl ether, propylene glycol mono(methylphenyl) ether, propylene glycol dimethyl ether, propylene glycol diethyl ether, propylene glycol dipropyl ether, propylene glycol diisopropyl ether, propylene glycol dibutyl ether, propylene glycol diisobutyl ether, propylene glycol diallyl ether, propylene glycol diphenyl ether, dipropylene glycol monomethyl ether, dipropylene glycol monoethyl ether, dipropylene glycol monopropyl ether, dipropylene glycol monobutyl ether, dipropylene glycol dimethyl ether, dipropylene glycol diethyl ether, dipropylene glycol dibutyl ether, dipropylene glycol diisobutyl ether, dipropylene glycol allyl ether, tripropylene glycol monomethyl ether, tripropylene glycol monoethyl ether, tripropylene glycol monobutyl ether, butylene glycol monomethyl ether, butylene glycol dimethyl ether and 3-methoxy-3-methyl-1-butanol.

21. The formulation according to claim 1, wherein the glycol ether comprises at least one selected from the group consisting of ethylene glycol monomethyl ether, ethylene glycol monoethyl ether, ethylene glycol monopropyl ether, ethylene glycol monoisopropyl ether, ethylene glycol monobutyl ether, ethylene glycol monoisobutyl ether, ethylene glycol monoallyl ether, diethylene glycol monomethyl ether, diethylene glycol monoethyl ether, diethylene glycol monopropyl ether, diethylene glycol monoisopropyl ether, diethylene glycol monobutyl ether, diethylene glycol monoisobutyl ether, diethylene glycol monobenzyl ether, diethylene glycol dimethyl ether, diethylene glycol methyl ethyl ether, diethylene glycol diethyl ether, triethylene glycol monomethyl ether, triethylene glycol monobutyl ether, triethylene glycol dimethyl ether, polyethylene glycol monomethyl ether, propylene glycol monomethyl ether, propylene glycol monopropyl ether, propylene glycol monobutyl ether, dipropylene glycol monomethyl ether, dipropylene glycol monopropyl ether, tripropylene glycol monomethyl ether, butylene glycol monomethyl ether and 3-methoxy-3-methyl-1-butanol.

22. The formulation according to claim 1, wherein the glycol ether comprises at least one selected from the group consisting of ethylene glycol monoisopropyl ether, ethylene glycol monobutyl ether, ethylene glycol monoisobutyl ether, ethylene glycol monoallyl ether, diethylene glycol monomethyl ether, diethylene glycol monoisopropyl ether, diethylene glycol monobutyl ether, diethylene glycol monoisobutyl ether, diethylene glycol monobenzyl ether, diethylene glycol dimethyl ether, diethylene glycol diethyl ether, diethylene glycol methyl ethyl ether, triethylene glycol monomethyl ether, triethylene glycol monobutyl ether, triethylene glycol dimethyl ether, polyethylene glycol monomethyl ether, propylene glycol monomethyl ether, propylene glycol monopropyl ether, dipropylene glycol monomethyl ether, tripropylene glycol monomethyl ether and 3-methoxy-3-methyl-1-butanol.

23. The formulation according to claim 1, wherein the glycol ether comprises at least one selected from the group consisting of ethylene glycol monobutyl ether, ethylene glycol monoisobutyl ether, ethylene glycol monoallyl ether, diethylene glycol monobutyl ether, diethylene glycol monoisobutyl ether, diethylene glycol monobenzyl ether, propylene glycol monopropyl ether and 3-methoxy-3-methyl-1-butanol.

24. The formulation according to claim 1, wherein the glycol ether comprises 3-methoxy-3-methyl-1-butanol.

25. The formulation according to claim 1, wherein the content ratio of glycol ether is 0.1% by weight to 15% by weight with respect to the total weight of the formulation.

26. The formulation according to claim 1, wherein the content ratio of active agrochemical is 0.01% by weight to 10% by weight, the content ratio of glycol ether is 0.1% by weight to 15% by weight, and the content ratio of soluble fertilizer is 0.1% by weight to 95% by weight, wherein the content ratios are with respect to the total weight of the formulation.

27. The formulation according to claim 26, wherein the content ratio of active agrochemical is 0.03% by weight to 5% by weight, the content ratio of glycol ether is 3% by weight to 10% by weight, and the content ratio of soluble fertilizer is 50% by weight to 85% by weight, wherein the content ratios are with respect to the total weight of the formulation.

28. An aqueous composition for producing the formulation according to claim 1, wherein the aqueous composition comprising a glycol ether, an active agrochemical and water.

29. The aqueous composition according to claim 28, wherein the glycol ether comprises at least one selected from the group consisting of ethylene glycol monobutyl ether, ethylene glycol monoisobutyl ether, ethylene glycol monoallyl ether, diethylene glycol monobutyl ether, diethylene glycol monoisobutyl ether, diethylene glycol monobenzyl ether, propylene glycol monopropyl ether and 3-methoxy-3-methyl-1-butanol.

30. The aqueous composition according to claim 28, wherein the glycol ether comprises 3-methoxy-3-methyl-1-butanol.

31. The aqueous composition according to claim 28, wherein the active agrochemical comprises at least one of neonicotinoid selected from the group consisting of acetamiprid, imidacloprid, clothianidin, dinotefuran, thiacloprid, thiamethoxam and nitenpyram.

32. The aqueous composition according to claim 28, wherein the active agrochemical comprises dinotefuran.

33. A transparent, homogeneous liquiform fertilizer and agrochemical aqueous composition obtained by adding water to the formulation according to claim 1.

34. A method of using the formulation according to claim 1 for agriculture, horticulture or home garden comprising applying the formulation to foliage or seeds.

35. The formulation according to claim 1, wherein the particle diameter of particles in the transparent, homogeneous liquiform fertilizer and agrochemical formulation is less than 10 nm by using a particle size distribution analyzer.

36. The formulation according to claim 1, wherein the particle diameter of particles in the transparent, homogeneous liquiform fertilizer and agrochemical formulation is less than 1 nm by using a particle size distribution analyzer.

* * * * *